US012590135B2

(12) United States Patent
Laurent et al.

(10) Patent No.: US 12,590,135 B2
(45) Date of Patent: Mar. 31, 2026

(54) STABILIZED EXTRACELLULAR DOMAIN OF CD19

(71) Applicant: Universität für Bodenkultur Wien, Vienna (AT)

(72) Inventors: Elisabeth Laurent, Vienna (AT); Michael Traxlmayr, Vienna (AT); Renate Kunert, Vienna (AT)

(73) Assignee: UNIVERSITÄT FÜR BODENKULTUR WIEN, Vienna (AT)

( * ) Notice: Subject to any disclaimer, the term of this patent is extended or adjusted under 35 U.S.C. 154(b) by 1205 days.

(21) Appl. No.: 17/435,370

(22) PCT Filed: Feb. 12, 2020

(86) PCT No.: PCT/EP2020/053552
§ 371 (c)(1),
(2) Date: Aug. 31, 2021

(87) PCT Pub. No.: WO2020/177992
PCT Pub. Date: Sep. 10, 2020

(65) Prior Publication Data
US 2022/0144917 A1     May 12, 2022

(30) Foreign Application Priority Data
Mar. 1, 2019   (EP) .................................... 19160231

(51) Int. Cl.
| *C07K 19/00* | (2006.01) |
| *C07K 14/705* | (2006.01) |
| *G01N 33/68* | (2006.01) |
| *A61K 38/00* | (2006.01) |

(52) U.S. Cl.
CPC ....... *C07K 14/70503* (2013.01); *G01N 33/68* (2013.01); *A61K 38/00* (2013.01); *C07K 2319/00* (2013.01); *G01N 2333/70503* (2013.01)

(58) Field of Classification Search
None
See application file for complete search history.

(56) References Cited

FOREIGN PATENT DOCUMENTS

| WO | 2017055328 A1 | 4/2017 |
| WO | 2018156802 A1 | 8/2018 |
| WO | 2018161017 A1 | 9/2018 |

OTHER PUBLICATIONS

Angelini, A. et al. "Protein Engineering and Selection Using Yeast Surface Display", Methods in molecular biology, vol. 1319, pp. 3-36 (2015).

Blazer, L.L. et al. "Use of Flow Cytometric Methods to Quantify Protein-Protein Interactions", Current protocols in cytometry, Unit 13.1115, Jan. 2010, 18 pgs.

Chao, G et al. "Isolating and engineering human antibodies using yeast surface display", Nature Publishing Group, vol. 1, No. 2, pp. 755-768 (2006).

Yamabe, E. et al. "Database UniProt, XP002791538", retrieved from EBI accession No. Un i prot: Q3 LRP3, Feb. 13, 2009, 3 pages.

Gibbs, R.A. et al. "Database UniProt, XP55682996", retrieved from EBI accession No. UNIPROT:F1 LNH2 Database accession No. F1 LNH2a, Jan. 16, 2019, 4 pgs.

Durocher, Y. et al. "High-level and high-throughput recombinant protein production by transient transfection of suspension-growing human 293-EBNA1 cells", Nucleic acids research, 2002, vol. 30, No. 2, E9, 9 pgs.

Hasenhindl, C. et al. "Stability assessment on a library scale: a rapid method for the evaluation of the commutability and insertion of residues in C-terminal loops of the CH3 domains of IgG1-Fc", Protein Engineering, Design & Selection, vol. 26 No. 10, (2013), pp. 675-682.

Jena, Bipulendu et al. "Chimeric Antigen Receptor (CAR)-Specific Monoclonal Antibody to Detect CD19-Specific T Cells in Clinical Trials", PloS ONE, 2013, vol. 8, No. 3, e57838, 12 pgs.

Klesmith, J R et al. "Retargeting CD19 CAR T cells via engineered CD19-fusion proteins", Mol. Pharmaceutics, 2019, vol. 16, No. 8, pp. 3544-3558.

Li, X et al., "CD19, from bench to bedside", Immunology letters, (2017), vol. 183, pp. 86-95.

Nature Publishing Group, "Genome sequence of the Brown Norway rat yields insights into mammalian evolution", Nature, vol. 428(1): 493-521 (2004).

De Oliveira, Satiro N. et al. "A CD19/Fc fusion protein for detection of anti-CD19 chimeric antigen receptors", Journal of Translational Medicine, 2013, vol. 11, No. 23, 9 pgs.

Teplyakov, Alexey et al. "Crystal structure of B-cell co-receptor CD19 in complex with antibody B43 reveals an unexpected fold", Proteins, 2018, vol. 86, No. 5, pp. 495-500.

Traxlmayr, M W et al. "Directed evolution of Her2/neu-binding IgG I-Fc for improved stability and resistance to aggregation by using yeast surface display", Protein Engineering, Design & Selection vol. 26, No. 4, pp. 255-265 (2013).

Traxlmayr, M W et al. "Directed Evolution of Protein Thermal Stability Using Yeast Surface Display", Methods in molecular biology, vol. 1575, pp. 45-65 (2017).

(Continued)

*Primary Examiner* — Christine J Saoud
*Assistant Examiner* — Jon M Lockard
(74) *Attorney, Agent, or Firm* — LOZA & LOZA, LLP; Michael Fedrick

(57) ABSTRACT

An extracellular domain of CD19 (CD19-ECD) which comprises at least 90% sequence identity to SEQ ID NO:1, a first core region at positions 2-98 of SEQ ID NO:1, a second core region at positions 167-258 of SEQ ID NO:1, a third core region at positions 99-166 of SEQ ID NO:1, and at least one stabilizing point mutation at an amino acid position within said first and/or second and/or third core regions, wherein the CD19-ECD has an increased thermal stability compared to CD19-ECD which consists of an amino acid sequence identified as SEQ ID NO:1.

Figure 2:
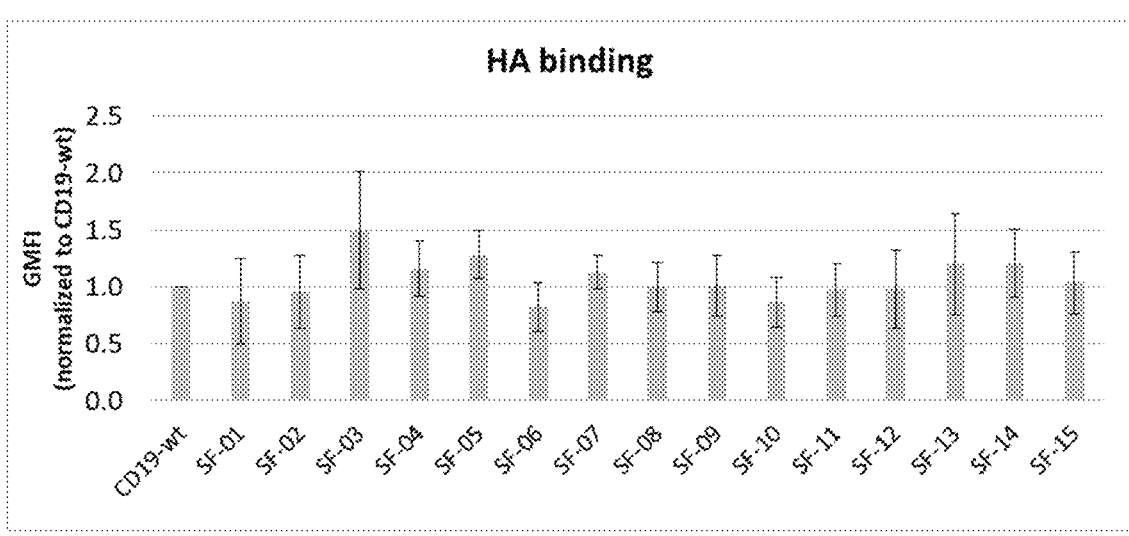

13 Claims, 27 Drawing Sheets
Specification includes a Sequence Listing.

(56)         References Cited

OTHER PUBLICATIONS

Zhou, L J et al. "Structure and domain organization of the CD19 antigen of human, mouse, and guinea pig B lymphocytes. Conservation of the extensive cytoplasmic domain", The Journal of Immunology, 1991, vol. 147, No. 4, pp. 1424-1432.

Zola, H. et al. "Preparation and characterization of a chimeric CD 19 monoclonal antibody", Immunology and Cell Biology, 1991, vol. 69, pp. 411-422.

European Patent Appln. No. 19160231.7, Partial European Search Report dated May 23, 2019.

European Patent Appln. No. 19160231.7, Extended European Search Report dated Sep. 20, 2019.

International Patent Application No. PCT/EP2020/053552, Partial International Search Report dated Apr. 15, 2020.

International Patent Application No. PCT/EP2020/053552, International Search Report dated Jun. 25, 2020.

International Patent Application No. PCT/EP2020/053552, Written Opinion dated Dec. 4, 2017.

International Patent Application No. PCT/EP2017/072880, International Preliminary Report of Patentability (Sep. 12, 2017).

Fig. 1

Sequences referred to herein:

SEQ ID NO:1:

CD19-wt, wtCD19-ECD, extracellular domain 1-259, first and second core regions indicated in bold

**PEEPLVVKVEEGDNAVLQCLKGTSDGPTQQLTWSRESPLKPFLKLSLGLPGLGIHMRPLA
IWLFIFNVSQQMGGFYLCQPGPPSEKAWQPGWTVNVEG**SGELFRWNVSDLGGLGCGLKNRSSEG
PSSPSGKLMSPKLYVWAKDRPEIWEGEPPCLPPRDSLNQSLS**QDLTMAPGSTLWLSCGVPPDSV
SRGPLSWTHVHPKGPKSLLSLELKDDRPARDMWVMETGLLLPRATAQDAGKYYCHRGNLTMSFH
LEITARP**

SEQ ID NO:2

First core region (E2-G98)
EEPLVVKVEEGDNAVLQCLKGTSDGPTQQLTWSRESPLKPFLKLSLGLPGLGIHMRPLAIWLFI
FNVSQQMGGFYLCQPGPPSEKAWQPGWTVNVEG

SEQ ID NO:3

Second core region (Q167-R258)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR

SEQ ID NO:4

Third core region (S99-S166)
SGELFRWNVSDLGGLGCGLKNRSSEGPSSPSGKLMSPKLYVWAKDRPEIWEGEPPCLPPRDSLN
QSLS

SEQ ID NO:5

First core region of clone A (point mutation underlined)
EEPLVVKVEEGDDAVLQCLKGTSDGPNQQLTWSRESPLKPFLKLSLGLPGLGIHMRPLAIWLFI
FNVSQQMGGFYLCQPGPPSEKAWQPGWTVNVEG

SEQ ID NO:6

First core region of clone B (point mutation underlined)
EEPLVVKVEEGDNAVLQCLKGTSDGPTQQLTWSRESPLKPFLKLSLGLPGLGIHMRPLAIWLSI
FNVSQQMGGFYLCQPGPPSEKAWQPGWTVNVEG

SEQ ID NO:7

First core region of clone C (point mutation underlined)
EEPLVVKVEEGDDAVLQCLKGTSDGPTQQLTWSRESPLKPFLRLSLGLPGLGIHMRPLAISLFI
FNVSQQMGGFYLCQPGPPSEKAWQPGWTVNVEG

Fig. 1 (continued)

SEQ ID NO:8

```
First core region of clone D (point mutation underlined)
EEPLVVKVEEGDNAVLQCLKGTSDGPTQQLTWSRESPLKPFLKLSLGLPGLGIHIRPLAIWLFI
FNVSQQMGGFYLCQPGPPSEKAWQPGWTVNVEG
```

SEQ ID NO:9

```
First core region of clone E (point mutation underlined)
EEPLVVKVEEGDNAVLQCLKGTSDGPTQQLTWSRESPLKPFLKLSLGLPGLGIHVSPLAIWLFI
SNVSQQMGGFYLCQPGPPSEKAWQPGWTVNVEG
```

SEQ ID NO:10

```
First core region of clone F (point mutation underlined)
EEPLVVKVEEGDNAVLQCLKGTSDGPTQQLTWSRESPLKPFLKLSLGLPGLGIHMRPLAIWLFI
FNVSQRMGGFYLCQPGPPSEKAWQPGWTVNVEG
```

SEQ ID NO:11

```
First core region of clone G (point mutation underlined)
EEPLVVKVEEGDNAVLQCLKGTSDGPTQQLTWSRESPLKPFLKLSLGLPGLGIHIRPLAIWLFI
LNVSQQMGGFYLCQPGPPSEKAWQPGWTVNVEG
```

SEQ ID NO:12

```
First core region of clone H (point mutation underlined)
EEPLVVKVEEGDNAVLQCLKGTSDGPTQQLTWSRESPLKPFLKLSLGLPGLGIHMSPLAIRLFI
FNVSQQMGGFYLCQPGPPSEKAWQPGWTVNVEG
```

SEQ ID NO:13

```
First core region of clone I (point mutation underlined)
EEPLVVKVEEGDNAVLQCLKGTSDGPTQQLTWSRESPLKPFLKLSLGLPGLGIHMSPLAIRLFI
FNVSQQMGGFYLCQPGPPSEKAWQPGWTVNVEG
```

SEQ ID NO:14

```
First core region of clone J (point mutation underlined)
EEPLVVKVEEGDNAVLQCLKGTSDGPTQQLTWSRESPLKPFLKLSLGLPGLGIHIRPLAIWLFI
FNVSQQMGGFYLCQPGPPSEKAWQPGWTVNVEG
```

SEQ ID NO:15

```
First core region of clone K (point mutation underlined)
EEPLVVKVEEGDNAVLQCLKGTSDGPTQQLTWSRESPLKPFLKLSLGLPGLGIHMMPLAIWLFI
FNVSQQMGGFYLCQPGPPSEKAWQPGWTVNVEG
```

Fig. 1 (continued)

SEQ ID NO:16

First core region of clone L (point mutation underlined)
EEPLVVKVEEGDNAVLQCLKGTSDGPTQQLTWSRESPLKPFLKLSLGLPGLGIHMTPLAIWLFI
FNVSQQMGGFYLCQPGPPSEKAWQPGWTVNVEG

SEQ ID NO:17

First core region of clone M (point mutation underlined)
EEPLVVKVEEGDNAVLQCLKGTSDGPTQQLTWSRESPLKPFLKLSLGLPGLGIHMTPLAIWLFI
FNVSQQMGGFYLCQPGPPSEKAWQPGWTVNVEG

SEQ ID NO:18

First core region of clone N (point mutation underlined)
EEPLVVKVEEGDNAMLQCLKGTSDGTTQQLTWSRESPLKPFLKLSLGLPGLGIHIRPLAIWLFI
FNVSQQMGGFYLCQPGPPSEKAWQPGWTVNVEG

SEQ ID NO:19

First core region of clone O (point mutation underlined)
EEPLVVKVEEGDNAVLQCLKGTSDGPTQQLTWSRESPLKPFLKLSLGLPGLGIHIRPLAIWLFI
FNVSQQMGGFYLCQPGPPSEKAWQPGWTVNVEG

SEQ ID NO:20

First core region of clone P (point mutation underlined)
EEPLVVKVEEGDNAVLQCLKGTSDGPTQQLTWSRESPLKPFLKLSRGLPGLGIHMRPLAIWLFI
FNVSQQMGGFYLCQPGPPSEKAWQPGWIVNVEG

SEQ ID NO:21

First core region of clone Q (point mutation underlined)
EEPLVVKVEEGDNAVLQCLKGTSDDPTQQLTWSRESPLKPFLKLSLGLPGLGIHIRPLAIWLFI
FNVSQQMGGFYLCQPGPPSEKAWQPGWTVNVEG

SEQ ID NO:22

First core region of clone R (point mutation underlined)
EEPLVVKVEEGDNAVLQCLKGTSDGPTQQLTWSRESPLKPFLKLSLGLPGLGIHIRPLAIWLFI
FNVSQQMGGFYLCQPGPPSEKAWQPGWTVNVEG

SEQ ID NO:23

First core region of clone S (point mutation underlined)
EEPLVVKVEEGDNAVLQCLKGTSDGPTQQLTWSRESPLKPFLKLSLGLPGLGIHMSPLAIWLFV
SNVSQQMGGFYLCQPGPPSEKAWQPGWTVNVEG

Fig. 1 (continued)

SEQ ID NO:24

First core region of clone T (point mutation underlined)
EEPLVVKVEEGDNAVLQCPKGTSDGPTQQLTWSRESPLKPFLKLSLGLPGLGIHMGPLAIRLFI
FNVSQQMGGFYLCQPGPPSEKAWQPGWTVNVEG

SEQ ID NO:25

First core region of clone U (point mutation underlined)
EEPLVVKVEEGDNAVLQCLKGTSDGPTQQLTWSRESPLKPFLKLSLGLPGLGIHIRPLAIRLFI
FNVSQQMGGFYLCQPGPPSEKAWQPGWTVNVEG

SEQ ID NO:26

First core region of clone V (point mutation underlined)
EEPLVVKVEEGDNAVLQCPKGTSDGPTQQLTWSRESPLKPFLKLSLGLPGLGIHIRPLAIWLFI
FNVSQQMGGFYLCQPGPPSEKAWQPGWTVNVEG

SEQ ID NO:27

First core region of clone W (point mutation underlined)
EEPLVVKVEEGDNAVLQCLKGTSDGPTQQLTWSRESPLKPFLKLSLGLPGLGIHIRPLAIWLFI
FNVSQQMGGFYLCQPGPPSEKAWQPGWTVNVEG

SEQ ID NO:28

Second core region of clone A (point mutation underlined)
QDLTMAPGSTLWLSCGVPPDSVSRGPLSWTHVHPKGPKSLLSLELKDDRPARDMWVMETGLLLP
RATAQDAGKYYCHRGNMTMSFHLEITAR

SEQ ID NO:29

Second core region of clone B (point mutation underlined)
QDLTMAPGSTLWLSCGVPPDSVSRGPLSWTHVHPKGPKSLLSLELKDDRPARDMWVMETGLLLP
RATAQDAGTYYCHRGNLTMSFHLEITAR

SEQ ID NO:30

Second core region of clone C (point mutation underlined)
QDLTMAPGSTLWLSCGVPPDSVSRGPLSWTHVHPKGPKSLLSLELKDDRPARDMWVMETGLLLP
RVTAQDAGKYYCRRGNLTMSFHLEITAR

SEQ ID NO:31

Second core region of clone D (point mutation underlined)
QDLTMAPGSTLWLSCGVPPDSVSRGPLSWTHVHPKGPKSLLSLELKDDRPARDMWVMETGLLLP
RVTAQDAGKYYCHRGNLTMSFHLEITAR

Fig. 1 (continued)

SEQ ID NO:32

```
Second core region of clone E (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR
```

SEQ ID NO:33

```
Second core region of clone F (point mutation underlined)
QDLTMAPGSTLWLSCGVPPDSVSRGPLSWTHVHPKGPKSLLSLELKDDRPARDMWVMDTSLLLP
RATAQDAGKYYCHRGNLTMSFHLEITAR
```

SEQ ID NO:34

```
Second core region of clone G (point mutation underlined)
QDLTMAPGSTLWLSCGVPPDSVSRGPLSWTHVHPKGPKSLLSLELNDDRPARDMWVMETGLLLP
RATAQDAGKYYCHRGNLTMSFHLEITAR
```

SEQ ID NO:35

```
Second core region of clone H (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR
```

SEQ ID NO:36

```
Second core region of clone I (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFYLEITAR
```

SEQ ID NO:37

```
Second core region of clone J (point mutation underlined)
QDLTMAPGSTLWLSCGVPPDSVSRGPLSWTHVHPKGPKSLLSLELKDDRPARDMWVMETGLLLP
RVTAQDAGKYYCHRGNLTMSFHLEITAR
```

SEQ ID NO:38

```
Second core region of clone K (point mutation underlined)
QDLTMAPGSTLWLSCGVPPDSVSRGPLSWTHVHPKGPKSLLSLELKDDRPARDMWVMETGLMLP
RATVQDAGKYYCHRGNLTMSFHLEITAR
```

SEQ ID NO:39

```
Second core region of clone L (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR
```

Fig. 1 (continued)

SEQ ID NO:40

Second core region of clone M (point mutation underlined)
QDLTMAPGSTLWLSCGVPPDSVSRGPLSWTHVHPKGPKSLLSLELKDDRPARDMWVMETDLLLP
RATAQDAGKYYCHRGNLTMSFHLEITAR

SEQ ID NO:41

Second core region of clone N (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR

SEQ ID NO:42

Second core region of clone O (point mutation underlined)
QDLTMAPGSTLWLSCGVPPDSVSRGPLSWAHVHPKGPKSLLSLELKDDRPARDMWVMETGLLLP
RATAQDAGKYYCHRGNLTMSFHLEITAR

SEQ ID NO:43

Second core region of clone P (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR

SEQ ID NO:44

Second core region of clone Q (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR

SEQ ID NO:45

Second core region of clone R (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR

SEQ ID NO:46

Second core region of clone S (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEVTAR

SEQ ID NO:47

Second core region of clone T (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR

Fig. 1 (continued)

SEQ ID NO:48

Second core region of clone U (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR

SEQ ID NO:49

Second core region of clone V (point mutation underlined)
QDLTMAPGSTLWLSCGVPPDSVSRGPLSWTHVHPKGPKSLLSLELKDDRPARDMWVMETGLLLP
RATAQDAGKYYCHRGNLTMSFHLEITAR

SEQ ID NO:50

Second core region of clone W (point mutation underlined)
QDLTMAPGSTLWLSCGVPPDSVSRGPLSWTHVHPKGPKSLLSLELMDDRPARDMWVMETGLLLP
RATAQDAGKYYCHRGNLTMSFHLEITAR

SEQ ID NO:51

Third core region of any one of clones A, C-I, K, M-N, P-U, W
(wild-type)
SGELFRWNVSDLGGLGCGLKNRSSEGPSSPSGKLMSPKLYVWAKDRPEIWEGEPPCLPPRDSLN
QSLS

SEQ ID NO:52

Third core region of clone B (point mutation underlined)
SGELFRWNVSDLGGLGCGLKNRSSEGPSSPSGKFMSPKLYVWAKDRPEIWEGEPPCLPPRDSLN
QSLS

SEQ ID NO:53

Third core region of clone J (point mutation underlined)
SGELFRWNVSDLGGLGCGLKNRSSEGPSSPSGKFMSPKLYVWAKDRPEIWEGEPPCLPPRDSLN
QSLS

SEQ ID NO:54

Third core region of clone L (point mutation underlined)
SGELFRWNVSDLGDLGCGLKNRSSEGPSSPSGKLMSPKLYVWAKDRPEIWEGEPPCLPPRDSLN
QSLS

Fig. 1 (continued)

SEQ ID NO:55

Third core region of clone O (point mutation underlined)
SGELFRWNVSD<u>V</u>GGLGCGLKNRSSEGPSSPSGKLMSPKLYVWAKDRPEIWEGEPPCLPPRDSLN
QSLS

SEQ ID NO:56

Third core region of clone V (point mutation underlined)
SGELFRWNVSDLGGLGCGLKNRSSEGPSSPSGKLMSPKLYVWAKDRPEIWEGE<u>S</u>PCLPPRDSLN
QSLS

SEQ ID NO:57

>clone A (SF-01)
PEEPLVVKVEEGDDAVLQCLKGTSDGPNQQLTWSRESPLKPFLKLSLGLPGLGIHMRPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNMTMSFHLEITARP

SEQ ID NO:58

>clone B (SF-02)
PEEPLVVKVEEGDNAVLQCLKGTSDGPTQQLTWSRESPLKPFLKLSLGLPGLGIHMRPLA
IWLSIFNVSQQMGGFYLCQPGPPSEKAWQPGWTVNVEGSGELFRWNVSDLGGLGCGLKNR
SSEGPSSPSGKFMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGTY
YCHRGNLTMSFHLEITARP

SEQ ID NO:59

>clone C (SF-03)
PEEPLVVKVEEGDDAVLQCLKGTSDGPTQQLTWSRESPLKPFLRLSLGLPGLGIHMRPLA
ISLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRVTAQDAGKY
YCRRGNLTMSFHLEITARP

SEQ ID NO:60

>clone D (SF-04)
PEEPLVVKVEEGDNAVLQCLKGTSDGPTQQLTWSRESPLKPFLKLSLGLPGLGIHIRPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRVTAQDAGKY
YCHRGNLTMSFHLEITARP

Fig. 1 (continued)

SEQ ID NO:61

>clone E (SF-05)
PEEPLVVKVEEGDNAVLQCLKGTSDGPTQQLTWSRESPLKPFLKLSLGLPGLGIHVSPLA
IWLFISNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP

SEQ ID NO:62

>clone F
PEEPLVVKVEEGDNAVLQCLKGTSDGPTQQLTWSRESPLKPFLKLSLGLPGLGIHMRPLA
IWLFIFNVSQRMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMDTSLLLPRATAQDAGKY
YCHRGNLTMSFHLEITARP

SEQ ID NO:63

>clone G (SF-06)
PEEPLVVKVEEGDNAVLQCLKGTSDGPTQQLTWSRESPLKPFLKLSLGLPGLGIHIRPLA
IWLFILNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELNDDRPARDMWVMETGLLLPRATAQDAGKY
YCHRGNLTMSFHLEITARP

SEQ ID NO:64

>clone H
PEEPLVVKVEEGDNAVLQCLKGTSDGPTQQLTWSRESPLKPFLKLSLGLPGLGIHMSPLA
IRLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP

SEQ ID NO:65

>clone I
PEEPLVVKVEEGDNAVLQCLKGTSDGPTQQLTWSRESPLKPFLKLSLGLPGLGIHMSPLA
IRLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFYLEITARP

Fig. 1 (continued)

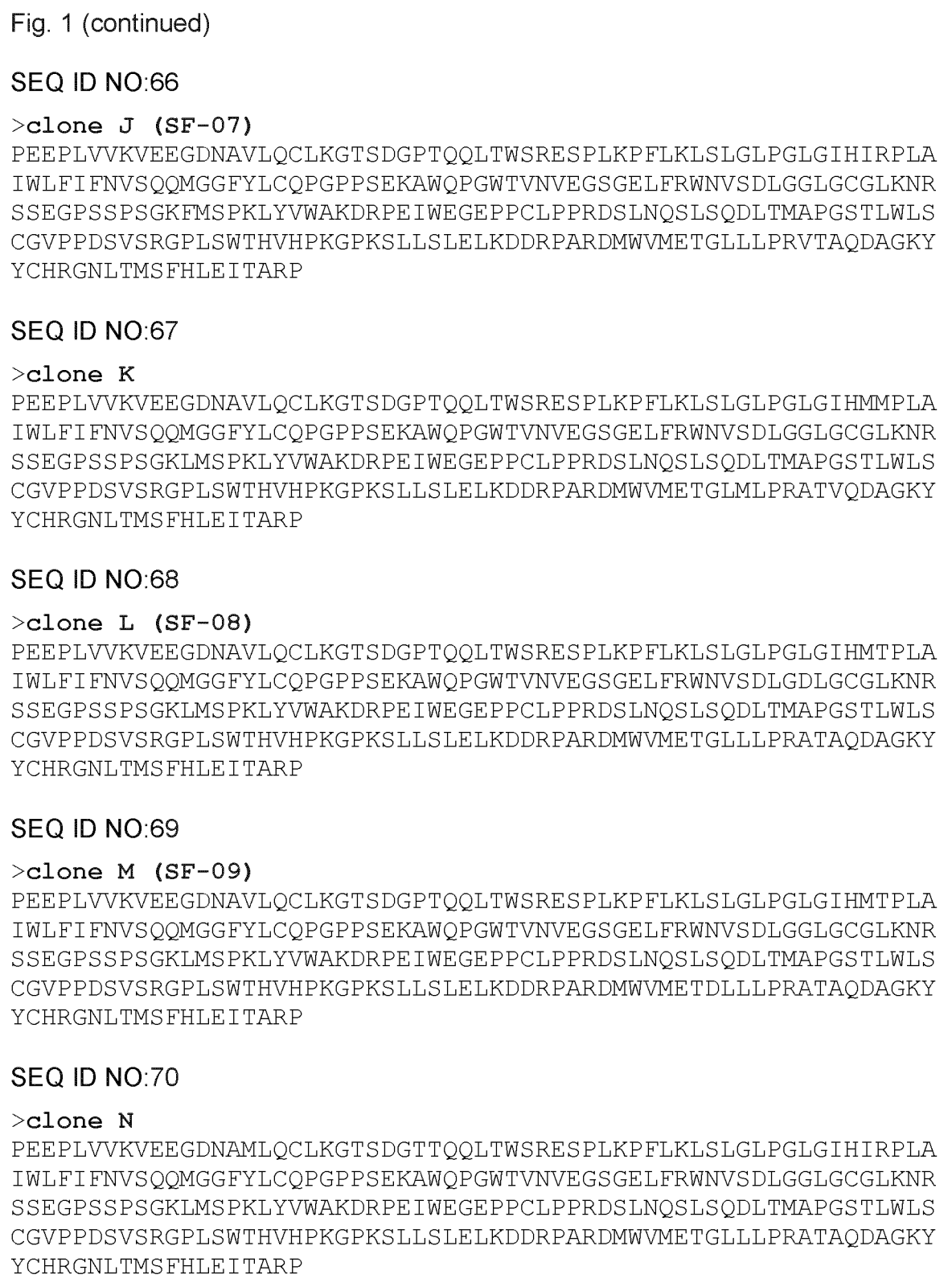

SEQ ID NO:66

>clone J (SF-07)
PEEPLVVKVEEGDNAVLQCLKGTSDGPTQQLTWSRESPLKPFLKLSLGLPGLGIHIRPLA
IWLFIFNVSQQMGGFYLCQPGPPSEKAWQPGWTVNVEGSGELFRWNVSDLGGLGCGLKNR
SSEGPSSPSGKFMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRVTAQDAGKY
YCHRGNLTMSFHLEITARP

SEQ ID NO:67

>clone K
PEEPLVVKVEEGDNAVLQCLKGTSDGPTQQLTWSRESPLKPFLKLSLGLPGLGIHMMPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLMLPRATVQDAGKY
YCHRGNLTMSFHLEITARP

SEQ ID NO:68

>clone L (SF-08)
PEEPLVVKVEEGDNAVLQCLKGTSDGPTQQLTWSRESPLKPFLKLSLGLPGLGIHMTPLA
IWLFIFNVSQQMGGFYLCQPGPPSEKAWQPGWTVNVEGSGELFRWNVSDLGDLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP

SEQ ID NO:69

>clone M (SF-09)
PEEPLVVKVEEGDNAVLQCLKGTSDGPTQQLTWSRESPLKPFLKLSLGLPGLGIHMTPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETDLLLPRATAQDAGKY
YCHRGNLTMSFHLEITARP

SEQ ID NO:70

>clone N
PEEPLVVKVEEGDNAMLQCLKGTSDGTTQQLTWSRESPLKPFLKLSLGLPGLGIHIRPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP

Fig. 1 (continued)

SEQ ID NO:71

>clone O (SF-10)
PEEPLVVKVEEGDNAVLQCLKGTSDGPTQQLTWSRESPLKPFLKLSLGLPGLGIHIRPLA
IWLFIFNVSQQMGGFYLCQPGPPSEKAWQPGWTVNVEGSGELFRWNVSDVGGLGCGLKNR
SSEGPSSPSGKLMSPKLYVWAKDRPEIWEGEPPCLPPRDSLNQSLSQDLTMAPGSTLWLS
CGVPPDSVSRGPLSWAHVHPKGPKSLLSLELKDDRPARDMWVMETGLLLPRATAQDAGKY
YCHRGNLTMSFHLEITARP

SEQ ID NO:72

>clone P
PEEPLVVKVEEGDNAVLQCLKGTSDGPTQQLTWSRESPLKPFLKLSRGLPGLGIHMRPLA
IWLFIFNVSQQMGGFYLCQPGPPSEKAWQPGWIVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP

SEQ ID NO:73

>clone Q (SF-11)
PEEPLVVKVEEGDNAVLQCLKGTSDDPTQQLTWSRESPLKPFLKLSLGLPGLGIHIRPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP

SEQ ID NO:74

>clone R (SF-12)
PEEPLVVKVEEGDNAVLQCLKGTSDGPTQQLTWSRESPLKPFLKLSLGLPGLGIHIRPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP

SEQ ID NO:75

>clone S
PEEPLVVKVEEGDNAVLQCLKGTSDGPTQQLTWSRESPLKPFLKLSLGLPGLGIHMSPLA
IWLFVSNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEVTARP

Fig. 1 (continued)

SEQ ID NO:76

```
>clone T
PEEPLVVKVEEGDNAVLQCPKGTSDGPTQQLTWSRESPLKPFLKLSLGLPGLGIHMGPLA
IRLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP
```

SEQ ID NO:77

```
>clone U (SF-13)
PEEPLVVKVEEGDNAVLQCLKGTSDGPTQQLTWSRESPLKPFLKLSLGLPGLGIHIRPLA
IRLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP
```

SEQ ID NO:78

```
>clone V (SF-14)
PEEPLVVKVEEGDNAVLQCPKGTSDGPTQQLTWSRESPLKPFLKLSLGLPGLGIHIRPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGESPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARP
```

SEQ ID NO:79

```
>clone W (SF-15)
PEEPLVVKVEEGDNAVLQCLKGTSDGPTQQLTWSRESPLKPFLKLSLGLPGLGIHIRPLA
IWLFIFNVSQQMGGFYLCQPGPPSEKAWQPGWTVNVEGSGELFRWNVSDLGGLGCGLKNR
SSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELMDDRPARDMWVMETGLLLPRATAQDAGKY
YCHRGNLTMSFHLEITARP
```

SEQ ID NO:80 (point mutation underlined)
>M56V

```
PEEPLVVKVEEGDNAVLQCLKGTSDGPTQQLTWSRESPLKPFLKLSLGLPGLGIHVRPLAIWLF
IFNVSQQMGGFYLCQPGPPSEKAWQPGWTVNVEGSGELFRWNVSDLGGLGCGLKNRSSEGPSSP
SGKLMSPKLYVWAKDRPEIWEGEPPCLPPRDSLNQSLSQDLTMAPGSTLWLSCGVPPDSVSRGP
LSWTHVHPKGPKSLLSLELKDDRPARDMWVMETGLLLPRATAQDAGKYYCHRGNLTMSFHLEIT
ARP
```

SEQ ID NO:81 (point mutation underlined)
>R57S

```
PEEPLVVKVEEGDNAVLQCLKGTSDGPTQQLTWSRESPLKPFLKLSLGLPGLGIHMSPLAIWLF
IFNVSQQMGGFYLCQPGPPSEKAWQPGWTVNVEGSGELFRWNVSDLGGLGCGLKNRSSEGPSSP
SGKLMSPKLYVWAKDRPEIWEGEPPCLPPRDSLNQSLSQDLTMAPGSTLWLSCGVPPDSVSRGP
LSWTHVHPKGPKSLLSLELKDDRPARDMWVMETGLLLPRATAQDAGKYYCHRGNLTMSFHLEIT
ARP
```

Fig. 1 (continued)

SEQ ID NO:82 (point mutation underlined)
>R57T
PEEPLVVKVEEGDNAVLQCLKGTSDGPTQQLTWSRESPLKPFLKLSLGLPGLGIHM<u>T</u>PLAIWLF
IFNVSQQMGGFYLCQPGPPSEKAWQPGWTVNVEGSGELFRWNVSDLGGLGCGLKNRSSEGPSSP
SGKLMSPKLYVWAKDRPEIWEGEPPCLPPRDSLNQSLSQDLTMAPGSTLWLSCGVPPDSVSRGP
LSWTHVHPKGPKSLLSLELKDDRPARDMWVMETGLLLPRATAQDAGKYYCHRGNLTMSFHLEIT
ARP SEQ ID NO:83
>wtCD19-ECD-E5 with exon 5 (P1-K272)
PEEPLVVKVEEGDNAVLQCLKGTSDGPTQQLTWSRESPLKPFLKLSLGLPGLGIHMRPLAIWLF
IFNVSQQMGGFYLCQPGPPSEKAWQPGWTVNVEGSGELFRWNVSDLGGLGCGLKNRSSEGPSSP
SGKLMSPKLYVWAKDRPEIWEGEPPCLPPRDSLNQSLSQDLTMAPGSTLWLSCGVPPDSVSRGP
LSWTHVHPKGPKSLLSLELKDDRPARDMWVMETGLLLPRATAQDAGKYYCHRGNLTMSFHLEIT
ARPVLWHWLLRTGGWK SEQ ID NO:84 (point mutation underlined)
>N138Q
PEEPLVVKVEEGDNAVLQCLKGTSDGPTQQLTWSRESPLKPFLKLSLGLPGLGIHMRPLAIWLF
IFNVSQQMGGFYLCQPGPPSEKAWQPGWTVNVEGSGELFRWNVSDLGGLGCGLK<u>Q</u>RSSEGPSSP
SGKLMSPKLYVWAKDRPEIWEGEPPCLPPRDSLNQSLSQDLTMAPGSTLWLSCGVPPDSVSRGP
LSWTHVHPKGPKSLLSLELKDDRPARDMWVMETGLLLPRATAQDAGKYYCHRGNLTMSFHLEIT
ARP SEQ ID NO:85
C-terminal amino acid sequence originating from exon 5 of wtCD19-ECD-E5 (i.e.
V260-K272 of SEQ ID NO:83)
VLWHWLLRTGGWK SEQ ID NO:86
sequencing primer pCT-CON2_bw
AAGTACAGTGGGAACAAAG FIG. 2
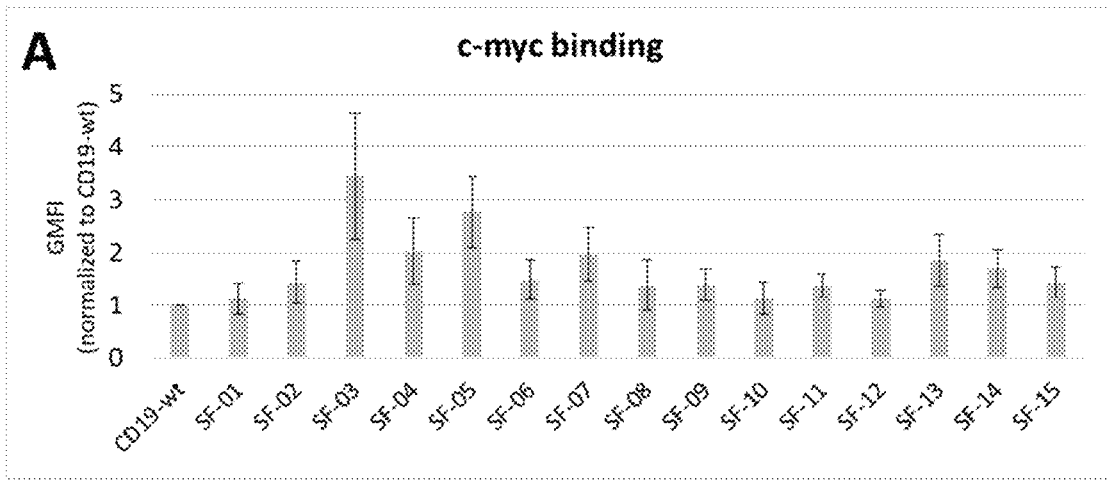
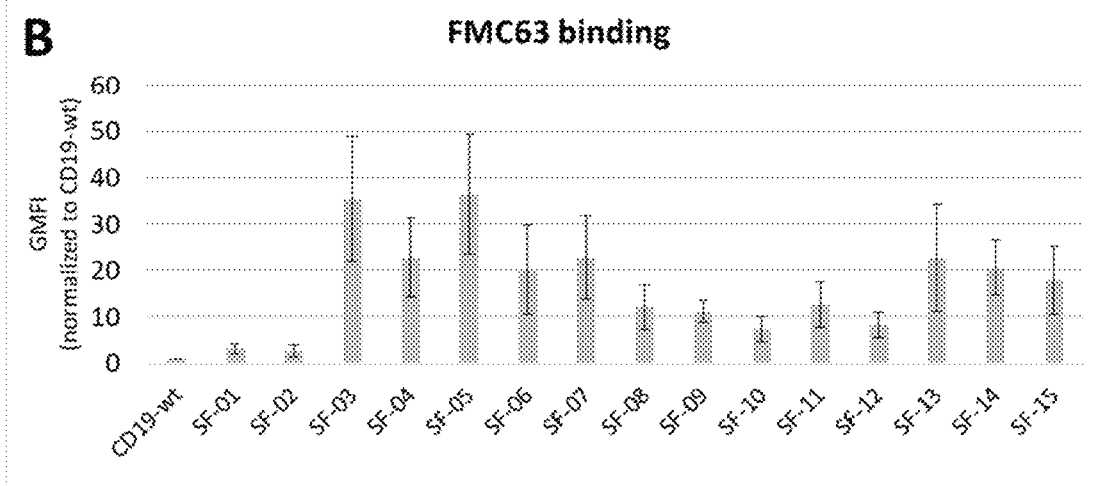
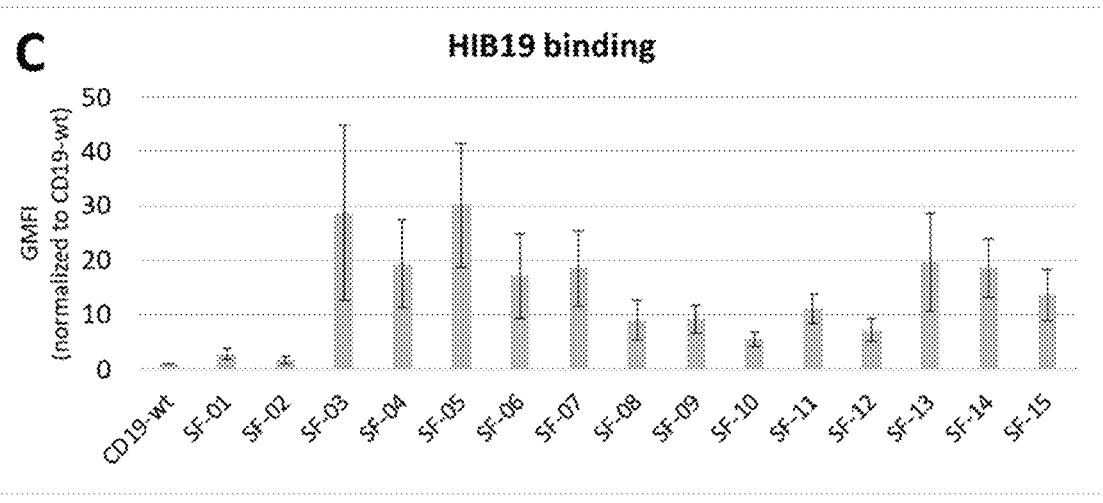

D

A

B

FIG. 10
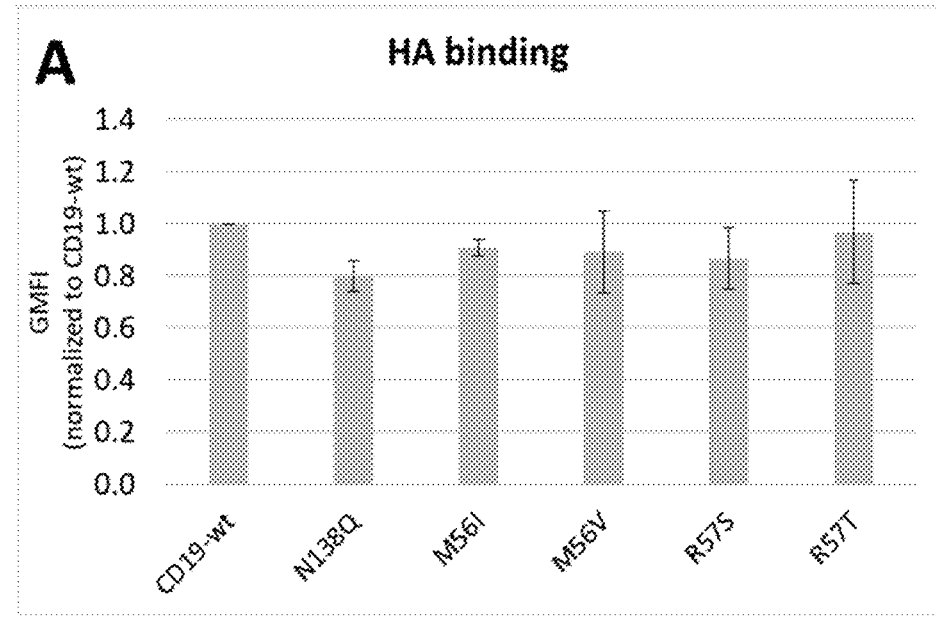
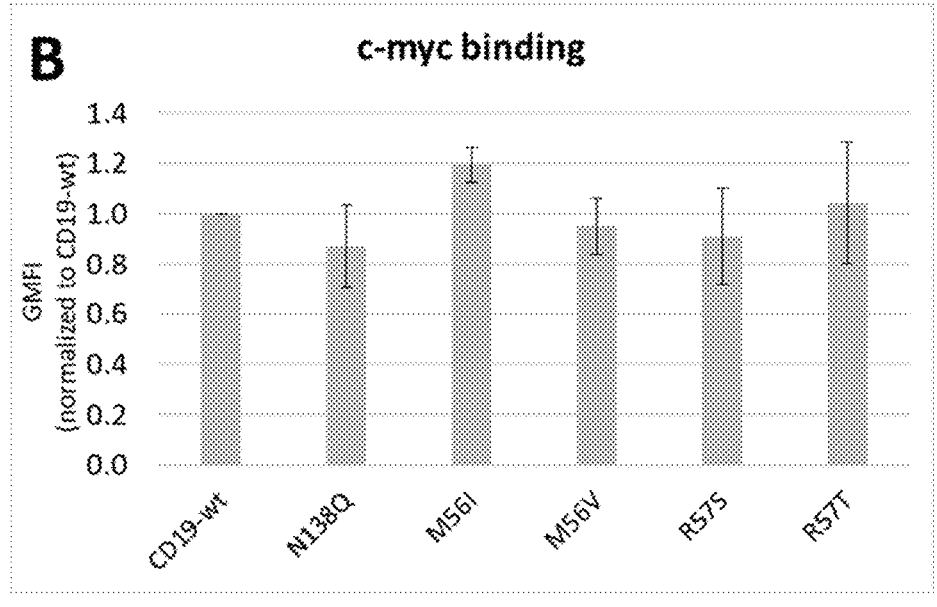

FIG. 10 (continued)
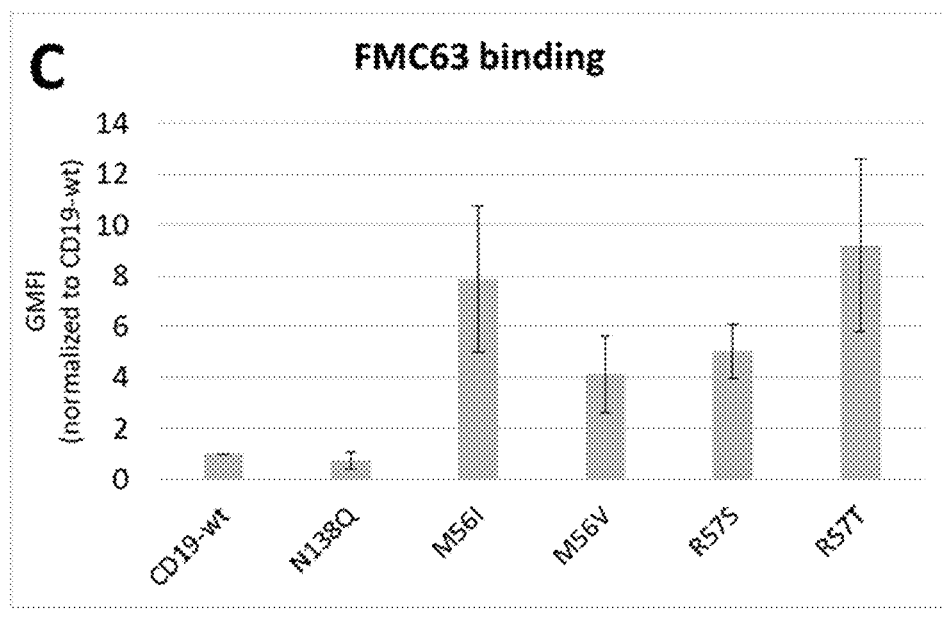
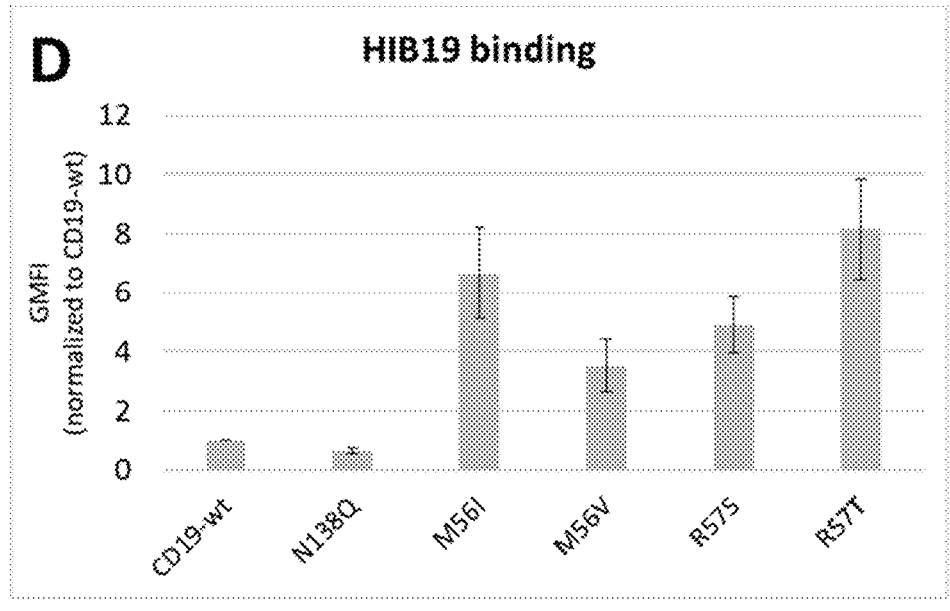

STABILIZED EXTRACELLULAR DOMAIN OF CD19

CROSS-REFERENCE TO RELATED APPLICATIONS

This application is the U.S. national stage of International Patent Application No. PCT/EP2020/053552, filed on Feb. 12, 2020 and entitled STABILIZED EXTRACELLULAR DOMAIN OF CD19, which claims the benefit of priority under 35 U.S.C. § 119 from European Patent Application No. 19160231.7, filed Mar. 1, 2019. The disclosures of the foregoing applications are incorporated herein by reference in their entirety.

SEQUENCE LISTING

The entire content of a Sequence Listing titled "Sequence_Listing.txt," created on Aug. 27, 2021 and having a size of 116,318 bytes, which has been submitted in electronic form in connection with the present application, is hereby incorporated by reference herein in its entirety.

TECHNICAL FIELD

The invention refers to an extracellular domain of CD19 (CD19-ECD) which is stabilized by one or more point mutations in a core region, and methods for producing such CD19-ECD by recombinant expression techniques.

BACKGROUND

CD19 (Cluster of differentiation 19) is classified as a type I transmembrane protein, encompassing a single transmembrane domain, a cytoplasmic C-terminal domain and an extracellular N-terminal domain. This receptor is expressed exclusively on normal and malignant B-cells, which makes it an attractive target for immunotherapy. CD19 interacts with and is stabilized by CD81 and CD21, which together are part of the B-cell coreceptor complex (Li et al., 2017, Immunology letters 183, 86-95). Current clinical CAR-T cell therapies and a considerable amount of preclinical studies target CD19. This fact reflects the need for soluble CD19 protein, which would apply in diagnostics for monitoring of chimeric antigen receptor (CAR)-T cell patients as well as analytics for research and development.

The human CD19 molecule is composed of 15 exons (NCBI Gene ID 930) wherein exons 1-4 encode the extracellular portion of CD19, exon 5 encodes the transmembrane portion of CD19, exons 6-14 encode the cytoplasmic tail and exon 15 encodes the majority of the 3' untranslated region including the poly(A) tail (Zhou et al., Journal of immunology 1991, 147, 1424-1432). However, the extracellular domain of CD19 is classified as difficult-to-express protein, characterized by very low product titers and formation of disulphide-bonded oligomeric aggregates attributed to incorrect protein folding.

A CD19-ECD protein fused to the Fc (crystallizable fragment) of an antibody for enhancement of solubility and expression yield is commercially available. De Oliveira et al. published a CD19-ECD-Fc fusion protein for detection of CARs. The best performing variant encompassed exons 1 to 4 of CD19-ECD (De Oliveira et al., Journal of translational medicine 2013, 11, 23). According to Zhou et al (Journal of immunology 1991, 147, 1424-1432), exons 1 to 4 encompass the native signal peptide until residue 278. The protein was stably expressed as a recombinant protein in HEK293T cells with titers of 16.91 µg/mL determined by using Bicinchoninic acid assay for quantification of total protein concentration. Experiments with anti-CD19 CAR cells using their construct in comparison with commercially available CD19-Fc fusion protein showed a slight increase in detection level (De Oliveira et al., Journal of translational medicine 2013, 11, 23).

Teplyakov et al. published the crystal structure of CD19-ECD in complex with an anti-CD19 Fab antibody B43 (PDB ID 6AL5) at atomic resolution. The CD19-ECD that was used for crystallization encompassed residues 21 to 277 (UniProtKB entry P15391), an 6×His tag for purification and exhibited one point mutation (i.e N138Q) for knocking out one of the N-glycosylation sites. The protein was expressed by Tni PRO insect cells in low amounts, resulting in only 14 mg protein per 40 L cell supernatant yielded after affinity and size-exclusion chromatography. Interestingly, the β-sandwich structure reveals a unique topology based on a swapped arrangement of two Ig folds. The N138Q mutation is located in a loop region aside from the Ig folds that are determining the protein structure (Teplyakov et al., 2018, Proteins 86, 495-500).

WO2018161017A1 discloses a human CD19 antigen lacking exon 2 and comprising certain epitopes for producing anti-CD19 binders and compositions used for immunotherapy.

WO2018156802A1 (alike WO2017075537A1) discloses compositions comprising cellular therapeutics for treating cancer, particularly using chimeric antigen receptors (CAR). Reference is made to expression constructs encoding a fusion of an antibody to a human antigen e.g., an scFv-CD19 fusion protein to provide CAR-T cells that bind CD19. According to the disclosure, the full-length CD19, the full-length CD19 extracellular domain, CD19 loops, fragments or variants, can be selected for use in respective constructs. A specific example refers to yeast displayed extracellular domain of human wild-type CD19 (aa 1-272) and a respective library displayed on the yeast surface.

Klesmith et al. (Mol. Pharmaceutics 2019, 16, 8, 3544-3558) describe retargeting CD19 CAR-T cells via CD19 fusion proteins engineered for improved protease resistance and to improve such fusion protein expression.

Satiro N de Oliveira et al. (Journal of Translational Medicine 2013, vol. 11, no. 1, pp 23) describe a CD19/Fc fusion protein for detection of anti-CD19 chimeric receptors. Certain fusion proteins consisting of the human CD19 extracellular domains (exons 1-3 or exons1-4) and the Fc region of human IgG1 are disclosed.

Traxlmayr et al. (Protein Engineering Design and Selection 2012, vol. 26, no. 4, pp 255-265) describe directed evolution of a Her2/neu binding IgG1-Fc using yeast display.

Zhou et al. (The Journal of Immunology 1991, pp 1424-1432) describe the structure and domain organization of the CD19 antigen, its cytoplasmic and extracellular domains (exons 1-5).

WO2017055328A1 discloses anti-human CD19 antibodies and sequences of the human CD19 ectodomain and the cynomolgous CD19 ectodomain.

The amino acid sequence of marmoset CD19 protein (Callithrix jacchus) has been provided under Uniprot: Q3LRP3.

Another approach for detection of CAR expressing cells are anti-idiotypic antibodies. Currently, the CD19 binding moiety of CARs is most often derived from the mouse monoclonal antibody (mAb) (clone FMC63) (Zola et al., 1991, Immunology and Cell Biology 69, 411-422). The anti-idiotypic mAb—no. 136.20.1—was developed by immunization of mice with L cells displaying the scFv of the anti-CD19 antibody (clone FMC63) (Jena et al., 2013, PloS one 8, e57838). However, the application of this anti-idiotypic mAb is limited to CARs equipped with the scFv of the anti-CD19 antibody (clone FMC63). Considering the large amount of existing anti-CD19 mAbs, especially fully-human anti-CD19 mAbs, such an anti-idiotype mAb is of only limited use.

SUMMARY OF THE INVENTION

It is the object to stabilize CD19-ECD to provide a stable protein and to improve its production by a recombinant host cell. It is a further object to provide a stable CD19-ECD preparation for use in an assay in particular to test its reaction with specific CARs or CD19-specific antibodies or antibody fragments, especially with CARs expressed on immune cells, or for medical use.

The object is solved by the subject matter as claimed.

According to the invention, there is provided a stabilized CD19-ECD which comprises at least 90%, or at least 95% sequence identity to SEQ ID NO:1, a first core region at positions 2-98 of SEQ ID NO:1, a second core region at positions 167-258 of SEQ ID NO:1, a third core region at positions 99-166 of SEQ ID NO:1, and at least one stabilizing point mutation at an amino acid position within said first and/or second and/or third core regions, wherein the CD19-ECD has an increased thermal stability compared to CD19-ECD which consists of an amino acid sequence identified as SEQ ID NO:1.

Specifically, the stabilized CD19-ECD is an isolated protein that is provided as a soluble protein, thus, not bound to a cell surface. Specifically, the CD19-ECD described herein is devoid of a transmembrane domain.

Specifically, the CD19-ECD described herein comprises at least any one of 90%, 91%, 92%, 93%, 94%, 95%, 96%, 97%, 98% or 99% sequence identity to SEQ ID NO:1. Specifically, sequence identity is determined as further disclosed herein, for example, when comparing with the full-length sequence, or the full-length sequence comprising each of the first, second and third core sequences, respectively; or when comparing with a fragment of any of the foregoing which has a length comprising at least 80%, 85%, 90% or 95% of each of the first, second and third core sequences, respectively.

Specifically, said first core region has a certain sequence similarity to the region within positions 2-98 of SEQ ID NO:1.

Specifically, said second core region has a certain sequence similarity to the region within positions 167-258 of SEQ ID NO:1.

Specifically, said third core region has a certain sequence similarity to the region within positions 99-166 of SEQ ID NO:1.

Specifically, any one, two or three of said first, second and third core regions comprise or consist of an amino acid sequence which has at least any one of 80%, 85%, 90%, 91%, 92%, 93%, 94%, 95%, 96%, 97%, 98% or 99% sequence identity to SEQ ID NO:2, SEQ ID NO:3 and SEQ ID NO:4, respectively. It is understood that one or two of the core region sequences may be 100% identical to the respective wild-type sequence, or the respective core region of SEQ ID NO:1, however, at least one of the core regions comprises said at least one stabilizing point mutations as further described herein, thus has a sequence identity of less than 100%.

Specifically, the CD19-ECD described herein comprises a C-terminal amino acid sequence consisting of 13 contiguous amino acids which comprises less than 9, 8, or 6 hydrophobic amino acids, such as valine, leucine, tryptophan or glycine. Specifically, such C-terminal amino acid sequence of the CD19-ECD described herein consists of 13 contiguous amino acids and is different from SEQ ID NO:85.

Specifically, the CD19-ECD described herein has an increased thermal stability compared to a wild-type human CD19-ECD, in particular a wild-type human CD19-ECD which comprises or consists of an amino acid sequence identified as SEQ ID NO:1. Such wild-type human CD19-ECD does not comprise SEQ ID NO:85 as a C-terminal amino acid sequence.

Specifically, the wild-type human CD19-ECD as described herein does not comprise a C-terminal amino acid sequence originating from exon 5 of wtCD19.

Specifically, the wild-type human CD19-ECD as described herein does not comprise or consist of an amino acid sequence identified as SEQ ID NO:83 (wtCD19-ECD-E5 with exon 5 (P1-K272)).

Specifically, the wild-type human CD19-ECD as described herein consists of an amino acid sequence identified as SEQ ID NO:1.

Specifically, SEQ ID NO:2 identifies the first core region within positions 2-98 of SEQ ID NO:1. Specifically, said first core region comprises or consists of at least two partial domains, namely a part of "domain 1" and a part of "domain 2", each part typically being composed of four beta-strands. Positions 2-50 belong to domain 1, positions 51-98 belong to the domain 2. The part of domain 2 within said first core region typically contains a potential N-glycosylation site at position 67.

Specifically, said at least one stabilizing point mutation is at an amino acid position within domain 2 of said first core region.

Specifically, SEQ ID NO:3 identifies the second core region within positions 167-258 of SEQ ID NO:1. Specifically, said second core region comprises or consists of at least two partial domains, namely a part of "domain 1" and a part of "domain 2", each part typically being composed of four beta-strands. Positions 167-215 belong to domain 2, positions 216-258 belong to domain 1. The part of domain 1 within said second core region typically contains a potential N-glycosylation site at position 246.

Specifically, SEQ ID NO:4 identifies the third core region within positions 99-166 of SEQ ID NO:1. Specifically, said third core region typically comprises or consists of three beta-strands and adjoining loop regions, which may be partially unstructured or flexible. Furthermore, said third core region typically contains three potential N-glycosylation sites at positions 106, 119 and 162.

Specifically, the CD19-ECD described herein is of human origin, and preferably prepared by mutagenesis of naturally occurring (i.e., wild-type, wt) CD19-ECD, in particular wtCD19-ECD (herein also referred to as CD19-ECDwt, in the Examples described herein also referred to as CD19-wt) which consists of an amino acid sequence identified as SEQ ID NO:1.

Specifically, a mutagenesis method is used to introduce said at least one (one or more) stabilizing point mutations, thereby increasing the thermal stability compared to the CD19-ECD prior to such mutagenesis to achieve stabilization of the protein.

According to a specific aspect, the CD19-ECD described herein has a native conformation as determined by comprising one or more epitopes recognized by at least one conformation specific antibody.

An anti-CD19 antibody is herein understood to be conformation specific, if specifically recognizing a non-linear, thus conformational epitope that is present in naturally occurring wtCD19-ECD.

Specifically, the conformational epitope is shared by, or present in both, the wtCD19-ECD and the CD19-ECD mutant described herein.

Such conformation specific anti-CD19 antibody is preferably used in determining the stability of the CD19-ECD described herein, establishing the native conformation and structure of the CD19-ECD mutant.

According to a specific aspect, a CD19-ECD mutant described herein which is recognized by a conformation specific anti-CD19 antibody (herein also referred to as "conformationally recognized"), can be produced as a recombinant protein at high yields. Specifically, a preparation of the conformationally recognized recombinant CD19-ECD mutant described herein comprises the CD19-ECD mutant as a monomeric protein, e.g., wherein at least 20% of the CD19-ECD molecules are monomeric.

Specifically, the CD19-ECD described herein has a half maximum irreversible denaturation temperature ($T_{1/2}$ in ° C.) which is increased compared to the half maximum irreversible denaturation temperature ($T_{1/2}$ in ° C.) of the reference CD19-ECD (in particular wtCD19-ECD). The increase in $T_{1/2}$ is herein also referred to as a "positive shift" and typically amounts to at least any one of 1.5° C., 2, 3, 4, 5, 6, 7, 8, 9, 10° C., or up to a maximum of any one of 20° C., 19° C., 18° C., 17° C., 16° C., 15° C., 14° C., 13° C., 12° C., 11° C., or 10° C.

Specifically, the increase in $T_{1/2}$ is at least 3%, 4% or 5%.

Specifically, thermal stability is determined by a standard assay employing flow cytometric methods and analysis, e.g. to determine the half maximum irreversible denaturation temperature ($T_{1/2}$ in ° C.) calculated from flow cytometric binding analysis of cell surface bound CD19-ECD e.g., yeast expressed CD19-ECD (wtCD19-ECD or CD19-ECD mutant), with an anti-CD19 antibody e.g., a conformation specific anti-CD19 antibody, after heat treatment of the cells. For such binding analysis, anti-CD19 antibodies may be used which specifically recognize a conformational epitope of the CD19-ECD that is present in human wtCD19-ECD. Specifically, fluorochrome-conjugated antibodies (e.g., Alexa Fluor®488 conjugated antibodies) may be used for use in flow cytometry. An exemplary conformation specific anti-CD19 antibody is selected from the group consisting of clone HIB19 (commercially available from BioLegend, San Diego, CA), clone FMC63 (commercially available from Absolute Antibody Ltd, Oxford, UK) and clone SJ25C1 (commercially available from BioLegend, San Diego, CA). The skilled artisan will know that these conformation specific antibodies can either be directly labeled (e.g. with a fluorescence dye) or can be detected with secondary (and subsequently even tertiary or quaternary) detection reagents such as fluorescently labeled antibodies or streptavidin.

According to a specific example, the conformation specific anti-CD19 antibody (clone HIB19) is used to identify and/or determine the CD19-ECD described herein.

Typically, wtCD19-ECD is highly unstable when present in solution, i.e. without being cell surface bound and can hardly be analyzed by flow cytometric analysis. In particular, a recombinant wtCD19-ECD cannot be provided as a monomeric protein because of such instability. Consequently, wtCD19-ECD when used as a reference for the purpose of determining the thermal stability is prepared the same way and analyzed by the same method as the CD19-ECD mutant.

According to a specifically preferred embodiment, both, the wtCD19-ECD and the CD19-ECD mutant, are expressed on the surface of a recombinant host cell, such as a yeast capable of displaying a recombinant protein at the outer surface, and their binding to a conformation specific antibody is analyzed by flow cytometry, optionally following or during heat treatment. An exemplary test system is described in the examples section below.

Specifically, the CD19-ECD consisting of the amino acid sequence identified as SEQ ID NO:1 can be used as the reference material.

Specifically, in the thermal stability assay, both, the reference CD19-ECD and the stabilized CD19-ECD mutants, are recombinantly expressed on the surface of yeast cells e.g., using a suitable yeast display technology.

According to a specific embodiment, the thermal stability of a CD19-ECD mutant described herein is compared to the thermal stability of a CD19-ECD reference material to determine an increase in thermal stability, employing the same yeast display method and expression technology for preparing the material, heat treatment for determining the thermal stability, and analysis as a conformationally recognized CD19-ECD in each case. According to a specific aspect, the thermal stability is determined by measuring the binding of a conformation specific anti-CD19 antibody to the CD19-ECD, thereby determining the native conformation of the protein following heat treatment. An increase of thermal stability of the CD19-ECD mutant described herein as compared to the reference CD19-ECD is typically determined by the higher temperature ($T_{1/2}$ in ° C.) which can be applied to the CD19-ECD mutant without losing the native conformation as compared to the reference CD19-ECD.

According to a specific aspect, the CD19-ECD described herein comprises one or more stabilizing mutations, of which at least one is located at an amino acid position selected from the group consisting of M56, R57, N14, V16, L20, G26, P27, T28, K44, L47, W62, F64, I65, F66, Q71, T93, L110, G112, L132, P152, T196, K212, E224, G226, L228, A232, A234, K239, H243, L247, H252 and I255, wherein numbering is according to SEQ ID NO:1.

According to a specific embodiment, the amino acid position is selected from the group consisting of M56, R57, N14, L20, G26, T28, K44, W62, F64, F66, L110, G112, L132, P152, T196, K212, G226, A232, K239, H243, and L247.

According to a specific embodiment, the amino acid position is selected from the group consisting of M56, R57, W62, F66, G112, and A232, preferably any one of M56 or R57.

Specifically, said amino acid position is in domain 2 of said first core region.

According to a specific aspect, said at least one stabilizing point mutation is an amino acid substitution selected from the group consisting of M56I, M56V, R57G, R57M, R57S, R57T, N14D, V16M, L20P, G26D, P27T, T28N, K44R, L47R, W62R, W62S, F64S, I65V, F66L, F66S, Q71R, T93I, L110V, G112D, L132F, P152S, T196A, K212M, K212N, E224D, G226D, G226S, L228M, A232V, A234V, K239T, H243R, L247M, H252Y and I255V, or which is a conservative amino acid substitution of any of the foregoing.

According to a specific embodiment, said at least one stabilizing point mutation is an amino acid substitution selected from the group consisting of M56I, M56V, R57S, R57T, N14D, L20P, G26D, T28N, K44R, W62R, W62S, F64S, F66L, F66S, L110V, G112D, L132F, P152S, T196A, K212M, K212N, G226D, A232V, K239T, H243R, and L247M, or which is a conservative amino acid substitution of any of the foregoing.

According to a specific embodiment, said at least one stabilizing point mutation is an amino acid substitution selected from the group consisting of M561, M56V, R57S, R57T, W62R, F66S, G112D, and A232V, or which is a conservative amino acid substitution of any of the foregoing.

A conservative substitution is specifically understood as an amino acid replacement that changes a given amino acid to a different amino acid with similar biochemical properties (e.g., charge, hydrophobicity and size) to the stabilizing point mutations listed above, in particular as further described herein.

Specifically preferred conservative substitutions are indicated in the table below.

TABLE 1

| Position No. | Naturally occuring aa in SEQ ID NO:1 | Mutation | Conservative substitutions and selection of preferred aa, if any. |
|---|---|---|---|
| 14 | N | D | E, Q, L; preferably E |
| 16 | V | M | I, L, Q, K; preferably I, or L |
| 20 | L | P | — |
| 26 | G | D | E, Q, L, N; preferably E, or N |
| 27 | P | T | S, A, V, G; preferably S, or V |
| 28 | T | N | D, Q, S; preferably D, or Q |
| 44 | K | R | H, Q, N; preferably H, or Q |
| 47 | L | R | K, H, Q, N; preferably K, or H |
| 56 | M | I, V | L, A, F; preferably L, or A |
| 57 | R | G, M, S, T | A, V, I, L, N, Q, F; preferably A, V, or N |
| 62 | W | R, S | K, H, T, A, G, V, Q; preferably K, T, or A |
| 64 | F | S | T, A, V, N, G; preferably T, or A |
| 65 | I | V | L, A, G, T; preferably T, or A |
| 66 | F | L, S | A, V, I, M, T, G, N, Q;; preferably T, I, or V |
| 71 | Q | R | K, H, N; preferably K, or H |
| 93 | T | I | L, V, A, F, M; preferably L, or V |
| 110 | L | V | I, A, G, T; preferably I, or T |
| 112 | G | D | E, Q, L, N; preferably E, or N |
| 132 | L | F | W, Y, H, M; preferably W, or Y |
| 152 | P | S | T, A, V, N, G; preferably A, or T |
| 196 | T | A | S, G, V; preferably S, or G |
| 212 | K | M, N | Q, D, E, L, I, V, T; preferably Q, L, or I |
| 224 | E | D | N, Q, T; preferably N, or Q |
| 226 | G | D, S | E, Q, L, N, T, A; preferably E, N, or T |
| 228 | L | M | I, V, Q, K; preferably I, or V |
| 232 | A | V | I, L, F, W, M, T; preferably I, or L |
| 234 | A | V | I, L, F, W, M, T; preferably I, or L |
| 239 | K | T | S, A, V, G; preferably S, or V |
| 243 | H | R | K, Q, N; preferably K, or Q |
| 247 | L | M | I, V, Q, K; preferably I, or V |
| 252 | H | Y | F, W, T; preferably F, or W |
| 255 | I | V | L, A, G, T; preferably T, or A | amino acid substitution at certain positions in SEQ ID NO:1, and selection of conservative alternative amino acid substitutions.

According to a specific aspect, the CD19-ECD described herein comprises at least one stabilizing point mutation in any of the first, second or third core regions, wherein the number of stabilizing point mutations, or the total number of (any kind of) point mutations (wherein at least one is a stabilizing mutation), is:

a) 0, or at least 1, 2, or 3, up to 16 point mutations in said first core region; and/or b) 0, or at least 1, or 2, up to 12 point mutations in said second core region; and/or c) 0, or at least 1, up to 4 point mutations in said third core region.

According to a specific aspect, within each of said first, second and third core regions, or within two or all three of said first, second and third core regions (taken together), the total number of point mutations (including any kind of point mutations such as amino acid substitutions, insertions and deletions), is limited, in particular not more than any one of 25, 20, 19, 18, 17, 16, 15, 14, 13, 12, 11, 10, 9, 8, 7, 6, or 5.

Specifically, the point mutations comprised in the CD19-ECD described herein are single amino acid substitutions, preferably wherein the number of amino acid substitutions is less than 25, 20, 19, 18, 17, 16, 15, 14, 13, 12, 11, 10, 9, 8, 7, 6, or 5.

Specifically, the number of point mutations comprised in the CD19-ECD described herein is only one (also referred to as "single" point mutation), e.g. at a position in domain 2, such as at position M56 or R57, preferably any one of M561, M56V, R57G, R57M, R57S, R57T.

It is well understood that the total number of stabilizing point mutations, or the total number of any kind of point mutations, in all three core regions (taken together) is not zero. Specifically, the CD19-ECD described herein has a sequence identity of less than 100% compared to SEQ ID NO:1.

Specifically, within said first core region, the total number of stabilizing point mutations, or the total number of (any kind of) point mutations, is any one of 0, 1, 2, or 3.

Specifically, within said second core region, the total number of stabilizing point mutations, or the total number of (any kind of) point mutations, is any one of 0, 1, 2, or 3.

Specifically, within said third core region, the total number of stabilizing point mutations, or the total number of (any kind of) point mutations, is any one of 0, 1, or 2.

Specifically, within both, said first and second core regions, the total number of stabilizing point mutations, or the total number of (any kind of) point mutations, is any one of 0, 1, 2, 3, 4, 5, or 6.

Specifically, within all three of said first, second, and third core regions, the total number of stabilizing point mutations, or the total number of (any kind of) point mutations (wherein at least one is a stabilizing mutation), is any one of 1, 2, 3, 4, 5, or 6.

Specifically, at least one of the point mutations is positioned in said first core region, preferably in domain 2.

Specifically, the CD19-ECD described herein comprises at least one point mutation in domain 2 of said first core region, and at least another point mutation in another domain of the CD19-ECD, such as in domain 1.

Specifically, the number of point mutations in the CD19-ECD described herein is at least 2, 3, 4, or 5, wherein at least one of the point mutations is positioned in said first core region, preferably in domain 2, e.g. at position M56 or R57, such as any one of M561, M56V, R57G, R57M, R57S, R57T.

According to specific embodiments, a) the first core region is any one of SEQ ID NO:5-27; and/or b) the second core region is any one of SEQ ID NO:28-50; and/or c) the third core region is any one of SEQ ID NO:51-56.

Specifically preferred combinations are selected from the group consisting of group members i) to xxiii), wherein:

i) the first core region is comprised of SEQ ID NO:5, and the second core region is comprised of SEQ ID NO:28;

ii) the first core region is comprised of SEQ ID NO:6, and the second core region is comprised of SEQ ID NO:29;

iii) the first core region is comprised of SEQ ID NO:7, and the second core region is comprised of SEQ ID NO:30;

iv) the first core region is comprised of SEQ ID NO:8, and the second core region is comprised of SEQ ID NO:31;

v) the first core region is comprised of SEQ ID NO:9, and the second core region is comprised of SEQ ID NO:32;

vi) the first core region is comprised of SEQ ID NO:10, and the second core region is comprised of SEQ ID NO:33;

vii) the first core region is comprised of SEQ ID NO:11, and the second core region is comprised of SEQ ID NO:34;

viii) the first core region is comprised of SEQ ID NO:12, and the second core region is comprised of SEQ ID NO:35;

ix) the first core region is comprised of SEQ ID NO:13, and the second core region is comprised of SEQ ID NO:36;

x) the first core region is comprised of SEQ ID NO:14, and the second core region is comprised of SEQ ID NO:37;

xi) the first core region is comprised of SEQ ID NO:15, and the second core region is comprised of SEQ ID NO:38;

xii) the first core region is comprised of SEQ ID NO:16, and the second core region is comprised of SEQ ID NO:39;

xiii) the first core region is comprised of SEQ ID NO:17, and the second core region is comprised of SEQ ID NO:40;

xiv) the first core region is comprised of SEQ ID NO:18, and the second core region is comprised of SEQ ID NO:41;

xv) the first core region is comprised of SEQ ID NO:19, and the second core region is comprised of SEQ ID NO:42;

xvi) the first core region is comprised of SEQ ID NO:20, and the second core region is comprised of SEQ ID NO:43;

xvii) the first core region is comprised of SEQ ID NO:21, and the second core region is comprised of SEQ ID NO:44;

xviii) the first core region is comprised of SEQ ID NO:22, and the second core region is comprised of SEQ ID NO:45;

xix) the first core region is comprised of SEQ ID NO:23, and the second core region is comprised of SEQ ID NO:46;

xx) the first core region is comprised of SEQ ID NO:24, and the second core region is comprised of SEQ ID NO:47;

xxi) the first core region is comprised of SEQ ID NO:25, and the second core region is comprised of SEQ ID NO:48;

xxii) the first core region is comprised of SEQ ID NO:26, and the second core region is comprised of SEQ ID NO:49;

xxiii) the first core region is comprised of SEQ ID NO:27, and the second core region is comprised of SEQ ID NO:50.

Specifically preferred combinations are selected from the group consisting of group members i) to xxiii), wherein:

i) the first core region is comprised of SEQ ID NO:5, the second core region is comprised of SEQ ID NO:28, and the third core region is comprised of SEQ ID NO:4;

ii) the first core region is comprised of SEQ ID NO:6, the second core region is comprised of SEQ ID NO:29, and the third core region is comprised of SEQ ID NO:52;

iii) the first core region is comprised of SEQ ID NO:7, the second core region is comprised of SEQ ID NO:30, and the third core region is comprised of SEQ ID NO:4;

iv) the first core region is comprised of SEQ ID NO:8, the second core region is comprised of SEQ ID NO:31, and the third core region is comprised of SEQ ID NO:4;

v) the first core region is comprised of SEQ ID NO:9, the second core region is comprised of SEQ ID NO:32, and the third core region is comprised of SEQ ID NO:4;

vi) the first core region is comprised of SEQ ID NO:10, the second core region is comprised of SEQ ID NO:33, and the third core region is comprised of SEQ ID NO:4;

vii) the first core region is comprised of SEQ ID NO:11, the second core region is comprised of SEQ ID NO:34, and the third core region is comprised of SEQ ID NO:4;

viii) the first core region is comprised of SEQ ID NO:12, the second core region is comprised of SEQ ID NO:35, and the third core region is comprised of SEQ ID NO:4;

ix) the first core region is comprised of SEQ ID NO:13, the second core region is comprised of SEQ ID NO:36, and the third core region is comprised of SEQ ID NO:4;

x) the first core region is comprised of SEQ ID NO:14, the second core region is comprised of SEQ ID NO:37, and the third core region is comprised of SEQ ID NO:53;

xi) the first core region is comprised of SEQ ID NO:15, the second core region is comprised of SEQ ID NO:38, and the third core region is comprised of SEQ ID NO:4;

xii) the first core region is comprised of SEQ ID NO:16, the second core region is comprised of SEQ ID NO:39, and the third core region is comprised of SEQ ID NO:54;

xiii) the first core region is comprised of SEQ ID NO:17, the second core region is comprised of SEQ ID NO:40, and the third core region is comprised of SEQ ID NO:4;

xiv) the first core region is comprised of SEQ ID NO:18, the second core region is comprised of SEQ ID NO:41, and the third core region is comprised of SEQ ID NO:4;

xv) the first core region is comprised of SEQ ID NO:19, the second core region is comprised of SEQ ID NO:42, and the third core region is comprised of SEQ ID NO:55;

xvi) the first core region is comprised of SEQ ID NO:20, the second core region is comprised of SEQ ID NO:43, and the third core region is comprised of SEQ ID NO:4;

xvii) the first core region is comprised of SEQ ID NO:21, the second core region is comprised of SEQ ID NO:44, and the third core region is comprised of SEQ ID NO:4;

xviii) the first core region is comprised of SEQ ID NO:22, the second core region is comprised of SEQ ID NO:45, and the third core region is comprised of SEQ ID NO:4;

xix) the first core region is comprised of SEQ ID NO:23, the second core region is comprised of SEQ ID NO:46, and the third core region is comprised of SEQ ID NO:4;

xx) the first core region is comprised of SEQ ID NO:24, the second core region is comprised of SEQ ID NO:47, and the third core region is comprised of SEQ ID NO:4;

xxi) the first core region is comprised of SEQ ID NO:25, the second core region is comprised of SEQ ID NO:48, and the third core region is comprised of SEQ ID NO:4;

xxii) the first core region is comprised of SEQ ID NO:26, the second core region is comprised of SEQ ID NO:49, and the third core region is comprised of SEQ ID NO:56;

xxiii) the first core region is comprised of SEQ ID NO:27, the second core region is comprised of SEQ ID NO:50, and the third core region is comprised of SEQ ID NO:4.

According to a specific aspect, the CD19-ECD described herein comprises or consists of an amino acid sequence selected from the group consisting of SEQ ID NO:57-82, or 57-79.

Specifically, the CD19-ECD described herein does not comprise the amino acid substitution N138Q.

Specifically, the CD19-ECD described herein does not comprise or consist of the amino acid sequence identified as SEQ ID NO:84.

According to a specific aspect, the CD19-ECD described herein comprises one or more of the following features, in particular one, two, three or four of the following features:

a) an asparagine at one or more of the following positions of SEQ ID NO:1: N67, N106, N119, N162 and N246; in particular 1, 2, 3, 4, or 5 N-glycosylation sites, selected from those located on positions N67, N106, N119, N162, and N246;

b) a cysteine
   i. at positions C19 and C242; and/or
   ii. at positions C78 and C181; and/or
   iii. at positions C115 and C154;

in particular one, two or three intramolecular disulfide bonds, selected from those
   i. linking C19 to C242; and/or
   ii. linking C78 to C181; and/or
   iii. linking C115 to C154;

c) an epitope recognized by an antibody, in particular a conformation specific anti-CD19 antibody which also specifically recognizes wild-type human CD19 (wtCD19-ECD) expressed on the surface of native human B-cells, e.g. human B cells expressing CD19, such as B cells present in a blood sample of a human subject;

d) a C-terminal amino acid sequence consisting of 13 consecutive (contiguous) amino acids which
i) comprises less than 9, 8, or 7 hydrophobic amino acids, such as valine, leucine, tryptophan, or glycine; and/or
ii) does not comprise an amino acid sequence of at least 7, 8, 9, 10, 11, 12, or 13 amino acids length that originates from exon 5 of wtCD19 (SEQ ID NO:85); and/or
iii) is different from SEQ ID NO:85.

According to a specific embodiment, the CD19-ECD described herein is provided as an antigen e.g. in an immunogenic preparation, which may be used for preparing immunoreagents such as anti-CD19 antibodies or CD19 specific immune cells.

According to a specific aspect, the CD19-ECD described herein is fused to a heterologous protein, peptide or amino acid, thus, provided as a fusion protein.

According to another specific aspect, the CD19-ECD described herein is bound to a solid phase, including solid carriers, or a semi-liquid or liquid carrier, such as beads.

According to a specific aspect, the CD19-ECD described herein is bound to a detectable moiety, which may be directly or indirectly labeled.

Specifically, the CD19-ECD described herein is conjugated directly or indirectly to the carrier or label e.g., to generate a "labeled" CD19-ECD. The label may be detectable by itself e.g., radioisotope labels or fluorescent labels, or, in the case of an enzymatic label, may catalyze chemical alteration of a substrate compound or composition which is detectable. Furthermore, the label may be recognizable by a secondary detection reagent (which may be labeled with, e.g., a fluorescent label or radioisotope label, or which may be recognized by yet another (i.e. a tertiary) detection reagent). Examples of such recognizable labels include biotin recognized by streptavidin, IgG-Fc recognized by anti-IgG-Fc antibodies or Protein A, peptide tags (such as a c-myc-tag, a His-tag or a FLAG-tag) recognized by an appropriate secondary binding reagent, among many others.

According to a specific aspect, the CD19-ECD described herein has a native conformation as determined by comprising one or more epitopes recognized by conformation specific antibodies.

Specifically, the CD19-ECD described herein is a monomeric protein.

According to a specific aspect, the invention further provides for a composition comprising the CD19-ECD described herein, wherein at least any one of 20%, 30%, 40%, 50%, 60%, 70%, 75%, 80%, 85%, 90%, 95%, 98%, or up to 100% of the CD19-ECD molecules are monomeric, wherein the percentage is w/w of total CD19-ECD protein.

Specifically, the CD19-ECD composition comprises less than any one of 40%, 35%, 30%, 25%, 20%, 15%, or 10% of high-molecular weight CD19-ECD aggregates (i.e., more than 200 kDa). Monomeric or aggregated CD19-ECD may be determined by standard assays, preferably by size exclusion chromatography (SEC), non-reducing SDS-PAGE or native PAGE, especially SEC combined with multi angle light scattering (MALS), non-reducing SDS-PAGE combined with Western Blot or native PAGE combined with Western Blot.

According to a specific aspect, the invention further provides for a diagnostic preparation comprising the CD19-ECD described herein and a diagnostic reagent in a composition or a kit of parts, comprising the components
a) the CD19-ECD described herein;
b) a diagnostic reagent;
c) and optionally a solid phase to immobilize at least one of the CD19-ECD and the diagnostic reagent.
Specifically, the diagnostic reagent is
i) a detectable label, which is optionally bound to the CD19-ECD, or to an anti-CD19 immunoreagent; or
ii) a reagent specifically reacting with the CD19-ECD and/or the reaction product of the CD19-ECD binding to an anti-CD19 immunoreagent, or
iii) a reagent competing with the CD19-ECD binding to an anti-CD19 immunoreagent; or
iv) a reagent specifically reacting with a component (e.g. a peptide, a protein, or biotin) fused to the CD19-ECD.

Specifically, the target analyte is a biological or artificial anti-CD19 compound (herein also referred to as anti-CD19 immunoreagent) comprising a binding site that specifically recognizes the CD19-ECD described herein and optionally cross-reacts with human wtCD19-ECD. According to a specific aspect, the anti-CD19 immunoreagent is specifically recognizing wild-type human CD19 expressed on the surface of native human B-cells.

Specifically, the anti-CD19 immunoreagent is selected from the group consisting of antibodies, antibody fragments, antibody-fusion constructs, bispecific antibodies, trispecific antibodies, immunotoxins, engineered alternative binder scaffolds, chimeric antigen receptors (CARs), human or non-human (e.g., animal or artificial) cells, such as T cells, NK cells or other immune cells, in particular those engineered to express a chimeric antigen receptor (CAR).

Specifically, the CD19-ECD described herein can be used in a method for the in vitro determination of an anti-CD19 immunoreagent in a sample. Specifically, such method employs a diagnostic CD19-ECD preparation (or such preparation as kit of parts) as described herein.

Specifically, the quality, quantity, or potency of said anti-CD19 immunoreagent is determined e.g., by a suitable test measuring the quality and quantity of reaction products, respectively. Specifically, the potency test is used to determine the activity of an anti-CD19 immunoreagent to bind wtCD19, e.g. measuring the expression level of CD19-specific CARs on engineered immune cells and/or the frequency of such CAR-expressing cells in samples of human subjects such as cancer patients.

According to a further specific aspect, the CD19-ECD described herein is used as a standard or reference control and prepared for use in a method of determining CD19 in a sample e.g., a biological sample comprising B cell expressed CD19, or a sample of a pharmaceutical or diagnostic (reference control) preparation.

A diagnostic CD19-ECD preparation may be provided as a standard (or reference control) or as a reagent, either as a storage-stable preparation and/or a ready-to-use preparation. In particular, a reagent may be used in a reaction mixture with a sample comprising the target analyte, or a conserved form of such reagent. Storage-stable forms refer to conserved forms which are, e.g. lyophilized, snap-frozen (e.g. in liquid nitrogen), ultra-low-temperature storage (e.g. −70° C. and −80° C.), cold-storage (e.g. −20° C.-5° C.) and controlled room temperature (e.g. 15° C.-27° C.) preparations, standard sample storage preparations as e.g. glycerol-stocks, tissue paraffin blocks. Suitable reagents are typically in the form of an aqueous solution, specifically (physiological) buffer conditions (e.g. EDTA buffered, phosphate buffer, HBSS, citrate buffer etc.).

Specifically, the diagnostic CD19-ECD preparation is provided in a kit of parts, in particular in the storage-stable form. Such kit preferably comprises all essential components to determine a target analyte such as an anti-CD19 immunoreagent in a reaction mixture or a biological sample, optionally without common or unspecific substances or components, such as water, buffer or excipients. The storage stable kit can be stored preferably at least 6 months, more preferably at least 1 or 2 years. It may be composed of dry (e.g. lyophilized) components, and/or include preservatives.

Specifically, a diagnostic kit comprises one or more reagents capable of specifically reacting with the CD19-ECD (or with other components fused to the CD19-ECD, such as, e.g., biotin, a peptide or a protein) and/or a specific detection molecule suitable for determining the level of a reaction product, which are provided in the storage-stable form, preferably as a packaged unit.

According to a specific aspect, the invention further provides for a method of determining the quality, quantity, or potency of an anti-CD19 immunoreagent, comprising
  a) providing the CD19-ECD described herein, and
  b) in vitro determining the binding of the CD19-ECD to an anti-CD19 immunoreagent in a sample upon incubating the sample under physiological conditions, thereby producing a reaction product, and
  c) qualitatively and/or quantitatively determining the reaction product, thereby determining the quality, quantity and/or potency of the anti-CD19 immunoreagent to bind wild-type human CD19 antigen expressed on the surface of native human B-cells.

Specifically, the sample includes, but is not limited to samples from patients or non-human animals (e.g. tissues or body fluids, specifically blood, plasma, serum, urine or bone marrow biopsies), and therapeutic or diagnostic products (e.g. recombinantly expressed proteins, especially antibodies, antibody fragments, antibody-fusion constructs, bispecific antibodies, trispecific antibodies, immunotoxins, engineered alternative binder scaffolds, CARs, human or non-human (e.g., animal or artificial) cells, such as T cells, NK cells or other immune cells, in particular those engineered to express a chimeric antigen receptor (CAR).

Specifically, the reaction product is any of the samples listed above bound to CD19-ECD.

Specifically, the reaction product can be detected by a detectable compound or composition which is conjugated directly or indirectly to CD19-ECD or its cognate binding partner (e.g., a CD19 specific antibody or receptor), or to the reaction product formed upon binding the CD19-ECD to the respective anti-CD19 immunoreagent, so as to generate a "labeled" one. The label may be detectable by itself e.g., radioisotope labels or fluorescent labels, or, in the case of an enzymatic label, may catalyze chemical alteration of a substrate compound or composition which is detectable. Furthermore, the label may be recognizable by a secondary detection reagent (which may be labeled with, e.g., a fluorescent label or radioisotope label, or which may be recognized by yet another (i.e. a tertiary) detection reagent). Examples of such recognizable labels include biotin recognized by streptavidin, IgG-Fc recognized by anti-IgG-Fc antibodies or Protein A, peptide tags (such as a c-myc-tag, a His-tag or a FLAG-tag) recognized by an appropriate secondary reagent, among many others.

According to a specific aspect, the invention further provides for the medical use of the CD19-ECD described herein. Specifically, the CD19-ECD described herein is provided for use as a medicament in a method of treating a subject in need of neutralizing, or removing a circulating anti-CD19 immunoreagent, such as a human patient. Specifically, a patient can be treated by administering an effective amount of the CD19-ECD described herein, which is effective to antagonize or neutralize an anti-CD19 immunoreagent. According to a specific treatment regimen, a patient who suffers from a disease, e.g., a disease where reduction or depletion of B cells (in particular those expressing CD19) is desired, among those cancer or autoimmune diseases, is treated with an anti-CD19 immunoreagent, such as T cells engineered to express a chimeric antigen receptor (CAR) targeting CD19. Such patients may be further treated with an effective amount of the CD19-ECD described herein where antagonizing or neutralizing such CAR-T cells is desired.

Specifically, the invention further provides for a pharmaceutical preparation comprising the CD19-ECD described herein and a pharmaceutically acceptable carrier, adjuvants or excipient. Pharmaceutical carriers suitable for facilitating such means of administration are well known in the art. Specific embodiments refer to immunogenic formulations of the CD19-ECD described herein, which comprise a pharmaceutically acceptable carrier and/or adjuvant, which trigger an (e.g. antibody) immune response upon administering to a subject. An immunogenic CD19-ECD composition usually comprises the CD19-ECD antigen and a carrier, which may specifically comprise an adjuvant. The term "adjuvant" as used herein specifically refers to a compound that when administered in conjunction with an antigen augments and/or redirects the immune response to the antigen, but when administered alone does not generate an immune response to the antigen. Adjuvants can augment an immune response by several mechanisms including lymphocyte recruitment, stimulation of B and/or T cells, and stimulation of macrophages. Exemplary carriers are liposomes or cationic peptides; exemplary adjuvants are aluminium phosphate or aluminium hydroxide, MF59 or CpG oligonucleotides.

Pharmaceutically acceptable carriers generally include any and all suitable solvents, dispersion media, coatings, antibacterial and antifungal agents, isotonic and absorption delaying agents, and the like that are physiologically compatible with an antibody or related composition or combination provided by the invention. Further examples of pharmaceutically acceptable carriers include sterile water, saline, phosphate buffered saline, dextrose, glycerol, ethanol, polyethylene glycol, and the like, as well as combinations of any thereof.

According to a specific aspect, the invention further provides for a nucleic acid molecule encoding the CD19-ECD described herein.

According to a specific aspect, the invention further provides for an expression system for producing the CD19-ECD described herein in an ex vivo cell culture, such a recombinant host cell comprising the nucleic acid molecule described herein.

Suitable host cells may be selected from those capable of performing N-glycosylation. Specific host cells may be selected from the group consisting of mammalian, insect, or yeast cells, e.g., HEK293 cells, CHO cells, NS0 cells, Sf9 cells, High Five cells, *Pichia pastoris, Saccharomyces cerevisiae*, among many others.

According to a specific aspect, the invention further provides for a method of producing the CD19-ECD described herein, wherein a recombinant host cell described herein is cultivated or maintained under conditions to produce said CD19-ECD.

FIGURES

FIG. 1: Sequences described herein.

FIG. 2: Flow cytometric analysis of wtCD19-ECD and Superfolder mutants (SF-01-SF-15), n=3. Data (GMFI, geometric mean fluorescence intensity) shown represent HA positive cells (staining with anti-HA Alexa Fluor 647 antibody) and were normalized to CD19-wt. A: Cells were incubated with anti c-myc (clone 9E10) Alexa Fluor 488 antibody. B: Cells were incubated with rabbit anti-CD19 antibody (clone FMC63), followed by detection via staining with anti-rabbit F(ab')2 Fragment Alexa Fluor 488. C: Cells were incubated with anti-CD19 antibody (clone HIB19)-Phycoerythrin. D: Cells were only incubated with anti-HA Alexa Fluor 647.

Figure 3:
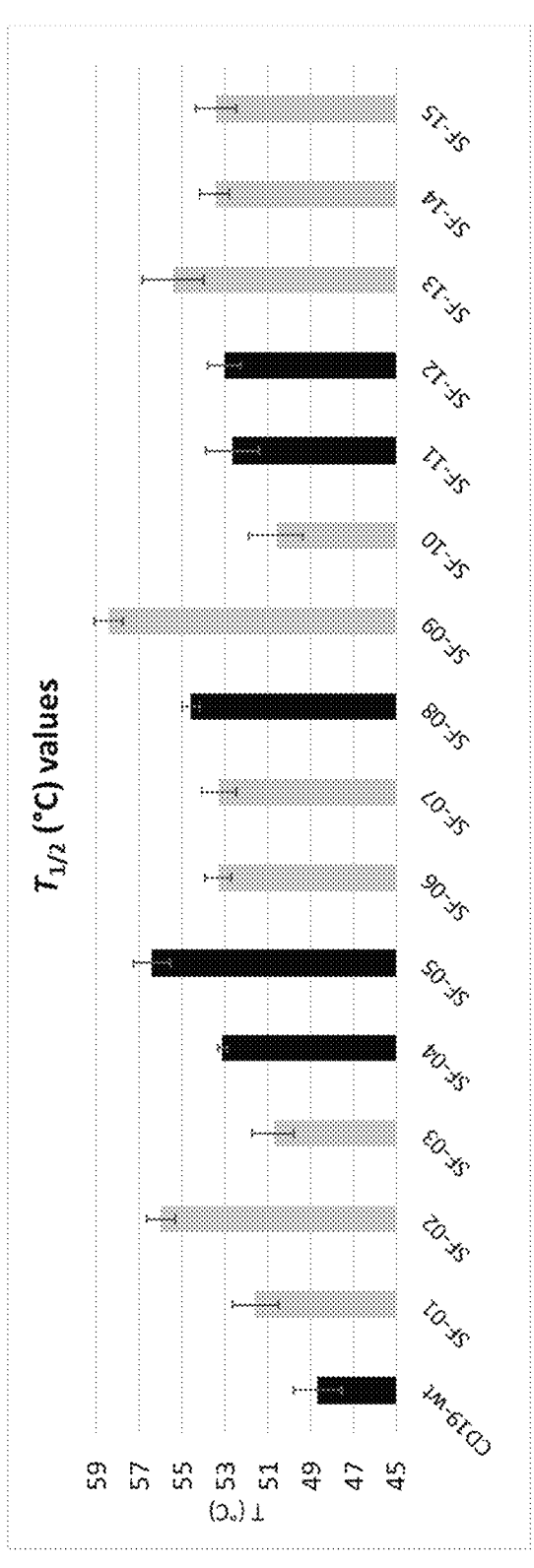
Figure 3:
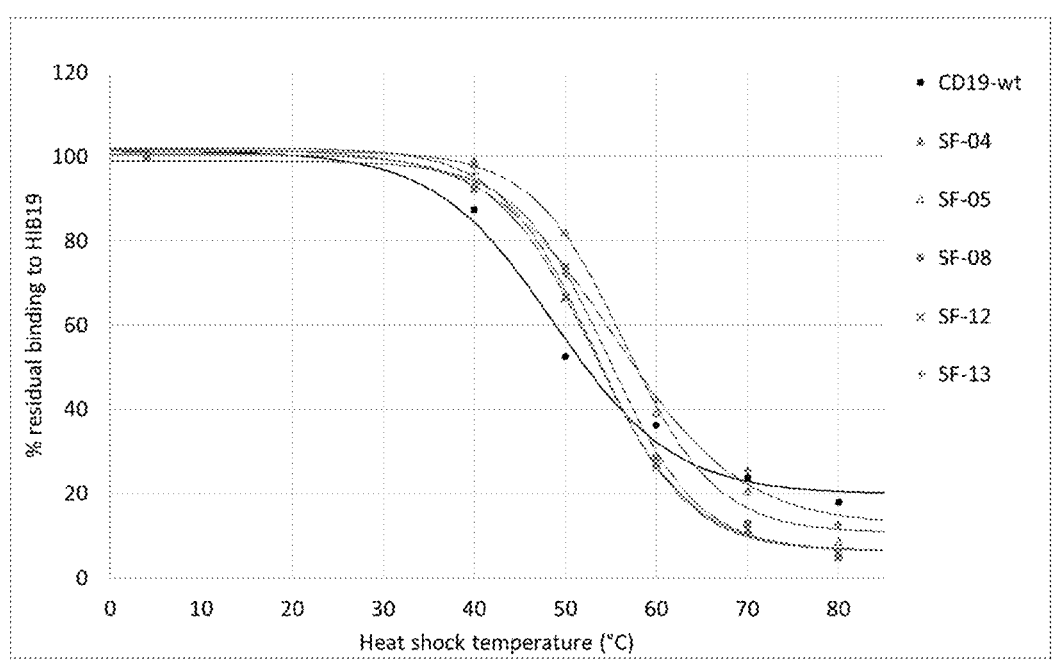

FIG. 3 (A) $T_{1/2}$ values of wtCD19-ECD (referred to as CD19-wt) and Superfolder mutants (SF-01-SF-15) evaluated by fitting the $MFI_{tot}$ for binding of the anti-CD19 antibody (clone HIB19) to equation 1, (n=3). The black coloured clones were chosen for soluble expression.

(B) Temperature exposure of wtCD19-ECD (referred to as CD19-wt) and SF clones (SF-04, SF-05, SF-08, SF-12, SF-13) that were chosen for soluble expression in HEK293-6E cells. The residual binding of the CD19-ECD proteins to the anti-CD19 antibody (clone HIB19) is plotted versus the incubation temperature. Resulting data were fitted according to Equ. 1, yielding the $T_{1/2}$ values.

Figure 4:
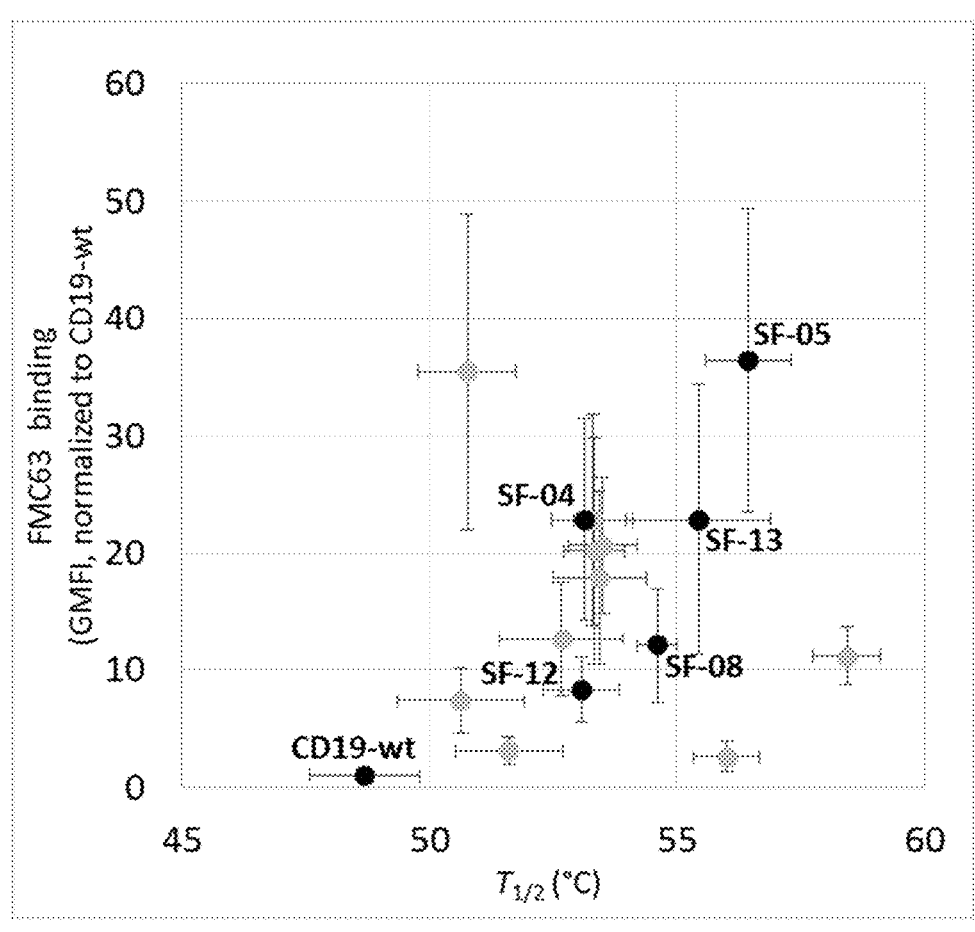

FIG. 4: $T_{1/2}$ values plotted against binding (GMFI, normalized to wtCD19-ECD—referred to as CD19-wt) of the anti-CD19 antibody (clone FMC63) to CD19-wt and Superfolder mutants (SF-01-SF-15). The black coloured clones were chosen for soluble expression.

Figure 5:
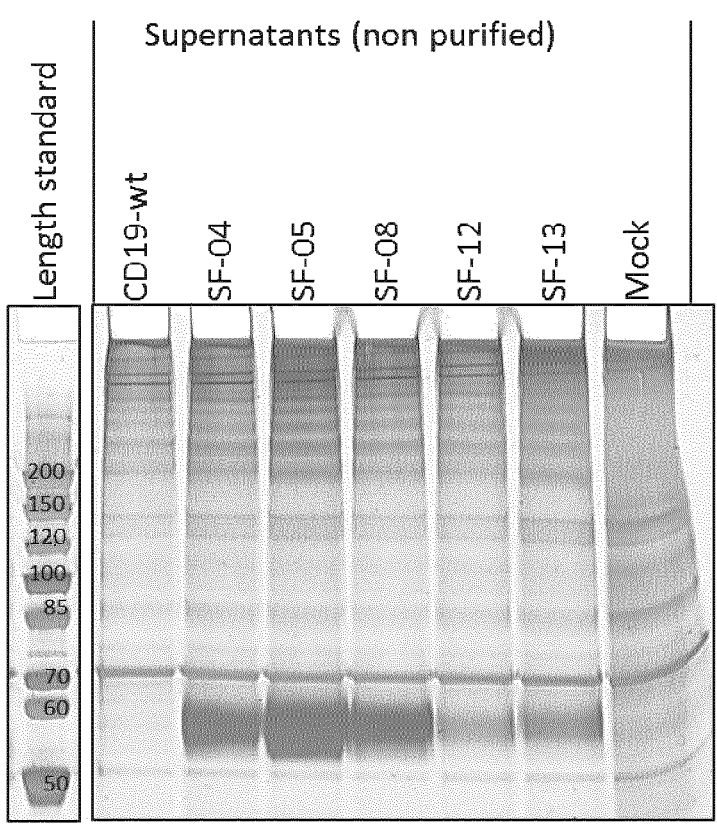

FIG. 5: SDS-PAGE of 37 µL supernatant of HEK293 cells transiently transfected with expression plasmids encoding wtCD19-ECD (referred to as CD19-wt), SF04, SF-05, SF-08, SF-12, SF-13 and mock. Length standard refers to PageRuler™ Unstained Protein Ladder (#26619, Thermo Fisher Scientific).

Figure 6:
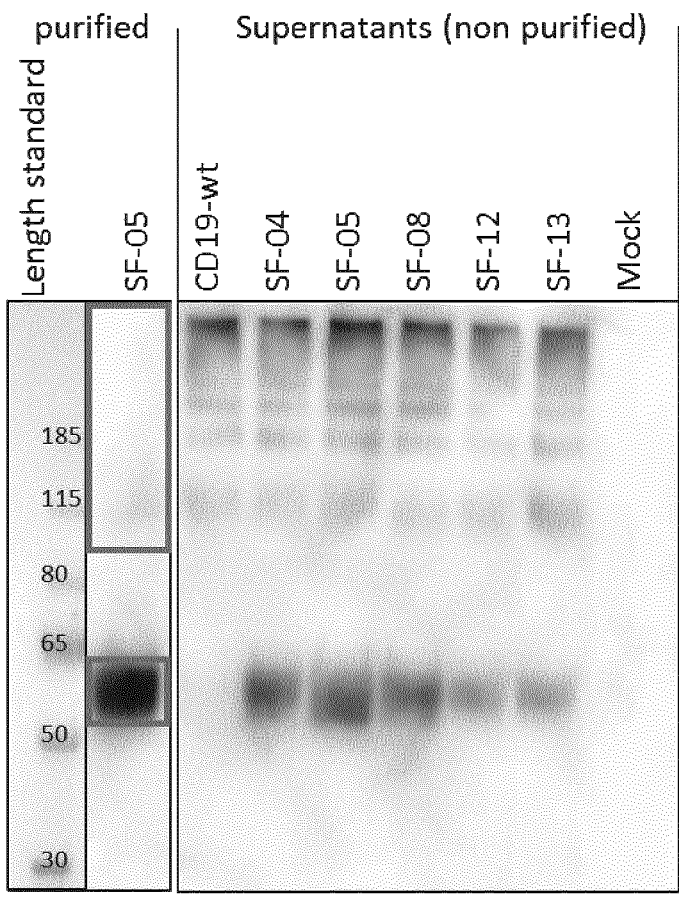

FIG. 6: Western Blot of 18 µL supernatant of HEK293 cells transiently transfected with expression plasmids encoding wtCD19-ECD (referred to as CD19-wt), SF-04, SF-05, SF-08, SF-12, SF-13 and mock. As reference 600 ng of HisTrap FF and SEC purified SF-05 was loaded. Length standard refers to PageRuler™ Plus Prestained Protein Ladder (#26614, Thermo Fisher Scientific). Grey circled bands (Aggregate and monomeric protein content) refer to table 7.

Figure 7:
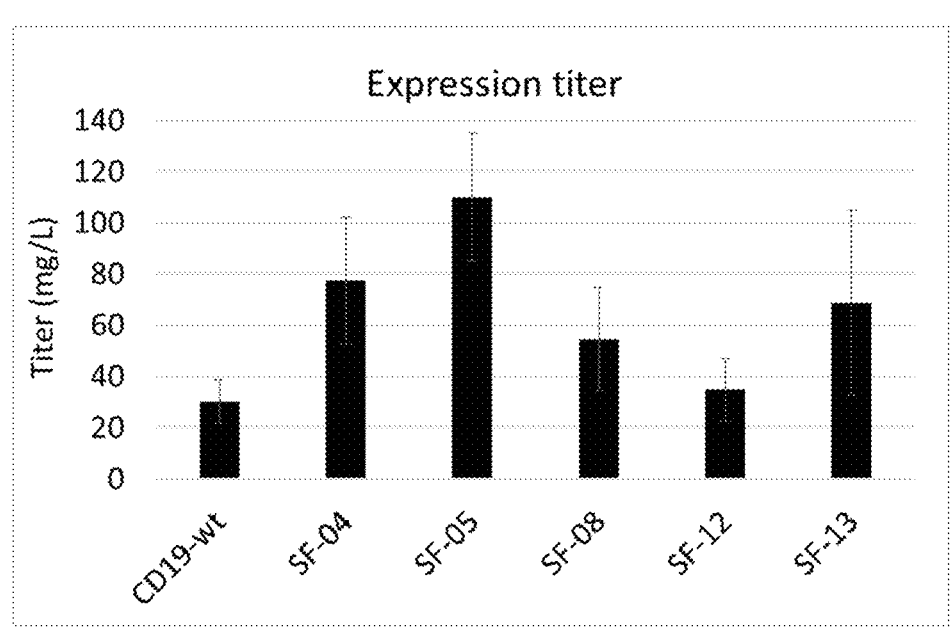

FIG. 7: Soluble expression titers of wtCD19-ECD (referred to as CD19-wt) and SF mutants determined with bio-layer interferometry (n=3).

Figure 8:
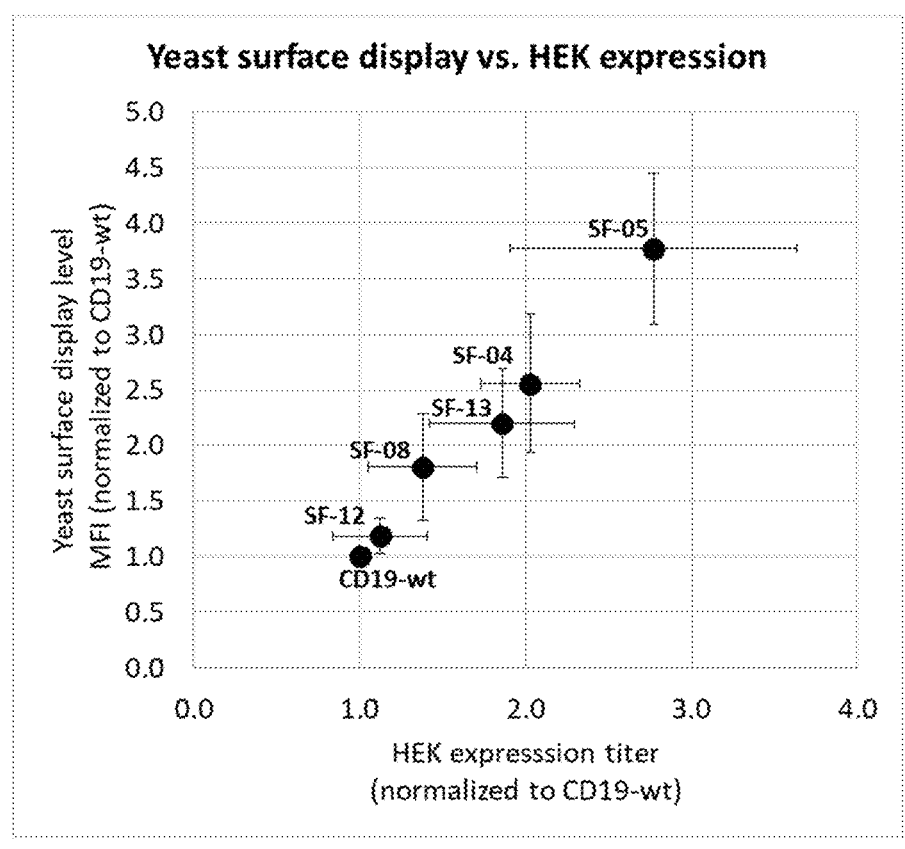

FIG. 8: Correlation of yeast surface display (c-myc binding) and soluble expression in HEK293-6E cells analysed with bio-layer interferometry using anti-penta His biosensors (n=3).

Figure 9:
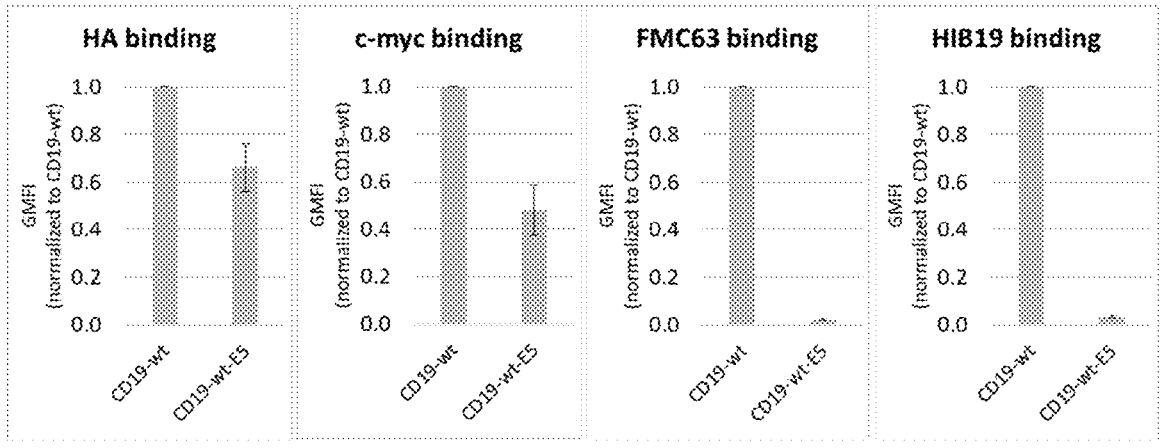

FIG. 9: Flow cytometric analysis of wtCD19-ECD (referred to as CD19-wt) and the extended wtCD19-ECD including the 13 residues from exon 5, n=3. A: Data (GMFI, geometric mean fluorescence intensity) shown represent HA positive cells (staining with anti-HA Alexa Fluor 647 antibody) and were normalized to CD19-wt. For all following data, analysis was performed with HA positive cells only. B: Cells were incubated with anti c-myc mouse IgG1 (clone 9E10), followed by detection via staining with goat anti-mouse Alexa Fluor 488.C: Cells were incubated with rabbit anti-CD19 antibody (clone FMC63), followed by detection via staining with anti-rabbit F(ab')2 Fragment Alexa Fluor 647. D: Cells were incubated with anti-CD19 antibody (clone HIB19)-Phycoerythrin.

FIG. 10: Flow cytometric analysis of wtCD19-ECD (referred to as CD19-wt), the N138Q mutant and single Superfolder mutants (M561, M56V, R57S and R57T), n=3. A: Data (GMFI, geometric mean fluorescence intensity) shown represent HA positive cells (staining with anti-HA Alexa Fluor 647 antibody) and were normalized to CD19-wt. For all following data, analysis was performed with HA positive cells only. B: Cells were incubated with anti c-myc (clone 9E10) Alexa Fluor 488 antibody. C: Cells were incubated with rabbit anti-CD19 antibody (clone FMC63), followed by detection via staining with anti-rabbit F(ab')2 Fragment Alexa Fluor 488. D: Cells were incubated with anti-CD19 antibody (clone HIB19)-Phycoerythrin.

Figure 11:
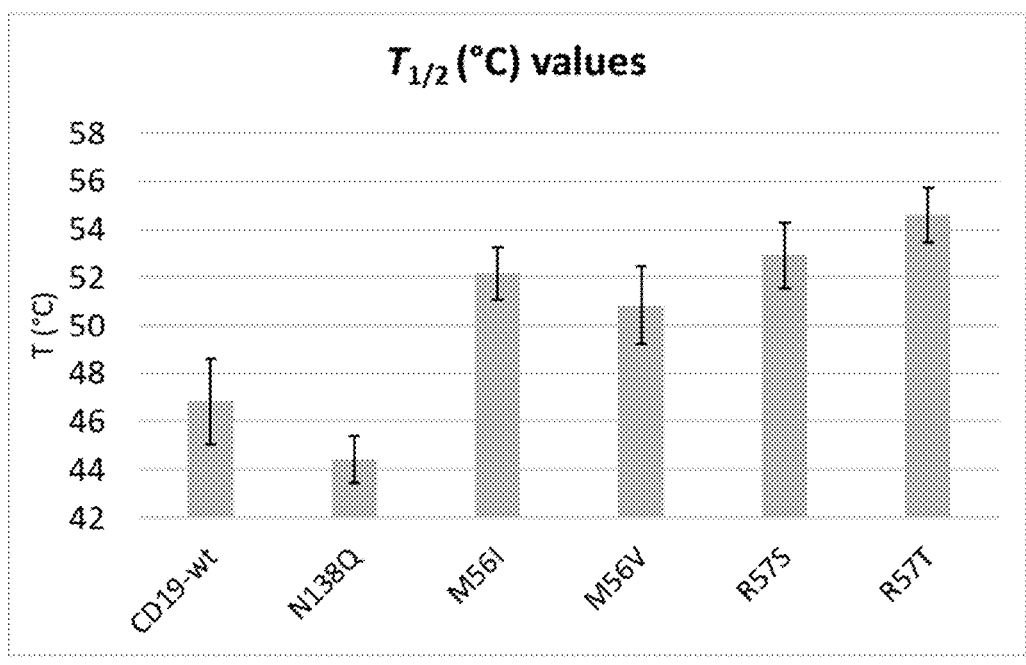

FIG. 11: $T_{1/2}$ values of wtCD19-ECD (referred to as CD19-wt), the N138Q mutant and single Superfolder mutants (M561, M56V, R57S and R57T) evaluated by fitting the $MFI_{tot}$ for binding of the anti-CD19 antibody (clone HIB19) to Equ. 1, (n=3).

Figure 12:
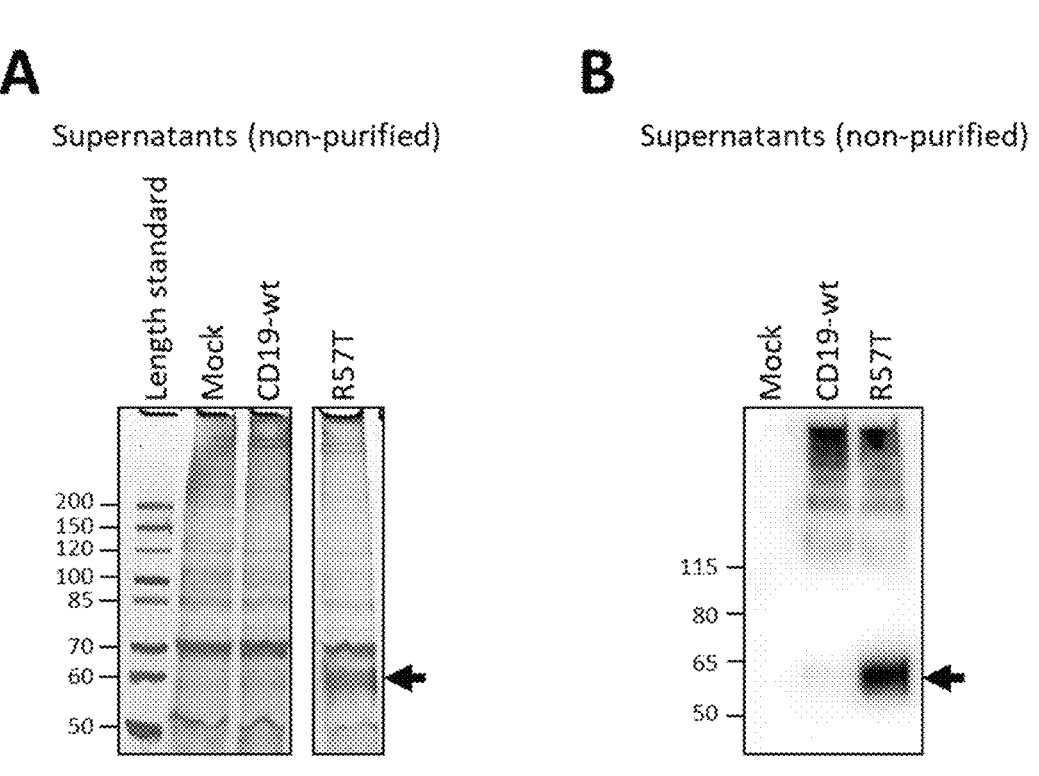

FIG. 12: (A) SDS-PAGE of 37 µL supernatant of HEK293 cells transiently transfected with expression plasmids encoding wtCD19-ECD (referred to as CD19-wt), the single mutant R57T and mock. Length standard refers to PageRuler™ Unstained Protein Ladder (#26619, Thermo Fisher Scientific). (B) Western Blot of 37 µL supernatant of HEK293 cells transiently transfected with expression plasmids encoding CD19-wt, the single mutant R57T and mock. Length standard refers to PageRuler™ Plus Prestained Protein Ladder (#26614, Thermo Fisher Scientific). The black arrows mark the monomeric band of the single mutant R57T.

DETAILED DESCRIPTION OF THE INVENTION

Specific terms as used throughout the specification have the following meaning.

The term "CD19" as used herein shall refer to a protein otherwise known as Cluster of Differentiation 19, B-lymphocyte antigen CD19, B-lymphocyte surface antigen B4, B4 antigen, or Differentiation antigen CD19. Naturally occurring or wild-type CD19 is found on the surface of B cells, which express the extracellular domain of CD19 (CD19-ECD) at the outer surface. The CD19-ECD is considered a useful antigen for recognizing and targeting cancer cells that arise from this type of B cells, e.g., B-cell lymphomas, among others. CD19 is a protein that in humans is encoded by the CD19 gene.

According to the UniProtKB entry P15391, human CD19 isoform 1 predominantly expressed by human B cells comprises an extracellular domain which consists of the amino acid sequence identified as SEQ ID NO:1. Human B cells are herein referred to as "native", if obtained from human samples such as circulating blood.

SEQ ID NO:1 identifies the CD19-ECD (exons 1-4) which is human and wild-type, herein referred to as wtCD19-ECD or CD19-ECD or CD19-ECDwt or CD19-wt. SEQ ID NO:1 may be modified by one or more point mutations, including amino acid substitutions, insertions and/or deletions, to produce CD19-ECD mutants, which are further described herein. Unless explicitly described in a different way, the positions of amino acids in the CD19-ECD mutants are those of SEQ ID NO:1, thus numbered as presented in SEQ ID NO:1, though the CD19-ECD may be fragmented or one or more of the core regions may include deletions at the distal ends and/or within the core regions.

For production of recombinant human CD19-ECD described herein, a nucleic acid molecule encoding the respective amino acid sequence can be expressed in (or transferred into) a recombinant host cell, e.g., a mammalian host cell, isolated and purified. Identity of the CD19-ECD and its monomers can be confirmed by, e.g., intact mass spectrometry and peptide mass fingerprint analyses (Miltenyi Biotec, Bergisch Gladbach, Germany), Western Blot, ELISA, among many other methods.

Though the CD19-ECD described herein is particularly stable without stabilizing agents or fusions (in particular without being fused to Fc), specific embodiments refer to CD19-ECD fusion proteins, such as a fusion to human IgG1-Fc, or CD19-ECD that is conjugated to otherwise heterologous compounds. Recombinant fusion proteins can likewise be produced upon expression by a recombinant host cell.

Exemplary methods employ transient or stable expression in, e.g., mammalian hosts, insect cells, yeast cells, bacterial cells, among many other expression systems well known in the art, and purification of the protein of interest from supernatant via chromatography such as affinity and size exclusion chromatography.

The term "compete", as used herein with regard to binding an antigen (such as CD19-ECD described herein) to an antigen-binding molecule (a specific or cognate binding partner, e.g., an antibody or a receptor) specifically recognizing said antigen, means that a first antigen or epitope comprised therein binds to a cognate binding partner in a manner sufficiently similar to the binding of a second antigen or epitope, such that the result of binding of the first antigen or epitope with its cognate binding partner is detectably decreased in the presence of the second antigen or epitope compared to the binding of the first antigen or epitope in the absence of the second one. The alternative, where the binding of the second antigen or epitope to cognate binding partner is also detectably decreased in the presence of the first one, can, but need not be the case. That is, a first antigen or epitope can inhibit the binding of a second one to its cognate binding partner without that second antigen or epitope inhibiting the binding of the first one to its respective binding partner. However, where each antigen or epitope detectably inhibits the binding of others with its cognate binding partner, whether to the same, greater, or lesser extent, the antigens or epitopes are said to "compete" with each other for being bound by their respective (specific) binding partners.

Vice versa, a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "compete" with each other for binding of their respective epitope(s).

The CD19-ECD described herein specifically has a structure comprising conformational epitopes which are otherwise found in naturally occurring (wild-type) human CD19-ECD which are recognized by conformation specific antibodies as further described herein. Thus, the CD19-ECD described herein optionally competes with human wt CD19-ECD (e.g., identified by SEQ ID NO:1) for binding (or being bound) by a respective conformation specific antibody, receptor or CAR-T cells targeting human wt CD19-ECD.

Numerous types of competitive binding assays can be used to determine if one antigen or antigen binding molecule (e.g. an antibody or a receptor) competes with another, for example: solid phase direct or indirect radioimmunoassay (RIA); solid phase direct or indirect enzyme immunoassay (EIA); sandwich competition assay; solid phase direct biotin-avidin EIA; solid phase direct labelled assay, solid phase direct labelled sandwich assay; solid phase direct label RIA; solid phase direct biotin-avidin EIA; direct labelled RIA; yeast-display experiments analysed by flow cytometry; surface plasmon resonance (SPR); biolayer interferometry (BLI); isothermal titration calorimetry (ITC); flow cytometry experiments with CD19-positive cells; flow cytometry experiments with cells expressing a CD19-specific immunoreagent or having conjugated a CD19-specific immunoreagent; flow cytometry experiments with beads loaded with either CD19-ECD or with an anti-CD19 immunoreagent, among many others.

In particular, "Competitively binding" or "competition" herein means a greater relative inhibition than about 30%, e.g., as determined by any of the competitive binding assays described above.

The term "conservative" with regard to an amino acid substitution are herein understood as those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. Particular examples of conservative exchanges of amino acids are within one, two or three families of amino acids.

Regarding specific amino acid substitution(s) described herein at one or more selected amino acid positions within SEQ ID NO:1, a series of preferred amino acids are described herein, including one or more exemplified amino acid substitutions and optionally alternative amino acids which are conservative amino acid substitutions e.g., described in Table 1.

The term "core region" with respect to a CD19-ECD is herein understood as a certain part of the CD19-ECD extending through certain positions within SEQ ID NO:1, though the core region may include gaps or be fragmented e.g., to comprise at least 80% of the respective region of SEQ ID NO:1, or at least any one of 80%, 85%, 90%, 95%, or 95%, 97%, 98%, or 99%, or up to 100%.

The first core region described herein refers to positions 2-98 of SEQ ID NO:1, and typically comprises beta-strands and loop structures such as further described herein.

The second core region described herein refers to positions 167-258 of SEQ ID NO:1, and typically comprises beta-strands and loop structures such as further described herein.

The third core region described herein refers to positions 99-166 of SEQ ID NO:1, and typically comprises beta-strands and loop structures such as further described herein.

The first core region specifically comprises parts of two domains, herein referred to as "domain 1" and "domain 2" each being composed of four beta-strands and loop regions connecting the beta-strands. Positions 2-50 belong to domain 1, positions 51-98 belong to the domain 2. The part of domain 2 contains usually a potential N-glycosylation site at position 67.

The second core region specifically comprises at least parts of two domains, herein referred to as "domain 1" and "domain 2" each being composed of four beta-strands and loop regions connecting the beta-strands. Positions 167-215 belong to domain 2, positions 216-258 belong to domain 1. The part of domain 1 typically contains a potential N-glycosylation site at position 246. Domain 1 refers to Ig fold 1 encompassing residues at position 2-50 (core region 1) and 216-258 (core region 2) and is composed of eight beta-strands involved in a three- and a five-stranded beta-sheet. Cysteine residues at position 19 and 246 usually form a stabilizing disulphide bridge. Domain 2 refers to Ig fold 2 encompassing residues at position 51-98 (core region 1) and 167-215 (core region 2) and is composed of eight beta-strands involved in a three- and a five-stranded beta-sheet. Cysteine residues at position 78 and 181 typically form a stabilizing disulphide bridge.

The third core region specifically comprises typically three beta-strands and adjoining loop regions, which may be partially unstructured or flexible. Furthermore, said third core region typically contains three potential N-glycosylation sites at positions 106, 119 and 162 and/or one disulfide bond connecting cysteine residues at positions 115 and 154, respectively.

The term "conformation specific" in relation to an epitope or antibody which specifically recognizes an epitope is herein understood as follows.

Conformational epitopes are comprised of amino acids or carbohydrates brought together by folding the polypeptide to form a tertiary structure and the amino acids are not necessarily adjacent to one another in the linear sequence. Specifically and with regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen. The native structure of proteins such as the CD19-ECD described herein may specifically comprise one or more conformational epitopes that are specifically recognized by cognate binding partners which have been determined to specifically react with a naturally-occurring wild-type protein, but with far less or substantially no binding reaction with heat denatured or otherwise denatured (or aggregated) protein. It is understood that a protein being recognized by such cognate binding partners has a native structure or conformation, and the presence of said one or more conformational epitopes is understood to effectively determine the quality of a mutant protein.

Herein the term "epitope" shall particularly refer to the single epitope recognized by an antibody, or epitopes which are shared by at least two different antigens, such as the conformational epitopes shared by the wtCD19-ECD and CD19-ECD described herein (which are CD19-ECD mutants).

Exemplary conformational antibodies recognizing the wild-type structure of the CD19-ECD are commercially available e.g., anti-CD19 mAb (clone HIB19, commercially available from BioLegend, San Diego, CA) and anti-CD19 mAb (clone FMC63, commercially available from Absolute Antibody Ltd, Oxford, UK)

The term "label" or "detectable label" is herein understood as a detectable compound or composition which is conjugated directly or indirectly to an antigen (e.g., a CD19-ECD) or its cognate binding partner (e.g., a CD19 specific antibody or receptor), or to the immune complex (reaction product) formed upon binding the antigen to its cognate binding partner, so as to generate a "labeled" one. The label may be detectable by itself e.g., radioisotope labels or fluorescent labels, or, in the case of an enzymatic label, may catalyze chemical alteration of a substrate compound or composition which is detectable. Furthermore, the label may be recognizable by a secondary detection reagent (which may be labeled with, e.g., a fluorescent label or radioisotope label, or which may be recognized by yet another (i.e. a tertiary) detection reagent). Examples of such recognizable labels include biotin recognized by streptavidin and IgG-Fc recognized by anti-IgG-Fc antibodies or Protein A, peptide tags (such as a c-myc-tag, a His-tag or a FLAG-tag) recognized by an appropriate secondary reagent, among many others.

The term "heterologous" shall mean from any source other than naturally occurring sequences. For example, mutants of the CD19-ECD having the amino acid sequence identified as SEQ ID NO:1, comprise a heterologous sequence which includes one or more amino acids that do not naturally occur in SEQ ID NO:1. The term "heterologous" also refers to a compound which is either foreign to a given protein such as the CD19-ECD described herein, i.e. "exogenous", or not found in nature in conjunction with said protein, thereby producing an artificial construct or protein e.g., a fusion, chimeric or hybrid protein.

The term "heterologous" as used herein with respect to a nucleotide sequence, recombinant nucleotide sequence or construct such as an expression cassette, refers to a compound which is either foreign to a given host cell, i.e. "exogenous", such as not found in nature in said host cell, or that is naturally found in a given host cell, e.g., is "endogenous", however, in the context of a heterologous construct or integrated in such heterologous construct, e.g., employing a heterologous nucleic acid fused or in conjunction with an endogenous nucleic acid, thereby rendering the construct heterologous. The heterologous nucleotide sequence as found endogenously may also be produced in an unnatural, e.g., greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein. Specifically, heterologous nucleotide sequences are those not found in the same relationship to a host cell in nature. Any recombinant or artificial nucleotide sequence is understood to be heterologous. An example of a heterologous polynucleotide is a promoter operably linked to a coding sequence, with which it is not natively associated in the host cell (i.e. not naturally-occurring in such host cell) used for expressing the coding sequence under the control of said promoter.

The term "host cell" as used herein shall refer to a single cell, a single cell clone, or a cell line of a host cell.

The term "cell line" as used herein refers to an established clone of a particular cell type that has acquired the ability to proliferate over a prolonged period of time. A cell line is typically used for expressing an endogenous or recombinant gene, or products of a metabolic pathway to produce polypeptides or cell metabolites mediated by such polypeptides. A "production cell line" is commonly understood to be a cell line used in a cell culture to obtain the product of a production process. The host cell producing a CD19-ECD described herein is also referred to as "production host cell", and a respective cell line a "production cell line".

Specific embodiments described herein refer to a production host cell line which is engineered to express a recombinant CD19-ECD described herein. Typically, such host cell is cultured under conditions to express a CD19-ECD coding gene into the cell culture supernatant. The recombinant CD19-ECD can then be isolated from the cell culture supernatant and purified as further described herein.

The term "host cell" shall particularly apply to any eukaryotic or prokaryotic cell or organism, which is suitably used for recombination purposes to produce CD19-ECD described herein. It is well understood that the term "host cell" does not include human beings. Specifically, host cells as described herein are artificial organisms and derivatives of native (wild-type) host cells. It is also well understood that the host cells, methods and uses described herein, e.g., specifically referring to those comprising a heterologous expression cassette comprising a nucleotide sequence encoding the CD19-ECD described herein, said heterologous expression cassettes or constructs, said transfected or transformed host cells and recombinant proteins, are non-naturally occurring, "man-made" or synthetic, and are therefore not considered as a result of "law of nature".

The term "cell culture" or "culturing" or "cultivation" as used herein with respect to a host cell refers to the maintenance of cells in an artificial, e.g., an in vitro environment, under conditions favoring growth, differentiation or continued viability, in an active or quiescent state, of the cells, specifically in a controlled bioreactor according to methods known in the industry.

When culturing a cell culture using appropriate culture media, the cells are brought into contact with the media in a culture vessel or with substrate under conditions suitable to support culturing the cells in the cell culture. As described herein, a culture medium is provided that can be used for the growth of host cells e.g., eukaryotic cells, yeast or filamentous fungi. Standard cell culture techniques are well-known in the art.

The cell cultures as described herein particularly employ techniques which provide for the production of a secreted CD19-ECD (in particular as a soluble protein), such as to obtain the CD19-ECD in the cell culture medium, which is separable from the cellular biomass, herein referred to as "cell culture supernatant", and may be purified to obtain the CD19-ECD at a higher degree of purity. When a protein (such as e.g., the CD19-ECD described herein) is produced and secreted by the host cell in a cell culture, it is herein understood that such proteins are secreted into the cell culture supernatant, and can be obtained by separating the cell culture supernatant from the host cell biomass, and optionally further purifying the protein to produce a purified protein preparation.

The term "expression" or "expression cassette" as used herein refers to nucleic acid molecules containing a desired coding sequence and control sequences in operable linkage, so that host cells transformed or transfected with these sequences are capable of producing the encoded proteins. In order to effect transformation, the expression system may be included in a vector; however, the relevant DNA may also be integrated into a host cell chromosome. Expression may refer to secreted or non-secreted expression products, including polypeptides or metabolites.

Expression cassettes may be conveniently provided as expression constructs e.g., in the form of "plasmids" or "vectors", which are typically DNA sequences that are required for the transcription of cloned recombinant nucleotide sequences, i.e. of recombinant genes and the translation of their mRNA in a suitable host organism. Expression vectors or plasmids usually comprise an origin for autonomous replication or a locus for genome integration in the host cells, selectable markers (e.g., an amino acid synthesis gene or a gene conferring resistance to antibiotics such as zeocin, kanamycin, G418 or hygromycin, nourseothricin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences, such as artificial chromosomes.

Expression vectors may include but are not limited to cloning vectors, modified cloning vectors and specifically designed plasmids. Preferred expression vectors described herein are expression vectors suitable for expressing of a recombinant gene in a eukaryotic host cell and are selected depending on the host organism. Appropriate expression vectors typically comprise regulatory sequences suitable for expressing DNA encoding a recombinant protein in a eukaryotic host cell. Examples of regulatory sequences include promoter, operators, enhancers, ribosomal binding sites, and sequences that control transcription and translation initiation and termination. The regulatory sequences are typically operably linked to the DNA sequence to be expressed.

Expression systems, genetic constructs or modifications described herein may employ tools, methods and techniques known in the art, such as described by J. Sambrook et al., Molecular Cloning: A Laboratory Manual (3rd edition), Cold Spring Harbor Laboratory, Cold Spring Harbor Laboratory Press, New York (2001).

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, CAR T cell therapy, tumor-infiltrating lymphocyte (TIL) immunotherapy, autologous cell therapy, engineered autologous cell therapy, and allogeneic T cell transplantation. However, one of skill in the art would recognize that the conditioning methods disclosed herein would enhance the effectiveness of any transplanted T cell therapy.

The term "immunoreagent", in particular targeting an antigen such as CD19 or the CD19-ECD, herein also referred to as an "anti-CD19 immunoreagent" is herein understood as an a binding moiety specifically recognizing CD19, such as molecules comprising an antigen-binding domain, or a receptor domain, or comprising at least a CD19 binding domain of any of the following: antibody, antibody fragment, antibody-fusion construct, bispecific antibody, trispecific antibody, immunotoxin, engineered alternative binder scaffold or chimeric antigen receptor (CAR) (or human or non-human (e.g., animal or artificial) cells, such as T cells, NK cells or other immune cells, in particular those engineered to express a CAR) specifically recognizing and capable of binding to said target antigen, thereby provoking an immune reaction or response. This immune response may involve either antibody production, or the activation of specific immunologically-competent cells, or both.

Anti-CD19 immunoreagents are specifically indicated in a large medical field e.g. cancer or tumors associated with expression of CD19.

Cancers that may be treated with an anti-CD19 immunoreagent include B-cell lymphomas, Acute Lymphoblastic Leukemia (ALL), AIDS-related lymphoma, ALK-positive large B-cell lymphoma, Burkitt's lymphoma, Chronic lymphocytic leukemia, CLL), Classical Hodgkin lymphoma, Diffuse large B-cell lymphoma (DLBCL), Follicular lymphoma, Intravascular large B-cell lymphoma, Large B-cell lymphoma arising in HHV8-associated multicentric Castleman's disease, Lymphomatoid granulomatosis, Lymphoplasmacytic lymphoma, Mantle cell lymphoma (MCL), Marginal zone B-cell lymphoma (MZL), Mucosa-Associated Lymphatic Tissue lymphoma (MALT), Nodal marginal zone B cell lymphoma (NMZL), Nodular lymphocyte predominant Hodgkin's lymphoma, Non-Hodgkin's lymphoma, Plasmablastic lymphoma, Primary central nervous system lymphoma, Primary effusion lymphoma, Splenic marginal zone lymphoma (SMZL), and Waldenstrom's macroglobulinemia, or a combination thereof. In one embodiment, the B-cell lymphoma is Acute Lymphoblastic Leukemia (ALL), Chronic lymphocytic leukemia (CLL), Diffuse large B-cell lymphoma (DLBCL), Follicular lymphoma, Mantle cell lymphoma (MCL), Marginal zone B-cell lymphoma (MZL), Mucosa-Associated Lymphatic Tissue lymphoma (MALT), and Non-Hodgkin's lymphoma. In one embodiment, the B-cell lymphoma is Non-Hodgkin's lymphoma.

The cancer can be a hematologic cancer, e.g., a cancer chosen from one or more of chronic lymphocytic leukemia (CLL), acute leukemias, acute lymphoid leukemia (ALL), B-cell acute lymphoid leukemia (B-ALL), B-cell prolymphocytic leukemia, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, Waldenstrom macroglobulinemia, or pre-leukemia.

The anti-CD19 immunoreagent as described herein may be a "Chimeric Antigen Receptor" (CAR).

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least a binding domain specifically recognizing and capable of binding to an extracellular target antigen (e.g., CD19-ECD expressed on the surface of cancer cells being a target), a transmembrane domain and a cytoplasmic signaling domain (also referred to as "an intracellular signaling domain"). The set of polypeptides may be in the same polypeptide chain (e.g., comprise a chimeric fusion protein). However, the set of polypeptides need not be contiguous with each other, e.g., can be in different polypeptide chains. In some embodiments, the set of polypeptides include a dimerization switch that, upon the presence of a dimerization molecule, can couple the polypeptides to one another, e.g., can couple an antigen binding domain to an intracellular signaling domain. Typically, the CAR comprises a chimeric fusion protein comprising an extracellular antigen binding domain, a transmembrane domain and an intracellular signaling domain.

A CAR molecule directed to CD19, can be used as an anti-CD19 immunoreagent in a method of providing an anti-tumor immunity in a subject comprising administering to the subject an effective amount of a cell comprising a CAR molecule. Specifically, CAR-expressing immune effector cells are used (e.g., T cells or NK cells). Specifically, the cell is an autologous or allogenic T cell or NK cell. In the case of allogenic T cells or NK cells, the T cell or NK cell preferably lacks expression or has low expression of a functional TCR or a functional HLA.

The term "isolated" or "isolation" as used herein with respect to a protein, in particular a CD19 or a part thereof e.g., the wtCD19-ECD or CD19-ECD described herein, shall refer to such compound that has been sufficiently separated from the environment with which it would naturally be associated, in particular a recombinant protein isolated from a cell culture supernatant, so as to exist in "purified" or "substantially pure" form. Yet, "isolated" does not necessarily mean the exclusion of artificial or synthetic mixtures with other compounds or materials, or the exclusion of impurities that do not interfere with the fundamental activity, and that may be present, for example, due to incomplete purification. Isolated compounds can be further formulated to produce preparations thereof, and still for practical purposes be isolated—for example, a CD19-ECD can be mixed with pharmaceutically acceptable carriers, including those which are suitable for analytic, diagnostic or therapeutic applications, or excipients when used in diagnosis or therapy, or for analytical purposes. Suitable diagnostic or analytic preparations may include carrier proteins e.g., albumin (BSA or human albumin), or Casein.

The term "purified" as used herein shall refer to a preparation comprising at least 50% (w/w total protein), preferably at least 60%, 70%, 80%, 90% or 95% of a compound (e.g., a CD19-ECD). Purity is measured by methods appropriate for the compound (e.g., chromatographic methods, polyacrylamide gel electrophoresis, HPLC analysis, and the like). An isolated, purified CD19-ECD as described herein may be obtained by purifying the cell culture supernatants to reduce impurities.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The following standard methods are preferred: cell (debris) separation and wash by Microfiltration or Tangential Flow Filter (TFF) or centrifugation, protein purification by precipitation or heat treatment, protein activation by enzymatic digest, protein purification by chromatography, such as ion exchange (IEX), hydrophobic interaction chromatography (HIC), Affinity chromatography, size exclusion (SEC) or HPLC chromatography, protein precipitation of concentration and washing by ultrafiltration steps.

A highly purified product is essentially free from contaminating proteins, and preferably has a purity of at least 70%, more preferred at least 80%, or at least 90%, or even at least 95%, up to 100%. The purified products may be obtained by purification of the cell culture supernatant or else from cellular debris.

An isolated and purified protein can be identified by conventional methods such as Western blot, HPLC, activity assay, or ELISA.

The term "mutagenesis" as used herein shall refer to a method of preparing or providing mutants of a nucleotide sequence and the respective protein encoded by said nucleotide sequence, e.g. through insertion, deletion and/or substitution of one or more nucleotides, so to obtain variants thereof with at least one change in the non-coding or coding region. Mutagenesis may be through random, semi-random or site directed mutation. Specific wtCD19-ECD or mutants thereof including the CD19-ECD described herein and respective nucleotide sequences may be used to produce variants thereof by mutagenesis, such variants being likewise a CD19-ECD as described herein. For example, variants can be produced by a suitable mutagenesis method using wtCD19-ECD or any one of the exemplary CD19-ECD expressed by clones A-W described herein as a parent sequence. Such mutagenesis method encompass those methods of engineering the nucleic acid or de novo synthesizing a nucleotide sequence using the respective parent sequence information as a template.

Any of the exemplary CD19-ECD described herein may, e.g., be used as a parent and modified to generate variants which have substantially the same or even improved thermal stability as the parent exemplary CD19-ECD. For instance, a library of nucleotide sequences may be prepared by mutagenesis of a selected parent nucleotide sequence encoding a CD19-ECD. A library of variants may be used, e.g., to select a CD19-ECD matching the requirements for a recombinant thermostable CD19-ECD as further described herein. Typically large randomized gene libraries are produced with a high gene diversity, which may be selected according to a specifically desired genotype or phenotype.

Certain CD19-ECD variants may be size variants of the wtCD19-ECD or mutants described herein, which at least comprise said first, second and third core regions, wherein one or more of the core regions are optionally connected by a connecting region consisting of e.g. at least any one of 1, 2, 3, 4, 5, 6, 7, 8, 9, or 10 consecutive amino acids, or specifically up to any one of 100, 90, 80, 70, 60, 50, 40, 30, or 20 consecutive amino acids.

Specific mutagenesis methods provide for point mutations of one or more nucleotides in a sequence, in some embodiments tandem point mutations, such as to change at least 2, 3, 4, 5, 6, 7, 8, 9, 10, or even more continuous nucleotides within the nucleotide sequence encoding the CD19-ECD described herein.

A point mutation as described herein is typically at least one of a deletion, insertion, and/or substitution of one or more nucleotides within a nucleotide sequence to achieve the deletion, insertion, and/or substitution of one (only a single one) amino acid at a certain, defined position within the amino acid sequence encoded by said nucleotide sequence. Therefore, the term "point mutation" as used herein shall refer to a mutation of a nucleotide sequence or an amino acid sequence.

In particular, the "stabilizing point mutation" described herein is a point mutation within the amino acid sequence of a CD19-ECD, such as SEQ ID NO:1, within a certain region and at one or more positions further described herein, which may be modified by the respective substitution, insertion, and/or deletion of one or more nucleotides within the nucleotide sequence encoding said CD19-ECD, to result in a mutant CD19-ECD comprising the respective substitution, insertion, and/or deletion of an amino acid within the amino acid sequence compared to the CD19-ECD before such modification. A point mutation or a combination of point mutations at one or more of the positions within SEQ ID NO:1 described herein, is specifically understood as "stabilizing", if resulting in an increased thermal stability compared to the CD19-ECD without such point mutation and combination of point mutations, respectively.

Any mutation within a core regulatory region of an exemplary CD19-ECD described herein is preferably a point mutation which is a certain exemplified amino acid substitution or an alternative amino acid substitution, e.g., a conservative alternative substitution as described in Table 1, such as to maintain (or even improve) the thermal stability of the protein and/or its recognition by an immunoreagent or a conformation-specific anti-CD19 antibody.

The term "nucleotide sequence" or "nucleic acid sequence" used herein refers to either DNA or RNA molecules comprising such nucleotide sequences. "Nucleic acid sequence" or "polynucleotide sequence" or simply "polynucleotide" refers to a single or double-stranded polymer of deoxyribonucleotide or ribonucleotide bases read from the 5' to the 3' end. It includes coding sequences, such as genes, or expression cassettes.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques well-known in the art. For example, a nucleic acid can be chemically synthesized using naturally occurring nucleotides or variously modified nucleotides designed to increase the biological stability of the molecules or to increase the physical stability of the duplex formed upon hybridization. The nucleic acid can comprise any isolated or purified nucleotide sequence which encodes any of the CD19-ECD or functional portions or functional variants thereof, such as the mutant CD19-ECD described herein. Alternatively, the nucleotide sequence can comprise a nucleotide sequence which is degenerate to any of the sequences or a combination of degenerate sequences, or codon-optimized sequences to improve expression in a host cell.

The term "recombinant" as used herein shall mean "being prepared by or the result of genetic engineering" i.e. by human intervention. A recombinant nucleotide sequence may be engineered by introducing one or more point mutations in a parent nucleotide sequence, and may be expressed in a recombinant host cell that comprises an expression cassette including such recombinant nucleotide sequence. The protein expressed by such expression cassette and host cell, respectively, is also referred to as being "recombinant". The term "recombinant" as used herein with respect to a CD19-ECD, particularly refers to a CD19-ECD that is prepared, expressed, created or isolated by recombinant means, such as a CD19-ECD isolated from a host cell transformed to express the CD19-ECD. For the purpose described herein conventional molecular biology, microbiology, and recombinant DNA techniques within the skill of the art may be employed. Such techniques are explained fully in the literature. See, e.g., Maniatis, Fritsch & Sambrook, "Molecular Cloning: A Laboratory Manual, Cold Spring Harbor, (1982).

The term "sample" as used herein shall refer to any material obtained from a preparation to be analysed, in particular a biological sample obtained from a subject, such as a human being, that contains, or potentially contains, an analyte such as a reaction or binding partner specifically recognizing the CD19-ECD described herein. According to a specific example, a biological sample is obtained from a biological material which could contain an anti-CD19 immunoreagent to be determined. The biological sample can be a tissue, fluid or cell culture sample. Examples of samples for use as described herein include, but are not limited to therapeutic or diagnostic preparations of CD19-specific immunoreagents and patient samples, e.g., tissue or body fluids, specifically blood, serum, plasma, bone marrow biopsies, among many others.

Suitable sample preparation methods include method steps to reduce the effect of the biological matrix on the assay of determining the reactivity of the CD19-ECD with the analyte. Such method steps may include but are not limited to, e.g., capture, chromatography, spin-centrifugation and dialysis.

"Sequence identity" with respect to protein sequences and mutants thereof, in particular of a CD19 or a part thereof e.g., the wtCD19-ECD or CD19-ECD described herein, is defined as the percentage of amino acid residues in a candidate sequence that are identical with the amino acid residues in the specific polypeptide sequence to be compared (the "parent sequence"), after aligning the sequence and introducing gaps, if necessary, to achieve the maximum percent sequence identity, with or without considering any conservative substitutions as part of the sequence identity. Those skilled in the art can determine appropriate parameters for measuring alignment, including any algorithms needed to achieve maximal alignment over the full length of the sequences being compared.

The sequence identity of a variant, or mutant as compared to a parent or wild-type amino acid sequence indicates the degree of identity of two or more sequences. Two or more amino acid sequences may have the same or conserved amino acid residues at a corresponding position, to a certain degree, up to 100%.

Sequence similarity searching is an effective and reliable strategy for identifying homologs with excess (e.g., at least 50%) sequence identity. Sequence similarity search tools frequently used are e.g., BLAST, FASTA, and HMMER.

"Percent (%) amino acid sequence identity" with respect to an amino acid sequence, homologs and orthologues described herein is defined as the percentage of amino acid residues in a candidate sequence that are identical with the amino acid residues in the specific polypeptide sequence, after aligning the sequence and introducing gaps, if necessary, to achieve the maximum percent sequence identity, with or without considering any conservative substitutions as part of the sequence identity. For purposes described herein, the sequence identity between two amino acid sequences is preferably determined using the NCBI BLAST program version BLASTP 2.8.1 with the following exemplary parameters: Program: blastp, Word size: 6, Expect value: 10, Hitlist size: 100, Gapcosts: 11.1, Matrix: BLOSUM62, Filter string: F, Compositional adjustment: Conditional compositional score matrix adjustment.

"Percent (%) identity" with respect to a nucleotide sequence e.g., of a gene encoding CD19 or a part thereof e.g., the wt CD19-ECD or CD19-ECD described herein, is defined as the percentage of nucleotides in a candidate DNA sequence that is identical with the nucleotides in the DNA sequence, after aligning the sequence and introducing gaps, if necessary, to achieve the maximum percent sequence identity, with or without considering any conservative substitutions as part of the sequence identity. Alignment for purposes of determining percent nucleotide sequence identity can be achieved in various ways that are within the skill in the art, for instance, using publicly available computer software.

Sequence similarity searches can identify such homologous proteins or genes by detecting excess similarity, and statistically significant similarity that reflects common ancestry. Homologues may encompass orthologues, which are herein understood as the same protein in different organisms, e.g., variants of such protein in different organisms or species.

As used herein, the term "specificity" or "specific binding" refers to a binding reaction which is determinative of the cognate ligand of interest in a heterogeneous population of molecules. Thus, under designated conditions (e.g., immunoassay conditions), an antibody, receptor or an immune cell binds to its particular target, such as a CD19-ECD (e.g., by specifically recognizing an epitope contained herein, such as a conformational epitope) and does not bind in a significant amount to other molecules present in a sample. Specific binding may be determined by a suitable standard assay such as an immunoassay, surface plasmon resonance (SPR), isothermal titration calorimetry (ITC), biolayer interferometry (BLI) etc. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

A specific binding does not exclude certain cross-reactivity with similar antigens, or the same antigens of a different species (analogues). For example, an antibody, receptor or an immune cell may not only specifically bind the wt CD19-ECD, but also cross-react with a mutant CD19-ECD, such as the CD19-ECD described herein.

The term "subject" as used herein shall refer to a warm-blooded mammalian, particularly a human being or a non-human animal. Anti-CD19 immunotherapy may be applied to human beings, but also for veterinary purposes in a wide range of non-human animal species. Thus, the term "subject" may also particularly refer to animals including pets (such as dogs, cats) and equestrian animals (such as horses, camel, dromedary).

For example, the subject may be in need of treatment of a disease condition where anti-CD19 immunotherapy is indicated, and where the effect of such immunotherapy is determined by detecting the anti-CD19 activity in a sample of the subject using the CD19-ECD described herein. The terms "subject" and "patient" are used interchangeably herein. The term "treatment" is meant to include both prophylactic and therapeutic treatment.

According to another example, the CD19-ECD described herein is administered to a subject who is at risk of or suffering from a disease condition associated with side reactions of an anti-CD19 immunotherapy, where soluble CD19 such as the CD19-ECD described herein can be used to decrease the severity of disease symptoms. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "thermal stability" or "thermostability" of a protein is herein understood as follows as the protein stability in terms of denaturation due to temperature alteration and can be determined by the kinetics of protein denaturation during heating. In aqueous solutions the protein adopts a three-dimensional structure to maintain biological functions. When the protein is exposed to higher temperatures, thermal motion causes breakage of the protein structure, the protein unfolds, known as thermal denaturation. One parameter commonly used to describe the thermal stability of a protein is the $T_m$ value (the midpoint of transition during thermal denaturation). Alternatively, a $T_{1/2}$ (half maximum irreversible denaturation temperature; unit: ° C.) value has been defined, describing the temperature where 50% of the binding signal (to a conformationally specific ligand, e.g. an antibody or any other interaction partner) is maintained after a heat incubation (Hasenhindl et al., Protein Eng Des Sel. 2013 October; 26(10):675-82).

By "increased thermal stability" as described herein, it is meant that a mutated protein (e.g., a CD19-ECD mutant) has a higher $T_{1/2}$ value (half maximum irreversible denaturation temperature; unit: ° C.), determined under the same conditions, than the same protein which does not comprise any stabilizing mutation (said another way, the mutated protein unfolds at a higher temperature than a non-mutant protein under the same conditions). "Conditions" as used herein includes, for example, experimental and physiological conditions. More specifically, the $T_{1/2}$ value is defined as the heat incubation temperature, after which 50% of the binding signal of a conformationally specific ligand (e.g. an antibody) is maintained (Hasenhindl et al., 2013, PEDS 26, 675-682; Traxlmayr and Shusta, 2017, Methods in molecular biology 1575, 45-65). For example, the thermostability is measured according to a method described in the Examples section below.

CD19-ECD is assessed as highly instable and difficult to produce recombinantly in various biological systems. Specific sites on the primary amino acid (aa) sequence of the wild type CD19-ECD (CD19-wt) molecule were identified which are alone or in combination with each other responsible for improved physicochemical properties of the CD19 molecule. It has surprisingly been found that the CD19-ECD described herein has a higher thermal stability than wtCD19-ECD, thus, stabilized CD19-ECD mutants were produced by one or more point mutations at certain positions within core regions of the CD19-ECD, thereby obtaining a heretofore unachievable stability of the protein. It was the first time possible to recombinantly produce cell-surface bound CD19-ECD with higher thermal stability as well as soluble CD19-ECD at higher yields in a predominantly monomeric state.

The following items are embodiments described herein:

1. An extracellular domain of CD19 (CD19-ECD) which comprises at least 60% sequence identity to SEQ ID NO:1, a first core region at positions 2-98 of SEQ ID NO:1, a second core region at positions 167-258 of SEQ ID NO:1, a third core region at positions 99-166 of SEQ ID NO:1, and at least one stabilizing point mutation at an amino acid position within said first and/or second and/or third core regions, wherein the CD19-ECD has an increased thermal stability compared to CD19-ECD which consists of an amino acid sequence identified as SEQ ID NO:1.

2. The CD19-ECD of embodiment 1, wherein
   a) said first core region has at least 80% sequence identity to SEQ ID NO:2; and/or
   b) said second core region has at least 80% sequence identity to SEQ ID NO:3; and/or
   c) said third core region has at least 80% sequence identity to SEQ ID NO:4.

3. The CD19-ECD of embodiment 1 or 2, wherein said amino acid position is selected from the group consisting of N14, V16, L20, G26, P27, T28, K44, L47, M56, R57, W62, F64, I65, F66, Q71, T93, L110, G112, L132, P152, T196, K212, E224, G226, L228, A232, A234, K239, H243, L247, H252 and I255.

4. The CD19-ECD of any one of embodiments 1 to 3, wherein said at least one stabilizing point mutation is an amino acid substitution selected from the group consisting of N14D, V16M, L20P, G26D, P27T, T28N, K44R, L47R, M56I, M56V, R57G, R57M, R57S, R57T, W62R, W62S, F64S, I65V, F66L, F66S, Q71R, T93I, L110V, G112D, L132F, P152S, T196A, K212M, K212N, E224D, G226D, G226S, L228M, A232V, A234V, K239T, H243R, L247M, H252Y and I255V, or a conservative amino acid substitution of any of the foregoing.

5. The CD19-ECD of any one of embodiments 1 to 4, which comprises
   a) at least 1, 2, or 3, up to 16 stabilizing point mutations in said first core region; and/or
   b) at least 1, or 2, up to 12 stabilizing point mutations in said second core region; and/or
   c) at least 1, up to 4 stabilizing point mutations in said third core region.

6. The CD19-ECD of any one of embodiments 1 to 5, wherein
   a) the first core region is any one of SEQ ID NO:5-27; and/or
   b) the second core region is any one of SEQ ID NO:28-50; and/or.
   c) the third core region is any one of SEQ ID NO:51-56.

7. The CD19-ECD of any one of embodiments 1 to 6, which further comprises one, two or three of the following features:
   a) one or more of the N-glycosylation sites selected from those located on N67, N106, N119, N162 and N246;
   b) one or more intramolecular disulfide bonds selected from those linking C19 to C242; C78 to C181; and C115 to C154; and
   c) an epitope recognized by an antibody which also specifically recognizes wild-type human CD19 expressed on the surface of native human B-cells.

8. The CD19-ECD of any one of embodiments 1 to 7, which comprises any one of SEQ ID NO:57-79.

9. The CD19-ECD of any one of embodiments 1 to 8, which is fused to a heterologous protein, peptide or amino acid, and/or which is bound to a solid phase or a detectable moiety.

10. A composition of the CD19-ECD of any one of embodiments 1 to 9, wherein at least 20% of the CD19-ECD molecules are monomeric.

11. A diagnostic preparation comprising a CD19-ECD and a diagnostic reagent in a composition or a kit of parts, comprising the components a) the CD19-ECD of any one of embodiments 1 to 9;

b) a diagnostic reagent;

c) and optionally a solid phase to immobilize at least one of the CD19-ECD and the diagnostic reagent, preferably wherein the diagnostic reagent is i) a detectable label, or ii) a reagent specifically reacting with the CD19-ECD and/or the reaction product of the CD19-ECD binding to an anti-CD19 immunoreagent, or iii) a reagent competing with the CD19-ECD binding to an anti-CD19 immunoreagent; or iv) a reagent specifically reacting with a component fused to the CD19-ECD.

12. Use of the CD19-ECD of any one of embodiments 1 to 9 in a method for the in vitro determination of an anti-CD19 immunoreagent in a sample.

13. The use according to embodiment 12, wherein the quality, quantity or potency of said anti-CD19 immunoreagent is determined.

14. The use according to embodiment 12 or 13, wherein the anti-CD19 immunoreagent is specifically recognizing wild-type human CD19 expressed on the surface of native human B-cells.

15. The use according to any one of embodiments 12 to 14, wherein the anti-CD19 immunoreagent is selected from the group consisting of antibodies, antibody fragments, antibody-fusion constructs, bispecific antibodies, trispecific antibodies, immunotoxins, engineered alternative binder scaffolds, chimeric antigen receptors (CARs), human or non-human (e.g., animal or artificial) cells, such as T cells, NK cells or other immune cells, in particular those engineered to express a chimeric antigen receptor (CAR).

16. A method of determining the quality, quantity or potency of an anti-CD19 immunoreagent, comprising a) providing the CD19-ECD of any one of embodiments 1 to 9, and b) in vitro determining the binding of the CD19-ECD to an anti-CD19 immunoreagent in a sample upon incubating the sample under physiological conditions, thereby producing a reaction product, and c) qualitatively and/or quantitatively determining the reaction product, thereby determining the quality, quantity and/or potency of the anti-CD19 immunoreagent to bind wild-type human CD19 antigen expressed on the surface of native human B-cells.

17. The CD19-ECD of any one of embodiments 1 to 9, for use as a medicament in a method of treating a subject in need of neutralizing, or removing a circulating anti-CD19 immunoreagent.

18. A nucleic acid molecule encoding the CD19-ECD of any one of embodiments 1 to 9.

19. A recombinant host cell comprising the nucleic acid molecule of embodiment 18.

20. A method of producing the CD19-ECD of any one of embodiments 1 to 9, wherein a recombinant host cell of embodiment 19 is cultivated or maintained under conditions to produce said CD19-ECD.

The foregoing description will be more fully understood with reference to the following examples. Such examples are, however, merely representative of methods of practicing one or more embodiments of the present invention and should not be read as limiting the scope of invention.

EXAMPLES

Example 1: Directed Evolution of CD19-ECD

Yeast display experiments were performed as described previously (Angelini et al., 2015, Methods in molecular biology 1319, 3-36; Traxlmayr and Shusta, 2017, Methods in molecular biology 1575, 45-65).

Based on the sequence of the extracellular domain of CD19-wildtype (wtCD19-ECD) encompassing residues P1 to P259 of SEQ ID NO:1 a library was constructed by error prone PCR with an average mutation rate of 3.13 per CD19-wt gene. This naïve library was displayed on the surface of yeast using the Saccharomyces cerevisiae strain EBY100. By using the pCT-CON2 vector, the displayed fusion constructs on the surface of yeast showed the following architecture: Aga2p-HA tag-(G4S)3-linker-CD19-wt library-c-myc-tag.

Briefly, cultures were grown to stationary phase in SD-CAA medium overnight, followed by dilution in SD-CAA to an OD600 of 1. After 5 hours, cells were centrifuged, and yeast surface expression was induced by resuspending cells in SG-CAA medium and incubation at 20° C. overnight. For yeast cell sorting using fluorescence activated cell sorting (FACS) all washing and staining procedures were performed in sterile PBSA (PBS+0.1% bovine serum albumin, pH7.4). To normalize for surface display level all cells were incubated with anti-HA (clone 16B12) Alexa Fluor 647 antibody (BioLegend). For detection of natively folded CD19 variants the library was additionally incubated with the rabbit anti-CD19 antibody (clone FMC63, Absolute Antibody Ltd.) which was detected with anti-rabbit F(ab')2 Fragment Alexa Fluor 488 (Cell Signaling). Several FACS rounds were performed including selection for full-length expression level by staining with anti c-myc (clone 9E10) Alexa Fluor 488 antibody (Thermo Fisher Scientific). Moreover, parts of the library were additionally subjected to a heat shock (48° C. for 10 min) to push selection towards higher thermal stability of the protein. For library sequencing after several sorting rounds, plasmid DNA was extracted using the Zymoprep™ yeast plasmid Miniprep II kit (Zymo Research). This extracted plasmid DNA was used for transformation of Escherichia coli.

Example 2: Sequenced Mutations within the CD19-ECD Gene

96 Escherichia coli clones containing plasmid DNA with enriched mutations within the CD19-ECD region were picked and sequenced using the sequencing primer pCT-CON2_bw (5' AAGTACAGTGGGAACAAAG 3', SEQ ID NO:86). A total of 40 different amino acid (aa) mutations positioned at 32 different positions within the CD19-ECD gene could be detected in 23 different clones (Tab. 2).

TABLE 2

| List of amino acid mutations within the CD19-ECD gene (residues P1-P259) detected after sequencing of 96 enriched clones. mutations within CD19-ECD gene (P1-P259) | | | |
|---|---|---|---|
| N14D | R57G | Q71R | G226D |
| V16M | R57M | T93I | G226S |
| L20P | R57S | L110V | L228M |
| G26D | R57T | G112D | A232V |
| P27T | W62R | L132F | A234V |
| T28N | W62S | P152S | K239T |
| K44R | F64S | T196A | H243R |
| L47R | I65V | K212M | L247M |
| M56I | F66L | K212N | H252Y |
| M56V | F66S | E224D | I255V |

The 23 clones of the CD19-ECD variants were named alphabetically, A, B, C . . . to W. Table 3 indicates the number and type of mutation.

TABLE 3

| | Mutations of all 23 CD19-ECD clones (A-W) obtained after sequencing | | | | |
|---|---|---|---|---|---|
| clones | mutation 1 | mutation 2 | mutation 3 | mutation 4 | mutation 5 |
| A | N14D | T28N | L247M | | |
| B | F64S | L132F | K239T | | |
| C | N14D | K44R | W62S | A232V | H243R |
| D | M56I | A232V | | | |
| E | M56V | R57S | F66S | | |

TABLE 3-continued

| | Mutations of all 23 CD19-ECD clones (A-W) obtained after sequencing | | | | |
|---|---|---|---|---|---|
| clones | mutation 1 | mutation 2 | mutation 3 | mutation 4 | mutation 5 |
| F | Q71R | E224D | G226S | | |
| G | M56I | F66L | K212N | | |
| H | R57S | W62R | | | |
| I | R57S | W62R | H252Y | | |
| J | M56I | L132F | A232V | | |
| K | R57M | L228M | A234V | | |
| L | R57T | G112D | | | |
| M | R57T | G226D | | | |
| N | V16M | P27T | M56I | | |
| O | M56I | L110V | T196A | | |
| P | L47R | T93I | | | |
| Q | G26D | M56I | | | |
| R | M56I | | | | |
| S | R57S | I65V | F66S | I255V | |
| T | L20P | R57G | W62R | | |
| U | M56I | W62R | | | |
| V | L20P | M56I | P152S | | |
| W | M56I | K212M | | | |

To characterize the positions of the aa mutations more precisely, the mutations were graded according to the domains. Table 4 describes the individual positions of the 32 sites and the clones (A to W) in which the individual mutations were detected. Table 4.1 discloses specific positions where the CD19-ECD described herein is preferably mutated and specifies preferred features of disulfide bridges and N-glycosylation.

TABLE 4

| | Overview of mutations for all 23 CD19-ECD clones (A-W) corresponding to their respective domain. | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | | natively occuring | | | clones | | | | | | | | | | | | | | | | | | | | | | | |
| domains | No. | aa | position | mutation | A | B | C | D | E | F | G | H | I | J | K | L | M | N | O | P | Q | R | S | T | U | V | W |
| domain 1 | 1 | N | 14 | D | | | | | | | | | | | | | | | | | | | | | | | |
| | 2 | V | 16 | M | | | | | | | | | | | | | | | | | | | | | | | |
| | 3 | L | 20 | P | | | | | | | | | | | | | | | | | | | | | | | |
| | 4 | G | 26 | D | | | | | | | | | | | | | | | | | | | | | | | |
| | 5 | P | 27 | T | | | | | | | | | | | | | | | | | | | | | | | |
| | 6 | T | 28 | N | | | | | | | | | | | | | | | | | | | | | | | |
| | 7 | K | 44 | R | | | | | | | | | | | | | | | | | | | | | | | |
| | 8 | L | 47 | R | | | | | | | | | | | | | | | | | | | | | | | |
| domain 2 | 9 | M | 56 | I | | | | | | | | | | | | | | | | | | | | | | | |
| | | | | V | | | | | | | | | | | | | | | | | | | | | | | |
| | 10 | R | 57 | G | | | | | | | | | | | | | | | | | | | | | | | |
| | | | | M | | | | | | | | | | | | | | | | | | | | | | | |
| | | | | S | | | | | | | | | | | | | | | | | | | | | | | |
| | | | | T | | | | | | | | | | | | | | | | | | | | | | | |
| | 11 | W | 62 | R | | | | | | | | | | | | | | | | | | | | | | | |
| | | | | S | | | | | | | | | | | | | | | | | | | | | | | |
| | 12 | F | 64 | S | | | | | | | | | | | | | | | | | | | | | | | |
| | 13 | I | 65 | V | | | | | | | | | | | | | | | | | | | | | | | |
| | 14 | F | 66 | L | | | | | | | | | | | | | | | | | | | | | | | |
| | | | | S | | | | | | | | | | | | | | | | | | | | | | | |
| | 15 | Q | 71 | R | | | | | | | | | | | | | | | | | | | | | | | |
| | 16 | T | 93 | I | | | | | | | | | | | | | | | | | | | | | | | |
| domain 3 | 17 | L | 110 | V | | | | | | | | | | | | | | | | | | | | | | | |
| | 18 | G | 112 | D | | | | | | | | | | | | | | | | | | | | | | | |
| | 19 | L | 132 | F | | | | | | | | | | | | | | | | | | | | | | | |
| | 20 | P | 152 | S | | | | | | | | | | | | | | | | | | | | | | | |
| domain 2 | 21 | T | 196 | A | | | | | | | | | | | | | | | | | | | | | | | |
| | 22 | K | 212 | M | | | | | | | | | | | | | | | | | | | | | | | |
| | | | | N | | | | | | | | | | | | | | | | | | | | | | | |
| domain 1 | 23 | E | 224 | D | | | | | | | | | | | | | | | | | | | | | | | |
| | 24 | G | 226 | D | | | | | | | | | | | | | | | | | | | | | | | |
| | | | | S | | | | | | | | | | | | | | | | | | | | | | | |
| | 25 | L | 228 | M | | | | | | | | | | | | | | | | | | | | | | | |

TABLE 4-continued

Overview of mutations for all 23 CD19-ECD clones (A-W) corresponding to their respective domain.

| domains | No. | natively occuring aa | position | mutation | clones A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|---|---|---|---|
| | 26 | A | 232 | V | | | | | | | | | | | | | | | | | | | | | | | |
| | 27 | A | 234 | V | | | | | | | | | | | | | | | | | | | | | | | |
| | 28 | K | 239 | T | | | | | | | | | | | | | | | | | | | | | | | |
| | 29 | H | 243 | R | | | | | | | | | | | | | | | | | | | | | | | |
| | 30 | L | 247 | M | | | | | | | | | | | | | | | | | | | | | | | |
| | 31 | H | 252 | Y | | | | | | | | | | | | | | | | | | | | | | | |
| | 32 | I | 255 | V | | | | | | | | | | | | | | | | | | | | | | | |

TABLE 4.1

Specific preferred features of exemplary CD19-ECD

| | Position in SEQ ID NO:1 | Mutation(s) at one or more of the specific positions in SEQ ID NO:1 | Optional N-Glycosylation |
|---|---|---|---|
| First core region: | 2-98 | | |
| Domain 1 | 2-50 | | |
| Domain 2 | 51-98 | M56, R57, W62, F66 | 67 |
| Second core region: | 167-258 | | 246 |
| Domain 1 | 216-258 | A232 | |
| Domain 2 | 167-215 | | |
| Third core region | 99-166 | G112 | 106, 119, 162 |

As described herein, both of said first and second core regions encompass parts of domains 1 and 2. As used herein, the third core region is also termed "domain 3".

Specifically, the CD19-ECD described herein comprises one, two or three intramolecular disulfide bonds, selected from those i. linking C19 to C242; and/or ii. linking C78 to C181; and/or iii. linking C115 to C154.

Example 3: Flow Cytometric Analysis of 15 Individual CD19 Mutants for their Interaction with Conformationally Specific Antibodies 15 of the 23 selected clones (Superfolder 01-15, SF01-15) encompassing between 1 and 5 aa mutations within the CD19-ECD gene were chosen for further characterization and comparison to wtCD19-ECD on the yeast cell surface. Therefore, EBY100 was transformed with individual plasmid preparations of the pCT-CON2 vectors encoding the respective CD19-ECD mutants using the Frozen-EZ Yeast Transformation II Kit (Zymo Research). Table 5 indicates the renaming of the CD19 variants from initial clone names A to W to "Superfolder", SF-01-SF-15, together with the mutations already described in Tab 3.

TABLE 5

Mutations of CD19 mutants (Superfolder 01-15) that were chosen for further analysis on the surface of yeast cells.

| clones | name | mutation 1 | mutation 2 | mutation 3 | mutation 4 | mutation 5 |
|---|---|---|---|---|---|---|
| A | SF-01 | N14D | T28N | L247M | | |
| B | SF-02 | F64S | L132F | K239T | | |
| C | SF-03 | N14D | K44R | W62S | A232V | H243R |
| D | SF-04 | M56I | A232V | | | |
| E | SF-05 | M56V | R575 | F665 | | |
| G | SF-06 | M56I | F66L | K212N | | |
| J | SF-07 | M56I | L132F | A232V | | |
| L | SF-08 | R57T | G112D | | | |
| M | SF-09 | R57I | G226D | | | |
| O | SF-10 | M56I | L110V | T196A | | |
| Q | SF-11 | G26D | M56I | | | |
| R | SF-12 | M56I | | | | |
| U | SF-13 | M56I | W62R | | | |
| V | SF-14 | L20P | M56I | P152S | | |
| W | SF-15 | M56I | K212M | | | |

Yeast display experiments were performed as described above. Cultures were grown to stationary phase in SD-CAA medium overnight, followed by dilution in SD-CAA to an $OD_{600}$ of 1. After 5 hours cells were centrifuged, and yeast surface expression was induced by resuspending cells in SG-CAA medium and incubation at 20° C. overnight. For flow cytometric analysis all washing and staining procedures were performed in PBSA (PBS+0.1% bovine serum albumin, pH7.4). To normalize for surface display level all cells were incubated with anti-HA (clone 16B12) Alexa Fluor 647 antibody (BioLegend).

For detection of full-length expression level (FIG. 2A), cells were additionally stained with anti c-myc (clone 9E10) Alexa Fluor 488 antibody (Thermo Fisher Scientific). For analysis of folding of the SF mutants cells were stained with two different conformation specific anti-CD19 antibodies (c=67 nM) (FIGS. 2B and 2C), respectively. Unlabelled rabbit anti-CD19 antibody (clone FMC63, Absolute Antibody Ltd.) was detected with anti-rabbit F(ab')2 Fragment Alexa Fluor 488 (Cell Signaling) and directly labelled anti-CD19 antibody (clone HIB19)-Phycoerythrin (BioLegend) was used in a single staining step. Following a terminal washing step, cells were resuspended and analysed on a FACSCanto II (BD Biosciences). The obtained data demonstrate that all tested CD19-ECD mutants show improved folding (as measured by binding to the conformation specific anti-CD19 antibodies (clones FMC63 and HIB19)) compared to wtCD19-ECD (CD19-wt). Importantly, the anti-CD19 mAb (clone HIB19) was not used during the initial selection process. Nevertheless, the engineered CD19-ECD mutants, which were enriched during that selection, showed markedly increased binding towards the anti-CD19 mAb (clone HIB19) (FIG. 2C), demonstrating that all tested mutants show improved folding properties and therefore recognition by the conformationally specific anti-CD19 mAb (clone HIB19) is improved.

Example 4: Flow Cytometric Measurements for Evaluation of the Thermal Stability of 15 Individual CD19 Mutants For analysis of the thermal stability of the 15 Superfolder mutants (Tab. 5) in comparison to wtCD19-ECD (SEQ ID NO:1), heat shock experiments with recombinant yeast clones were performed as previously described (Hasenhindl et al., 2013, PEDS 26, 675-682; Traxlmayr and Shusta, 2017, Methods in molecular biology 1575, 45-65). Briefly, yeast display was induced as described before in SG-CAA medium. After washing, the cell suspensions were aliquoted in 500 µL portions to 1.5 ml microcentrifuge tubes and incubated for 10 min on ice or at 40° C., 50° C., 60° C., 70° C. or 80° C. respectively. After cooling on ice, the cells were incubated with anti-HA (clone 16B12)-Alexa Fluor 647 antibody (BioLegend) and anti-CD19 antibody (clone HIB19)-Phycoerythrin (BioLegend). Following a terminal washing step, cells were resuspended and analysed on a CytoFLEX S (Beckman Coulter). Data were gated on the displaying yeast population (HA-positive) and fit to the following equation (Traxlmayr and Shusta, 2017, Methods in molecular biology 1575, 45-65).

$$MFI_{tot} = \frac{MFI0 - MFIbg}{1 + \exp\left(\frac{T - T1/2}{b}\right)} + MFIbg \qquad \text{(Equ. 1)}$$

wherein $MFI_{tot}$ is the median fluorescence intensity for binding of anti-CD19 antibody (clone HIB19) after incubation at the temperature T, T is the respective heat incubation temperature, $MFI_0$ is the median fluorescence intensity without heat shock, $MFI_{bg}$ is the background median fluorescence intensity, $T_{1/2}$ is the temperature of half-maximum irreversible denaturation and b is a constant determining the slope of the transition.

TABLE 8

| T$_{1/2}$ values of CD19-wt and Superfolder mutants as shown in FIGS. 3A and 3B including % of improvement of T$_{1/2}$ values compared to CD19-wt. | | | |
| --- | --- | --- | --- |
| clones | name | T$_{1/2}$ | % improvement |
|  | CD19-wt | 48.7 ± 1.11 | — |
| A | SF-01 | 51.6 ± 1.08 | 6.0 |
| B | SF-02 | 56.0 ± 0.66 | 15.0 |
| C | SF-03 | 50.8 ± 0.98 | 4.3 |
| D | SF-04 | 53.1 ± 0.21 | 9.0 |
| E | SF-05 | 56.4 ± 0.86 | 15.8 |
| G | SF-06 | 53.3 ± 0.61 | 9.4 |
| J | SF-07 | 53.3 ± 0.82 | 9.4 |
| L | SF-08 | 54.6 ± 0.40 | 12.1 |
| M | SF-09 | 58.4 ± 0.68 | 19.9 |
| O | SF-10 | 50.6 ± 1.27 | 3.9 |
| Q | SF-11 | 52.7 ± 1.24 | 8.2 |

TABLE 8-continued

| T$_{1/2}$ values of CD19-wt and Superfolder mutants as shown in FIGS. 3A and 3B including % of improvement of T$_{1/2}$ values compared to CD19-wt. | | | |
| --- | --- | --- | --- |
| clones | name | T$_{1/2}$ | % improvement |
| R | SF-12 | 53.1 ± 0.76 | 9.0 |
| U | SF-13 | 55.4 ± 1.45 | 13.8 |
| V | SF-14 | 53.5 ± 0.69 | 9.9 |
| W | SF-15 | 53.4 ± 0.95 | 9.7 |

FIG. 3A shows the half maximum irreversible denaturation temperature (T$_{1/2}$) of SF-01 to SF-15 and of wtCD19-ECD calculated from flow cytometric binding analysis of CD19-ECD variants with the conformational epitope recognized by the anti-CD19 mAb (clone HIB19) after heat treatment of yeast cells. FIG. 3B exemplarily shows the temperature dependent residual binding to the conformationally specific mAb HIB19, as well as the fitted mathematical models according to Equ. 1.

To evaluate the results gained with flow cytometry using the anti-CD19 mAb (clone HIB19), the T$_{1/2}$ values indicated in FIG. 3A were plotted against the geometric mean fluorescence intensity (GMFI) of binding to the anti-CD19 mAb (clone FMC63) indicated in FIG. 2B.

FIG. 4 indicates the relation between the anti-CD19 mAb (clone FMC63) binding and thermal stability of CD19-ECD variants.

Example 5: Soluble Expression of Five Selected SF Mutants in HEK293-6E Cells

Based on the above described experimental yeast surface display data (FIGS. 2, 3 and 4), SF-04, SF-05, SF-08, SF-12 and SF-13 as well as CD19-wt (wtCD19-ECD, SEQ ID NO:1) were chosen for soluble expression in HEK293-6E cells (Table 6).

TABLE 6

| Mutations and T1/2 values of Superfolder mutants that were chosen for soluble expression in HEK293-6E cells. | | | | |
| --- | --- | --- | --- | --- |
| CD19 mutant | mutation 1 | mutation 2 | mutation 3 | T$_{1/2}$ |
| SF-04 | M56I | A232V |  | 53.1 |
| SF-05 | M56V | R57S | F66S | 56.4 |
| SF-08 | R57T | G112D |  | 54.6 |
| SF-12 | M56I |  |  | 52.4 |
| SF-13 | M56I | W62R |  | 55.4 |

For transient expression in HEK293-6E cells, DNA encoding for CD19-wt and the 5 chosen SF mutants (Tab. 6) were amplified from the yeast display vector (pCT-CON2) and cloned as C-terminal fusion constructs to 8× His-tag-AviTag-SUMO-HRV 3C cleavage site into the pTT5 vector (NRC) ((Durocher et al., 2002, Nucleic acids research 30, E9), respectively. Transient transfection of 30 mL of HEK293-6E cell (National Research Council Canada) suspension was performed at a cell density of 1.7×10$^6$ cells mL$^{-1}$ in F17 medium (Thermo Fisher Scientific) supplemented with 0.1% Kolliphor (Sigma-Aldrich), 8 mM L-Glutamine (Roth) and 25 µg mL$^{-1}$ G418 (Biochrom). A total of 1 µg plasmid-DNA and 2 µg PEI MAX (Polysciences Inc.)

per mL culture volume were separately diluted in F17 medium without supplements. As negative control (mock), sterile $H_2O$ instead of plasmid DNA was used. After adding the DNA/PEI mixture, the cells were incubated for 48 h, supplemented with 0.5% (w/v) tryptone N1 (Organotechnie) and 5 mM valproic acid (Sigma-Aldrich) and further cultured for 72 h. Soluble protein was harvested by centrifugation (1100×g, 10 min) and stored at –80° C. or further processed for purification.

37 μL of crude culture supernatant was loaded onto a Bolt™ 4-12% Bis-Tris Plus gel (Invitrogen) and silver stained (FIG. 5). The non-glycosylated fusion constructs have a size of approximately 44 kDa. CD19-ECD exhibits 5 potential N-glycosylation sites and therefore migrates on the gel at approximately 55 kDa. FIG. 5 shows the CD19 Superfolder variants as clearly visible bands between 50 and 60 kDa, while no band was visible in the case of CD19-wt at the mentioned molecular size.

To verify the specificity of the bands a Western blot including purified SF-05 and crude cell culture supernatant of Superfolder variants and of wtCD19-ECD (CD19-wt) was stained. To prepare purified SF-05, the crude culture supernatant was concentrated and buffer-exchanged by TFF (tangential flow filtration system) and purification steps were performed via HisTrap FF and size exclusion chromatography.

18 μL of supernatant and 600 ng of purified SF-05 were loaded onto a NuPAGE™ 4-12% Bis-Tris gel (Invitrogen). Afterwards the gel was blotted onto a PVDF membrane and stained using an anti-6×-His Tag monoclonal antibody conjugated with biotin (Thermo Fisher Scientific) as primary staining step and streptavidin-HRP conjugate (GE Healthcare) as secondary staining step (FIG. 6).

The purified SF-05 variant appeared as a single band at the expected size of a CD19-ECD monomer. While CD19-wt was only visible in aggregated form, the culture supernatants of Superfolder variants showed bands at the expected size of CD19-ECD monomers (in addition to higher molecular weight aggregates), demonstrating that the stabilizing mutations in those Superfolder CD19-ECD mutants at least partly prevented aggregation of the CD19-ECD. Moreover, the ratio of monomeric to aggregated CD19-ECD was analysed using the software ImageQuant TL 7.0 (GE Healthcare) (Tab. 7). For each lane two bands (identical for each lane) were defined (grey frames in FIG. 6). The upper frame comprises the dimeric, trimeric and oligomeric forms of CD19-ECD and the lower frame includes exclusively the monomeric form of CD19-ECD. The Mock lane was used for background subtraction. For each lane, the sum of the pixel intensity of both bands (or frames) was calculated and expressed as a percentage ratio of the monomeric to aggregated content. The SEC purified SF-05 sample contains almost exclusively monomeric CD19-ECD (i.e., 96%). The supernatant of CD19-wt reveals 99% aggregates and hence almost no monomeric form. In contrast, the supernatant samples of Superfolder variants comprise a monomeric CD19-ECD content of up to 48%.

TABLE 7

Ratio of monomeric to aggregated forms of purified SF-05 and supernatants of CD19-wt, SF-04, SF-05, SF-08, SF-12 and SF-13. Ratios refer to bands detected by Western blot (FIG. 6). For each lane two bands were defined, exemplarily represented for purified SF-05 (grey frames in FIG. 6). The upper frame refers to the aggregated content, whereas the lower frame refers to the monomeric content of the respective protein. Analysis was performed using the software ImageQuant TL 7.0 (GE Healthcare).

| Protein | Aggregates (%) | Monomer (%) |
|---|---|---|
| | purified | |
| SF-05 | 4 | 96 |
| | Supernatants (non purified) | |
| CD19-wt | 99 | 1 |
| SF-04 | 52 | 48 |
| SF-05 | 56 | 44 |
| SF-08 | 58 | 42 |
| SF-12 | 65 | 35 |
| SF-13 | 73 | 27 |

Example 6: Bio-Layer Interferometry (BLI) Measurements for Determination of Soluble Expression Level in HEK293-6E Supernatants For determination of soluble expression levels of CD19-wt and SF mutants bio-layer interferometry measurements using an Octet RED96e system (ForteBio) were performed. For generation of a standard curve, a larger amount of the purified SF-05 fusion construct was purified as described above. Anti-penta His (HIS1 K, ForteBio) biosensors were used as catcher for CD19 variants. For acquisition of a standard curve the SF-05 fusion protein was diluted in a range between 1.59 μg/mL and 12 μg/mL in mock supernatant. Appropriate dilutions of the supernatants of CD19-wt and SF mutants in mock supernatant were prepared to fit into the range of the standard curve. Obtained binding rates were used for calculation of expression titers (FIG. 7).

To compare the yeast display system with the mammalian soluble expression system we plotted HEK cell expression titers (quantified by BLI) with MFI of yeast cells analysed by flow cytometry. FIG. 8 shows that yeast surface display levels (c-myc binding, i.e., full-length expression on the surface of yeast) show very good correlation with soluble expression levels in HEK293-6E cells. All data shown are from three individual yeast surface display and HEK expression experiments (n=3).

Example 7: Investigation of the Native Fold of CD19-ECD

For evaluation of the native fold of CD19 mutants the interaction with conformationally specific antibodies is analysed using a flow cytometry protein-protein interaction assay (FCPIA). The method is based upon immobilizing one binding partner on polystyrene beads and measuring the interaction with the fluorescence labelled binding partner using flow cytometry (Blazer et al., 2010, Current protocols in cytometry Chapter 13, Unit 13 11 11-15).

Any one of the exemplary mouse IgG1 kappa monoclonal anti-CD19 antibodies-Phycoerythrin (clone 4G7, HIB19 and SJ25C1, all from BioLegend) are chosen to determine the affinities to the Superfolder CD19 mutants. Therefore, the prediluted antibodies are mixed with polystyrene microparticles (BD™ CompBeads Set Anti-Mouse Ig K), respectively and incubated for 30 minutes at room temperature. After a washing step, beads are incubated with various dilutions of SF mutants for 30 minutes, followed by washing and staining of SF mutants by incubation with anti-Penta-His-Alexa Fluor 647 (Qiagen) for 30 minutes. After a final washing step, the interaction is analysed using FACS. For calculation of the equilibrium dissociation constant ($K_D$) values, data points are fitted to a hyperbolic curve according to the following equation (Chao et al., 2006, Nature protocols 1, 755-768).

$$MFI_{tot} = MFI_{min} + \frac{(MFI_{range} \times [SF\ mutant])}{([SF\ mutant] + K_D)} \qquad (Equ.\ 2)$$

wherein
$MFI_{tot}$ is the mean fluorescence intensity,
[SF mutant] is the SF mutant concentration,
$MFI_{min}$ is the minimal fluorescence intensity, and
$MFI_{range}$ is the total range of the measured fluorescence intensity.

Example 8: Flow Cytometric Analysis of the CD19-ECD without Exon 5 (wtCD19-ECD, CD19-Wt) and with Exon 5 (wtCD19-ECD-E5, CD19-Wt-E5) for their Interaction with Conformation Specific Antibodies To select the initial CD19-ECD construct for generating the yeast surface display library, the two different CD19-ECD constructs (i.e., wtCD19-ECD without exon 5 (residues P1-P259, SEQ ID NO:1) and wtCD19-ECD-E5 with exon 5 (P1-K272, SEQ ID NO:83) were tested for binding to the conformational specific anti-CD19 antibodies.

Experiments were performed as described in Example 1 and 3. Briefly, EBY100 was transformed with individual plasmid preparations of the pCT-CON2 vectors encoding for the respective CD19-ECD using the Frozen-EZ Yeast Transformation II Kit (Zymo Research). After induction of yeast surface display, cells were stained with anti-HA (clone 16B12) Alexa Fluor 647 labelled antibody (BioLegend) for detection of expression level. For detection of full-length expression level, cells were stained with anti c-myc mouse IgG1 (clone 9E10, Thermo Fisher Scientific) and goat anti-mouse Alexa Fluor 488 (Life technologies). For analysis of folding, the cells were stained with the two different conformation specific anti-CD19 antibodies (c=67 nM), respectively: i) unlabelled rabbit anti-CD19 antibody (clone FMC63, Absolute Antibody Ltd.) in combination with Alexa Fluor 647 labelled anti-rabbit F(ab')2 Fragment (Cell Signaling) and ii) directly labelled anti-CD19 antibody (clone HIB19)-Phycoerythrin (BioLegend). Cells were analysed on a FACSCanto II (BD Biosciences), a Gallios Flow Cytometer (Beckman Coulter) or a CytoFLEX S (Beckman Coulter) (FIG. 9).

The data clearly demonstrate that binding of the conformation specific anti-CD19 antibodies is almost 30 to 50-fold higher for wtCD19-ECD when compared to wtCD19-ECD-E5. Therefore, wtCD19-ECD (P1-P259, SEQ ID NO:1) was chosen for building the library of wtCD19-ECD variants as described in Example 1.

Example 9: Flow Cytometric Analysis of Single Superfolder Mutants for their Interaction with Conformation Specific Antibodies Compared to the CD19-ECD Mutant N138Q The expression potential of the CD19-ECD was compared to the published N138Q (SEQ ID NO:84, published by Teplyakov et al., 2018, Proteins 86, 495-500) mutant and the Superfolder mutants comprising point mutations. The increased fluorescence signal in flow cytometry gives information if only one specific point mutation is sufficient to improve the binding of conformation specific anti-CD19 antibodies. Two exemplary positions were chosen within domain 2 (i.e., M56 and R57) which are among the most frequently occurring positions identified in the 96 sequenced clones selected according to Example 2. At those two positions different amino acid substitutions were found. Superfolder mutants characterized by only one point mutation (i.e., M56I (SEQ ID NO:74, see SF-12), M56V (SEQ ID NO:80), R57S (SEQ ID NO:81) or R57T (SEQ ID NO:82)) were produced and compared to wtCD19-ECD (SEQ ID NO:1) and the N138Q mutant (SEQ ID NO:84).

The single point mutations (i.e., N138Q, M56I, M56V, R57S or R57T) were introduced using the QuikChange Lightning Site-Directed-Mutagenesis kit (Agilent Technologies) according to the manufacturer's instructions and the pCT-CON2 containing wtCD19-ECD vector as template. Experiments were performed as described in Example 1 and 3. Briefly, EBY100 was transformed with individual plasmid preparations of the pCT-CON2-CD19-ECD single mutant vectors using the Frozen-EZ Yeast Transformation II Kit (Zymo Research). After induction of yeast surface display, cells were stained with anti-HA (clone 16B12) Alexa Fluor 647 antibody (BioLegend) for normalization of expression level (FIG. 10A).

For detection of full-length expression level (FIG. 10B), cells were additionally stained with anti c-myc (clone 9E10) Alexa Fluor 488 antibody (Thermo Fisher Scientific). For analysis of folding, the cells were stained with the two different conformation specific anti-CD19 antibodies (c=67 nM) (FIGS. 10C and 10D), respectively. Unlabelled rabbit anti-CD19 antibody (clone FMC63, Absolute Antibody Ltd.) was detected with anti-rabbit F(ab')2 Fragment Alexa Fluor 488 (Cell Signaling) and directly labelled anti-CD19 antibody (clone HIB19)-Phycoerythrin (BioLegend) was used in a single staining step. Cells were analysed on a CytoFLEX S (Beckman Coulter) (FIG. 10).

The increased fluorescence signals demonstrate that one single point mutation is sufficient to obtain a significant improvement in folding (between 3.5 and 9.2-fold improvement) compared to wtCD19-ECD as shown for binding of the two anti-CD19 antibodies (FIGS. 10C and 10D). This is true for all amino acid substitutions at the respective position (i.e., 56 and 57). In contrast, the mutation at position 138 (N138Q) results in a decrease in binding of the two anti-CD19 antibodies (FIGS. 10C and 10D) compared to wtCD19-ECD indicating that such point mutation at position 138 even reduces the binding to the anti-CD19 antibodies and therefore would not improve the fold of the ECD of CD19.

Example 10: Flow Cytometric Measurements for Evaluation of the Thermal Stability of the Single Superfolder Mutants Compared to the CD19-ECD Mutant N138Q The thermal stability of the single Superfolder mutants of Example 9 (encompassing only one amino acid exchange at the indicated positions) in comparison to the N138Q mutant and wtCD19-ECD was determined as described in Example 1 and 4. Briefly, after induction of yeast surface display, the cells were subjected to different temperatures for 10 min (i.e., ice, 40° C., 50° C., 60° C., 70° C. and 80° C.). After cooling on ice, the cells were incubated with anti-HA (clone 16B12)-Alexa Fluor 647 antibody (BioLegend) and anti-CD19 antibody (clone HIB19)-Phycoerythrin (BioLegend). Cells were analysed on a CytoFLEX S (Beckman Coulter). Recorded data were gated on the displaying yeast population (HA-positive) and fit to Equ. 1.

FIG. 11 shows the half maximum irreversible denaturation temperature ($T_{1/2}$) of wtCD19-ECD, the N138Q mutant and the single Superfolder mutants. Calculated $T_{1/2}$ values are summarized in Tab. 9 including the percentage of improvement (or decline) in comparison to wtCD19-ECD.

TABLE 9

$T_{1/2}$ values of CD19-wt-ECD (in this Table 9 referred to as CD19-wt), the N138Q mutant and single Superfolder mutants including % of improvement (increase in $T_{1/2}$) or decrease in $T_{1/2}$ in case of the N138Q mutant, compared to CD19-wt.

| name | T1/2 | % improvement |
|---|---|---|
| CD19-wt | 46.8 ± 1.79 | — |
| N138Q | 44.4 ± 0.98 | −5.1 |
| M56I (SF-12) | 52.2 ± 1.08 | 11.4 |
| M56V | 50.8 ± 1.63 | 8.5 |
| R57S | 52.9 ± 1.37 | 13.0 |
| R57T | 54.6 ± 1.14 | 16.6 |

Data clearly show that the mutation of the arginine residue at position 57 results in a significant increase in thermal stability demonstrated by an up to 16.6% improvement of the $T_{1/2}$ value when compared to wtCD19-ECD. Similar results were obtained by mutation of the methionine at position 56 with an improvement of the $T_{1/2}$ value of up to 11.4%.

Example 10: Soluble Expression of the Single Superfolder Mutant R57T (SEQ ID NO:82) in HEK293-6E Cells Transient expression in HEK293-6E cells and subsequent SDS-PAGE (FIG. 12A) and anti-His tag Western Blot (FIG. 12B) of crude culture supernatants were performed as described in Example 5. For protein separation, the Bolt™ 4-12% Bis-Tris Plus gels (Invitrogen) were used. Alike FIGS. 5 and 6, FIG. 12 shows no monomeric band for CD19-wt-ECD but higher order oligomers. While the supernatant of the soluble single SF mutant R57T shows oligomers there is also a monomeric band at the correct size of approximately 55 to 65 kDa (marked with the black arrow in FIG. 12). These data confirm yeast display results and indicate that one single point mutation that was selected from the library of Example 2 was sufficient to improve the folding properties of the ECD of CD19.

The invention claimed is:

1. An isolated extracellular domain of CD19 (CD19-ECD) which comprises a first core region at positions 2-98 of SEQ ID NO:1, a second core region at positions 167-258 of SEQ ID NO:1, and a third core region at positions 99-166 of SEQ ID NO:1, wherein the first core region comprises a point mutation selected from the group consisting of M56V, R57S and F66S, and wherein the CD19-ECD has an increased thermal stability compared to CD19-ECD which consists of an amino acid sequence identified as SEQ ID NO:1.

2. The CD19-ECD of claim 1, wherein the CD19-ECD comprises SEQ ID NO:61.

3. The CD19-ECD of claim 1, wherein the CD19-ECD is fused to a heterologous protein, peptide or amino acid, and/or is bound to a solid phase or a detectable moiety.

4. The CD19-ECD of claim 1, wherein the CD19-ECD is in a composition with additional CD19-ECD molecules in which at least 20% of the CD19-ECD molecules of the composition are monomeric.

5. The CD19-ECD of claim 1, wherein the CD19-ECD is in a composition or kit which further comprises a diagnostic reagent, wherein the composition or kit comprises:
   a) the CD19-ECD of claim 1;
   b) the diagnostic reagent;
   c) and optionally a solid phase to immobilize at least one of the CD19-ECD and the diagnostic reagent.

6. The CD19-ECD of claim 5, wherein the diagnostic reagent is:
   i) a detectable label;
   ii) a reagent specifically reacting with the CD19-ECD and/or the reaction product of the CD19-ECD binding to an anti-CD19 immunoreagent;

iii) a reagent competing with the CD19-ECD binding to an anti-CD19 immunoreagent; or
   iv) a reagent specifically reacting with a component fused to the CD19-ECD.

7. The CD19-ECD of claim 1, wherein the point mutation is M56V.

8. The CD19-ECD of claim 1, wherein the point mutation is R57S.

9. The CD19-ECD of claim 1, wherein the point mutation is F66S.

10. A method of determining the quality, quantity or potency of an anti-CD19 immunoreagent, comprising:
   a) providing the CD19-ECD of claim 1,
   b) in vitro determining the binding of the CD19-ECD to an anti-CD19 immunoreagent in a sample upon incubating the sample under physiological conditions, thereby producing a reaction product, and
   c) qualitatively and/or quantitatively determining the reaction product, thereby determining the quality, quantity and/or potency of the anti-CD19 immunoreagent to bind wild-type human CD19 antigen expressed on the surface of native human B-cells.

11. The method of claim 10, wherein the anti-CD19 immunoreagent is selected from the group consisting of antibodies, antibody fragments, antibody-fusion constructs, bispecific antibodies, trispecific antibodies, immunotoxins, engineered alternative binder scaffolds, chimeric antigen receptors (CARs), human or non-human cells.

12. The method of claim 11, wherein the cells are T cells or NK cells.

13. A method of treating a subject who is undergoing therapy with an anti-CD19 immunoreagent comprising administering an effective amount of the CD19-ECD of claim 1 to the subject to neutralize, antagonize or remove circulating anti-CD19 immunoreagent in said subject.

\* \* \* \* \*

SEQUENCE LISTING

<160> NUMBER OF SEQ ID NOS: 86

<210> SEQ ID NO 1
<211> LENGTH: 259
<212> TYPE: PRT
<213> ORGANISM: Homo sapiens

<400> SEQUENCE: 1

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190
```

-continued

```
Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
        210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro

<210> SEQ ID NO 2
<211> LENGTH: 97
<212> TYPE: PRT
<213> ORGANISM: Homo sapiens

<400> SEQUENCE: 2

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
                20                  25                  30

Ser Arg Glu Ser Pro Leu Lys Pro Phe Leu Lys Leu Ser Leu Gly Leu
        35                  40                  45

Pro Gly Leu Gly Ile His Met Arg Pro Leu Ala Ile Trp Leu Phe Ile
        50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly

<210> SEQ ID NO 3
<211> LENGTH: 92
<212> TYPE: PRT
<213> ORGANISM: Homo sapiens

<400> SEQUENCE: 3

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
        35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 4
<211> LENGTH: 68
<212> TYPE: PRT
<213> ORGANISM: Homo sapiens

<400> SEQUENCE: 4

Ser Gly Glu Leu Phe Arg Trp Asn Val Ser Asp Leu Gly Gly Leu Gly
1               5                   10                  15
```

-continued

```
Cys Gly Leu Lys Asn Arg Ser Ser Glu Gly Pro Ser Ser Pro Ser Gly
            20                  25                  30

Lys Leu Met Ser Pro Lys Leu Tyr Val Trp Ala Lys Asp Arg Pro Glu
        35                  40                  45

Ile Trp Glu Gly Glu Pro Pro Cys Leu Pro Pro Arg Asp Ser Leu Asn
    50                  55                  60

Gln Ser Leu Ser
65

<210> SEQ ID NO 5
<211> LENGTH: 97
<212> TYPE: PRT
<213> ORGANISM: Artificial Sequence
<220> FEATURE:
<223> OTHER INFORMATION: core region

<400> SEQUENCE: 5

Glu Glu Pro Leu Val Val Lys Val Glu Glu Gly Asp Asp Ala Val Leu
1               5                   10                  15

Gln Cys Leu Lys Gly Thr Ser Asp Gly Pro Asn Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Met Arg Pro Leu Ala Ile Trp Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly
```

```
<210> SEQ ID NO 6
<211> LENGTH: 97
<212> TYPE: PRT
<213> ORGANISM: Artificial Sequence
<220> FEATURE:
<223> OTHER INFORMATION: core region

<400> SEQUENCE: 6

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Met Arg Pro Leu Ala Ile Trp Leu Ser Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly
```

```
<210> SEQ ID NO 7
<211> LENGTH: 97
<212> TYPE: PRT
<213> ORGANISM: Artificial Sequence
<220> FEATURE:
<223> OTHER INFORMATION: core region
```

-continued

<400> SEQUENCE: 7

Glu Glu Pro Leu Val Val Lys Val Glu Glu Gly Asp Asp Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Arg Leu Ser Leu Gly Leu
        35                  40                  45

Pro Gly Leu Gly Ile His Met Arg Pro Leu Ala Ile Ser Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly

<210> SEQ ID NO 8
<211> LENGTH: 97
<212> TYPE: PRT
<213> ORGANISM: Artificial Sequence
<220> FEATURE:
<223> OTHER INFORMATION: core region

<400> SEQUENCE: 8

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Ile Arg Pro Leu Ala Ile Trp Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly

<210> SEQ ID NO 9
<211> LENGTH: 97
<212> TYPE: PRT
<213> ORGANISM: Artificial Sequence
<220> FEATURE:
<223> OTHER INFORMATION: core region

<400> SEQUENCE: 9

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Val Ser Pro Leu Ala Ile Trp Leu Phe Ile
    50                  55                  60

Ser Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu

-continued

```
              85              90              95

Gly

<210> SEQ ID NO 10
<211> LENGTH: 97
<212> TYPE: PRT
<213> ORGANISM: Artificial Sequence
<220> FEATURE:
<223> OTHER INFORMATION: core region

<400> SEQUENCE: 10

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Met Arg Pro Leu Ala Ile Trp Leu Phe Ile
    50                  55                  60

Phe Asn Val Ser Gln Arg Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly

<210> SEQ ID NO 11
<211> LENGTH: 97
<212> TYPE: PRT
<213> ORGANISM: Artificial Sequence
<220> FEATURE:
<223> OTHER INFORMATION: core region

<400> SEQUENCE: 11

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Ile Arg Pro Leu Ala Ile Trp Leu Phe Ile
    50                  55                  60

Leu Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly

<210> SEQ ID NO 12
<211> LENGTH: 97
<212> TYPE: PRT
<213> ORGANISM: Artificial Sequence
<220> FEATURE:
<223> OTHER INFORMATION: core region

<400> SEQUENCE: 12

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30
```

-continued

```
Ser Arg Glu Ser Pro Leu Lys Pro Phe Leu Lys Leu Ser Leu Gly Leu
        35                  40                  45

Pro Gly Leu Gly Ile His Met Ser Pro Leu Ala Ile Arg Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly
```

```
<210> SEQ ID NO 13
<211> LENGTH: 97
<212> TYPE: PRT
<213> ORGANISM: Artificial Sequence
<220> FEATURE:
<223> OTHER INFORMATION: core region

<400> SEQUENCE: 13

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Met Ser Pro Leu Ala Ile Arg Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly
```

```
<210> SEQ ID NO 14
<211> LENGTH: 97
<212> TYPE: PRT
<213> ORGANISM: Artificial Sequence
<220> FEATURE:
<223> OTHER INFORMATION: core region

<400> SEQUENCE: 14

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Ile Arg Pro Leu Ala Ile Trp Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly
```

```
<210> SEQ ID NO 15
<211> LENGTH: 97
<212> TYPE: PRT
```

-continued

<213> ORGANISM: Artificial Sequence
<220> FEATURE:
<223> OTHER INFORMATION: core region
<400> SEQUENCE: 15

```
Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
                20                  25                  30

Ser Arg Glu Ser Pro Leu Lys Pro Phe Leu Lys Leu Ser Leu Gly Leu
        35                  40                  45

Pro Gly Leu Gly Ile His Met Met Pro Leu Ala Ile Trp Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly
```

<210> SEQ ID NO 16
<211> LENGTH: 97
<212> TYPE: PRT
<213> ORGANISM: Artificial Sequence
<220> FEATURE:
<223> OTHER INFORMATION: core region
<400> SEQUENCE: 16

```
Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
                20                  25                  30

Ser Arg Glu Ser Pro Leu Lys Pro Phe Leu Lys Leu Ser Leu Gly Leu
        35                  40                  45

Pro Gly Leu Gly Ile His Met Thr Pro Leu Ala Ile Trp Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly
```

<210> SEQ ID NO 17
<211> LENGTH: 97
<212> TYPE: PRT
<213> ORGANISM: Artificial Sequence
<220> FEATURE:
<223> OTHER INFORMATION: core region
<400> SEQUENCE: 17

```
Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
                20                  25                  30

Ser Arg Glu Ser Pro Leu Lys Pro Phe Leu Lys Leu Ser Leu Gly Leu
        35                  40                  45

Pro Gly Leu Gly Ile His Met Thr Pro Leu Ala Ile Trp Leu Phe Ile
    50                  55                  60

Phe Asn Val Ser Gln Gln Met Gly Gly Phe Tyr Leu Cys Gln Pro Gly
```

-continued

```
65              70              75              80

Pro Pro Ser Glu Lys Ala Trp Gln Pro Gly Trp Thr Val Asn Val Glu
                85              90              95

Gly

<210> SEQ ID NO 18
<211> LENGTH: 97
<212> TYPE: PRT
<213> ORGANISM: Artificial Sequence
<220> FEATURE:
<223> OTHER INFORMATION: core region

<400> SEQUENCE: 18

Glu Glu Pro Leu Val Val Lys Val Glu Glu Gly Asp Asn Ala Met Leu
1               5               10              15

Gln Cys Leu Lys Gly Thr Ser Asp Gly Thr Thr Gln Gln Leu Thr Trp
                20              25              30

Ser Arg Glu Ser Pro Leu Lys Pro Phe Leu Lys Leu Ser Leu Gly Leu
        35              40              45

Pro Gly Leu Gly Ile His Ile Arg Pro Leu Ala Ile Trp Leu Phe Ile
        50              55              60

Phe Asn Val Ser Gln Gln Met Gly Gly Phe Tyr Leu Cys Gln Pro Gly
65              70              75              80

Pro Pro Ser Glu Lys Ala Trp Gln Pro Gly Trp Thr Val Asn Val Glu
                85              90              95

Gly

<210> SEQ ID NO 19
<211> LENGTH: 97
<212> TYPE: PRT
<213> ORGANISM: Artificial Sequence
<220> FEATURE:
<223> OTHER INFORMATION: core region

<400> SEQUENCE: 19

Glu Glu Pro Leu Val Val Lys Val Glu Glu Gly Asp Asn Ala Val Leu
1               5               10              15

Gln Cys Leu Lys Gly Thr Ser Asp Gly Pro Thr Gln Gln Leu Thr Trp
                20              25              30

Ser Arg Glu Ser Pro Leu Lys Pro Phe Leu Lys Leu Ser Leu Gly Leu
        35              40              45

Pro Gly Leu Gly Ile His Ile Arg Pro Leu Ala Ile Trp Leu Phe Ile
        50              55              60

Phe Asn Val Ser Gln Gln Met Gly Gly Phe Tyr Leu Cys Gln Pro Gly
65              70              75              80

Pro Pro Ser Glu Lys Ala Trp Gln Pro Gly Trp Thr Val Asn Val Glu
                85              90              95

Gly

<210> SEQ ID NO 20
<211> LENGTH: 97
<212> TYPE: PRT
<213> ORGANISM: Artificial Sequence
<220> FEATURE:
<223> OTHER INFORMATION: core region

<400> SEQUENCE: 20

Glu Glu Pro Leu Val Val Lys Val Glu Glu Gly Asp Asn Ala Val Leu
1               5               10              15
```

```
Gln Cys Leu Lys Gly Thr Ser Asp Gly Pro Thr Gln Gln Leu Thr Trp
            20              25              30

Ser Arg Glu Ser Pro Leu Lys Pro Phe Leu Lys Leu Ser Arg Gly Leu
            35              40              45

Pro Gly Leu Gly Ile His Met Arg Pro Leu Ala Ile Trp Leu Phe Ile
        50              55              60

Phe Asn Val Ser Gln Gln Met Gly Gly Phe Tyr Leu Cys Gln Pro Gly
65              70              75              80

Pro Pro Ser Glu Lys Ala Trp Gln Pro Gly Trp Ile Val Asn Val Glu
                85              90              95

Gly

<210> SEQ ID NO 21
<211> LENGTH: 97
<212> TYPE: PRT
<213> ORGANISM: Artificial Sequence
<220> FEATURE:
<223> OTHER INFORMATION: core region

<400> SEQUENCE: 21

Glu Glu Pro Leu Val Val Lys Val Glu Glu Gly Asp Asn Ala Val Leu
1               5               10              15

Gln Cys Leu Lys Gly Thr Ser Asp Asp Pro Thr Gln Gln Leu Thr Trp
            20              25              30

Ser Arg Glu Ser Pro Leu Lys Pro Phe Leu Lys Leu Ser Leu Gly Leu
            35              40              45

Pro Gly Leu Gly Ile His Ile Arg Pro Leu Ala Ile Trp Leu Phe Ile
        50              55              60

Phe Asn Val Ser Gln Gln Met Gly Gly Phe Tyr Leu Cys Gln Pro Gly
65              70              75              80

Pro Pro Ser Glu Lys Ala Trp Gln Pro Gly Trp Thr Val Asn Val Glu
                85              90              95

Gly

<210> SEQ ID NO 22
<211> LENGTH: 97
<212> TYPE: PRT
<213> ORGANISM: Artificial Sequence
<220> FEATURE:
<223> OTHER INFORMATION: core region

<400> SEQUENCE: 22

Glu Glu Pro Leu Val Val Lys Val Glu Glu Gly Asp Asn Ala Val Leu
1               5               10              15

Gln Cys Leu Lys Gly Thr Ser Asp Gly Pro Thr Gln Gln Leu Thr Trp
            20              25              30

Ser Arg Glu Ser Pro Leu Lys Pro Phe Leu Lys Leu Ser Leu Gly Leu
            35              40              45

Pro Gly Leu Gly Ile His Ile Arg Pro Leu Ala Ile Trp Leu Phe Ile
        50              55              60

Phe Asn Val Ser Gln Gln Met Gly Gly Phe Tyr Leu Cys Gln Pro Gly
65              70              75              80

Pro Pro Ser Glu Lys Ala Trp Gln Pro Gly Trp Thr Val Asn Val Glu
                85              90              95

Gly
```

<210> SEQ ID NO 23
<211> LENGTH: 97
<212> TYPE: PRT
<213> ORGANISM: Artificial Sequence
<220> FEATURE:
<223> OTHER INFORMATION: core region

<400> SEQUENCE: 23

```
Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Met Ser Pro Leu Ala Ile Trp Leu Phe Val
    50                  55                  60

Ser Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
            85                  90                  95

Gly
```

<210> SEQ ID NO 24
<211> LENGTH: 97
<212> TYPE: PRT
<213> ORGANISM: Artificial Sequence
<220> FEATURE:
<223> OTHER INFORMATION: core region

<400> SEQUENCE: 24

```
Glu Glu Pro Leu Val Val Lys Val Glu Glu Gly Asp Asn Ala Val Leu
1               5                   10                  15

Gln Cys Pro Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Met Gly Pro Leu Ala Ile Arg Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
            85                  90                  95

Gly
```

<210> SEQ ID NO 25
<211> LENGTH: 97
<212> TYPE: PRT
<213> ORGANISM: Artificial Sequence
<220> FEATURE:
<223> OTHER INFORMATION: core region

<400> SEQUENCE: 25

```
Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30

Ser Arg Glu Ser Pro Leu Lys Pro Phe Leu Lys Leu Ser Leu Gly Leu
        35                  40                  45

Pro Gly Leu Gly Ile His Ile Arg Pro Leu Ala Ile Arg Leu Phe Ile
```

-continued

```
      50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly

<210> SEQ ID NO 26
<211> LENGTH: 97
<212> TYPE: PRT
<213> ORGANISM: Artificial Sequence
<220> FEATURE:
<223> OTHER INFORMATION: core region

<400> SEQUENCE: 26

Glu Glu Pro Leu Val Val Lys Val Glu Glu Gly Asp Asn Ala Val Leu
1                   5                   10                  15

Gln Cys Pro Lys Gly Thr Ser Asp Gly Pro Thr Gln Gln Leu Thr Trp
                20                  25                  30

Ser Arg Glu Ser Pro Leu Lys Pro Phe Leu Lys Leu Ser Leu Gly Leu
        35                  40                  45

Pro Gly Leu Gly Ile His Ile Arg Pro Leu Ala Ile Trp Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly

<210> SEQ ID NO 27
<211> LENGTH: 97
<212> TYPE: PRT
<213> ORGANISM: Artificial Sequence
<220> FEATURE:
<223> OTHER INFORMATION: core region

<400> SEQUENCE: 27

Glu Glu Pro Leu Val Val Lys Val Glu Glu Gly Asp Asn Ala Val Leu
1                   5                   10                  15

Gln Cys Leu Lys Gly Thr Ser Asp Gly Pro Thr Gln Gln Leu Thr Trp
                20                  25                  30

Ser Arg Glu Ser Pro Leu Lys Pro Phe Leu Lys Leu Ser Leu Gly Leu
        35                  40                  45

Pro Gly Leu Gly Ile His Ile Arg Pro Leu Ala Ile Trp Leu Phe Ile
    50                  55                  60

Phe Asn Val Ser Gln Gln Met Gly Gly Phe Tyr Leu Cys Gln Pro Gly
65                  70                  75                  80

Pro Pro Ser Glu Lys Ala Trp Gln Pro Gly Trp Thr Val Asn Val Glu
                85                  90                  95

Gly

<210> SEQ ID NO 28
<211> LENGTH: 92
<212> TYPE: PRT
<213> ORGANISM: Artificial Sequence
<220> FEATURE:
<223> OTHER INFORMATION: core region

<400> SEQUENCE: 28
```

-continued

```
Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Met Thr Met Ser Phe His Leu Glu Ile Thr Ala Arg
                85                  90

<210> SEQ ID NO 29
<211> LENGTH: 92
<212> TYPE: PRT
<213> ORGANISM: Artificial Sequence
<220> FEATURE:
<223> OTHER INFORMATION: core region

<400> SEQUENCE: 29

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Thr Tyr Tyr Cys His Arg Gly Asn
65                  70                  75                  80

Leu Thr Met Ser Phe His Leu Glu Ile Thr Ala Arg
                85                  90

<210> SEQ ID NO 30
<211> LENGTH: 92
<212> TYPE: PRT
<213> ORGANISM: Artificial Sequence
<220> FEATURE:
<223> OTHER INFORMATION: core region

<400> SEQUENCE: 30

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Val Thr Ala Gln Asp Ala Gly Lys Tyr Tyr Cys Arg Arg Gly Asn
65                  70                  75                  80

Leu Thr Met Ser Phe His Leu Glu Ile Thr Ala Arg
                85                  90

<210> SEQ ID NO 31
<211> LENGTH: 92
<212> TYPE: PRT
```

-continued

```
<213> ORGANISM: Artificial Sequence
<220> FEATURE:
<223> OTHER INFORMATION: core region

<400> SEQUENCE: 31

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
            20                  25                  30

His Pro Lys Gly Pro Lys Ser Leu Leu Ser Leu Glu Leu Lys Asp Asp
        35                  40                  45

Arg Pro Ala Arg Asp Met Trp Val Met Glu Thr Gly Leu Leu Leu Pro
    50                  55                  60

Arg Val Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 32
<211> LENGTH: 92
<212> TYPE: PRT
<213> ORGANISM: Artificial Sequence
<220> FEATURE:
<223> OTHER INFORMATION: core region

<400> SEQUENCE: 32

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
            20                  25                  30

His Pro Lys Gly Pro Lys Ser Leu Leu Ser Leu Glu Leu Lys Asp Asp
        35                  40                  45

Arg Pro Ala Arg Asp Met Trp Val Met Glu Thr Gly Leu Leu Leu Pro
    50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 33
<211> LENGTH: 92
<212> TYPE: PRT
<213> ORGANISM: Artificial Sequence
<220> FEATURE:
<223> OTHER INFORMATION: core region

<400> SEQUENCE: 33

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
            20                  25                  30

His Pro Lys Gly Pro Lys Ser Leu Leu Ser Leu Glu Leu Lys Asp Asp
        35                  40                  45

Arg Pro Ala Arg Asp Met Trp Val Met Asp Thr Ser Leu Leu Leu Pro
    50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90
```

-continued

```
<210> SEQ ID NO 34
<211> LENGTH: 92
<212> TYPE: PRT
<213> ORGANISM: Artificial Sequence
<220> FEATURE:
<223> OTHER INFORMATION: core region

<400> SEQUENCE: 34

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Asn Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 35
<211> LENGTH: 92
<212> TYPE: PRT
<213> ORGANISM: Artificial Sequence
<220> FEATURE:
<223> OTHER INFORMATION: core region

<400> SEQUENCE: 35

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 36
<211> LENGTH: 92
<212> TYPE: PRT
<213> ORGANISM: Artificial Sequence
<220> FEATURE:
<223> OTHER INFORMATION: core region

<400> SEQUENCE: 36

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60
```

-continued

```
Arg Ala Thr Ala Gln Asp Ala Gly Lys Tyr Tyr Cys His Arg Gly Asn
65                  70                  75                  80

Leu Thr Met Ser Phe Tyr Leu Glu Ile Thr Ala Arg
                85                  90
```

```
<210> SEQ ID NO 37
<211> LENGTH: 92
<212> TYPE: PRT
<213> ORGANISM: Artificial Sequence
<220> FEATURE:
<223> OTHER INFORMATION: core region

<400> SEQUENCE: 37

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Val Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90
```

```
<210> SEQ ID NO 38
<211> LENGTH: 92
<212> TYPE: PRT
<213> ORGANISM: Artificial Sequence
<220> FEATURE:
<223> OTHER INFORMATION: core region

<400> SEQUENCE: 38

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Met Leu Pro
        50                  55                  60

Arg Ala Thr Val Gln Asp Ala Gly Lys Tyr Tyr Cys His Arg Gly Asn
65                  70                  75                  80

Leu Thr Met Ser Phe His Leu Glu Ile Thr Ala Arg
                85                  90
```

```
<210> SEQ ID NO 39
<211> LENGTH: 92
<212> TYPE: PRT
<213> ORGANISM: Artificial Sequence
<220> FEATURE:
<223> OTHER INFORMATION: core region

<400> SEQUENCE: 39

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
```

-continued

```
            35                  40                  45

Arg Pro Ala Arg Asp Met Trp Val Met Glu Thr Gly Leu Leu Leu Pro
    50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 40
<211> LENGTH: 92
<212> TYPE: PRT
<213> ORGANISM: Artificial Sequence
<220> FEATURE:
<223> OTHER INFORMATION: core region

<400> SEQUENCE: 40

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
        35                  40                  45

Arg Pro Ala Arg Asp Met Trp Val Met Glu Thr Asp Leu Leu Leu Pro
    50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 41
<211> LENGTH: 92
<212> TYPE: PRT
<213> ORGANISM: Artificial Sequence
<220> FEATURE:
<223> OTHER INFORMATION: core region

<400> SEQUENCE: 41

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
        35                  40                  45

Arg Pro Ala Arg Asp Met Trp Val Met Glu Thr Gly Leu Leu Leu Pro
    50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 42
<211> LENGTH: 92
<212> TYPE: PRT
<213> ORGANISM: Artificial Sequence
<220> FEATURE:
<223> OTHER INFORMATION: core region

<400> SEQUENCE: 42

Gln Asp Leu Thr Met Ala Pro Gly Ser Thr Leu Trp Leu Ser Cys Gly
1               5                   10                  15
```

-continued

```
Val Pro Pro Asp Ser Val Ser Arg Gly Pro Leu Ser Trp Ala His Val
        20              25              30

His Pro Lys Gly Pro Lys Ser Leu Leu Ser Leu Glu Leu Lys Asp Asp
        35              40              45

Arg Pro Ala Arg Asp Met Trp Val Met Glu Thr Gly Leu Leu Leu Pro
        50              55              60

Arg Ala Thr Ala Gln Asp Ala Gly Lys Tyr Tyr Cys His Arg Gly Asn
65              70              75              80

Leu Thr Met Ser Phe His Leu Glu Ile Thr Ala Arg
                85              90
```

```
<210> SEQ ID NO 43
<211> LENGTH: 92
<212> TYPE: PRT
<213> ORGANISM: Artificial Sequence
<220> FEATURE:
<223> OTHER INFORMATION: core region

<400> SEQUENCE: 43

Gln Asp Leu Thr Met Ala Pro Gly Ser Thr Leu Trp Leu Ser Cys Gly
1               5               10              15

Val Pro Pro Asp Ser Val Ser Arg Gly Pro Leu Ser Trp Thr His Val
        20              25              30

His Pro Lys Gly Pro Lys Ser Leu Leu Ser Leu Glu Leu Lys Asp Asp
        35              40              45

Arg Pro Ala Arg Asp Met Trp Val Met Glu Thr Gly Leu Leu Leu Pro
        50              55              60

Arg Ala Thr Ala Gln Asp Ala Gly Lys Tyr Tyr Cys His Arg Gly Asn
65              70              75              80

Leu Thr Met Ser Phe His Leu Glu Ile Thr Ala Arg
                85              90
```

```
<210> SEQ ID NO 44
<211> LENGTH: 92
<212> TYPE: PRT
<213> ORGANISM: Artificial Sequence
<220> FEATURE:
<223> OTHER INFORMATION: core region

<400> SEQUENCE: 44

Gln Asp Leu Thr Met Ala Pro Gly Ser Thr Leu Trp Leu Ser Cys Gly
1               5               10              15

Val Pro Pro Asp Ser Val Ser Arg Gly Pro Leu Ser Trp Thr His Val
        20              25              30

His Pro Lys Gly Pro Lys Ser Leu Leu Ser Leu Glu Leu Lys Asp Asp
        35              40              45

Arg Pro Ala Arg Asp Met Trp Val Met Glu Thr Gly Leu Leu Leu Pro
        50              55              60

Arg Ala Thr Ala Gln Asp Ala Gly Lys Tyr Tyr Cys His Arg Gly Asn
65              70              75              80

Leu Thr Met Ser Phe His Leu Glu Ile Thr Ala Arg
                85              90
```

```
<210> SEQ ID NO 45
<211> LENGTH: 92
<212> TYPE: PRT
<213> ORGANISM: Artificial Sequence
<220> FEATURE:
<223> OTHER INFORMATION: core region
```

-continued

<400> SEQUENCE: 45

```
Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90
```

<210> SEQ ID NO 46
<211> LENGTH: 92
<212> TYPE: PRT
<213> ORGANISM: Artificial Sequence
<220> FEATURE:
<223> OTHER INFORMATION: core region

<400> SEQUENCE: 46

```
Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Val Thr Ala Arg
                85                  90
```

<210> SEQ ID NO 47
<211> LENGTH: 92
<212> TYPE: PRT
<213> ORGANISM: Artificial Sequence
<220> FEATURE:
<223> OTHER INFORMATION: core region

<400> SEQUENCE: 47

```
Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90
```

<210> SEQ ID NO 48

-continued

```
<211> LENGTH: 92
<212> TYPE: PRT
<213> ORGANISM: Artificial Sequence
<220> FEATURE:
<223> OTHER INFORMATION: core region

<400> SEQUENCE: 48

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 49
<211> LENGTH: 92
<212> TYPE: PRT
<213> ORGANISM: Artificial Sequence
<220> FEATURE:
<223> OTHER INFORMATION: core region

<400> SEQUENCE: 49

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Lys Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80

Leu Thr Met Ser Phe His Leu Glu Ile Thr Ala Arg
                85                  90

<210> SEQ ID NO 50
<211> LENGTH: 92
<212> TYPE: PRT
<213> ORGANISM: Artificial Sequence
<220> FEATURE:
<223> OTHER INFORMATION: core region

<400> SEQUENCE: 50

Gln Asp Leu Thr Met Ala Pro Gly Ser Thr Leu Trp Leu Ser Cys Gly
1               5                   10                  15

Val Pro Pro Asp Ser Val Ser Arg Gly Pro Leu Ser Trp Thr His Val
                20                  25                  30

His Pro Lys Gly Pro Lys Ser Leu Leu Ser Leu Glu Leu Met Asp Asp
            35                  40                  45

Arg Pro Ala Arg Asp Met Trp Val Met Glu Thr Gly Leu Leu Leu Pro
        50                  55                  60

Arg Ala Thr Ala Gln Asp Ala Gly Lys Tyr Tyr Cys His Arg Gly Asn
65                  70                  75                  80
```

-continued

```
Leu Thr Met Ser Phe His Leu Glu Ile Thr Ala Arg
                85                  90

<210> SEQ ID NO 51
<211> LENGTH: 68
<212> TYPE: PRT
<213> ORGANISM: Homo sapiens

<400> SEQUENCE: 51

Ser Gly Glu Leu Phe Arg Trp Asn Val Ser Asp Leu Gly Gly Leu Gly
1               5                   10                  15

Cys Gly Leu Lys Asn Arg Ser Ser Glu Gly Pro Ser Ser Pro Ser Gly
            20                  25                  30

Lys Leu Met Ser Pro Lys Leu Tyr Val Trp Ala Lys Asp Arg Pro Glu
        35                  40                  45

Ile Trp Glu Gly Glu Pro Pro Cys Leu Pro Pro Arg Asp Ser Leu Asn
    50                  55                  60

Gln Ser Leu Ser
65

<210> SEQ ID NO 52
<211> LENGTH: 68
<212> TYPE: PRT
<213> ORGANISM: Artificial Sequence
<220> FEATURE:
<223> OTHER INFORMATION: core region

<400> SEQUENCE: 52

Ser Gly Glu Leu Phe Arg Trp Asn Val Ser Asp Leu Gly Gly Leu Gly
1               5                   10                  15

Cys Gly Leu Lys Asn Arg Ser Ser Glu Gly Pro Ser Ser Pro Ser Gly
            20                  25                  30

Lys Phe Met Ser Pro Lys Leu Tyr Val Trp Ala Lys Asp Arg Pro Glu
        35                  40                  45

Ile Trp Glu Gly Glu Pro Pro Cys Leu Pro Pro Arg Asp Ser Leu Asn
    50                  55                  60

Gln Ser Leu Ser
65

<210> SEQ ID NO 53
<211> LENGTH: 68
<212> TYPE: PRT
<213> ORGANISM: Artificial Sequence
<220> FEATURE:
<223> OTHER INFORMATION: core region

<400> SEQUENCE: 53

Ser Gly Glu Leu Phe Arg Trp Asn Val Ser Asp Leu Gly Gly Leu Gly
1               5                   10                  15

Cys Gly Leu Lys Asn Arg Ser Ser Glu Gly Pro Ser Ser Pro Ser Gly
            20                  25                  30

Lys Phe Met Ser Pro Lys Leu Tyr Val Trp Ala Lys Asp Arg Pro Glu
        35                  40                  45

Ile Trp Glu Gly Glu Pro Pro Cys Leu Pro Pro Arg Asp Ser Leu Asn
    50                  55                  60

Gln Ser Leu Ser
65

<210> SEQ ID NO 54
<211> LENGTH: 68
```

<212> TYPE: PRT
<213> ORGANISM: Artificial Sequence
<220> FEATURE:
<223> OTHER INFORMATION: core region

<400> SEQUENCE: 54

Ser Gly Glu Leu Phe Arg Trp Asn Val Ser Asp Leu Gly Asp Leu Gly
1               5                   10                  15

Cys Gly Leu Lys Asn Arg Ser Ser Glu Gly Pro Ser Ser Pro Ser Gly
            20                  25                  30

Lys Leu Met Ser Pro Lys Leu Tyr Val Trp Ala Lys Asp Arg Pro Glu
        35                  40                  45

Ile Trp Glu Gly Glu Pro Pro Cys Leu Pro Pro Arg Asp Ser Leu Asn
    50                  55                  60

Gln Ser Leu Ser
65

<210> SEQ ID NO 55
<211> LENGTH: 68
<212> TYPE: PRT
<213> ORGANISM: Artificial Sequence
<220> FEATURE:
<223> OTHER INFORMATION: core region

<400> SEQUENCE: 55

Ser Gly Glu Leu Phe Arg Trp Asn Val Ser Asp Val Gly Gly Leu Gly
1               5                   10                  15

Cys Gly Leu Lys Asn Arg Ser Ser Glu Gly Pro Ser Ser Pro Ser Gly
            20                  25                  30

Lys Leu Met Ser Pro Lys Leu Tyr Val Trp Ala Lys Asp Arg Pro Glu
        35                  40                  45

Ile Trp Glu Gly Glu Pro Pro Cys Leu Pro Pro Arg Asp Ser Leu Asn
    50                  55                  60

Gln Ser Leu Ser
65

<210> SEQ ID NO 56
<211> LENGTH: 68
<212> TYPE: PRT
<213> ORGANISM: Artificial Sequence
<220> FEATURE:
<223> OTHER INFORMATION: core region

<400> SEQUENCE: 56

Ser Gly Glu Leu Phe Arg Trp Asn Val Ser Asp Leu Gly Gly Leu Gly
1               5                   10                  15

Cys Gly Leu Lys Asn Arg Ser Ser Glu Gly Pro Ser Ser Pro Ser Gly
            20                  25                  30

Lys Leu Met Ser Pro Lys Leu Tyr Val Trp Ala Lys Asp Arg Pro Glu
        35                  40                  45

Ile Trp Glu Gly Glu Ser Pro Cys Leu Pro Pro Arg Asp Ser Leu Asn
    50                  55                  60

Gln Ser Leu Ser
65

<210> SEQ ID NO 57
<211> LENGTH: 259
<212> TYPE: PRT
<213> ORGANISM: Artificial Sequence
<220> FEATURE:
<223> OTHER INFORMATION: CD19 mutant

<400> SEQUENCE: 57

```
Pro Glu Glu Pro Leu Val Val Lys Val Glu Glu Gly Asp Asp Ala Val
1               5                   10                  15

Leu Gln Cys Leu Lys Gly Thr Ser Asp Gly Pro Asn Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
            85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Met Thr Met Ser Phe His Leu Glu Ile Thr
                245                 250                 255

Ala Arg Pro
```

```
<210> SEQ ID NO 58
<211> LENGTH: 259
<212> TYPE: PRT
<213> ORGANISM: Artificial Sequence
<220> FEATURE:
<223> OTHER INFORMATION: CD19 mutant
```

<400> SEQUENCE: 58

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Ser
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
```

-continued

```
                    85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Phe Met Ser Pro Lys Leu Tyr Val Trp Ala Lys Asp Arg
            130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
            165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
            210                 215                 220

Thr Gly Leu Leu Leu Pro Arg Ala Thr Ala Gln Asp Ala Gly Thr Tyr
225                 230                 235                 240

Tyr Cys His Arg Gly Asn Leu Thr Met Ser Phe His Leu Glu Ile Thr
            245                 250                 255

Ala Arg Pro

<210> SEQ ID NO 59
<211> LENGTH: 259
<212> TYPE: PRT
<213> ORGANISM: Artificial Sequence
<220> FEATURE:
<223> OTHER INFORMATION: CD19 mutant

<400> SEQUENCE: 59

Pro Glu Glu Pro Leu Val Val Lys Val Glu Glu Gly Asp Asp Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Arg Leu Ser Leu Gly
            35                  40                  45

Leu Pro Gly Leu Gly Ile His Met Arg Pro Leu Ala Ile Ser Leu Phe
            50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
            85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
            130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
            165                 170                 175

Leu Trp Leu Ser Cys Gly Val Pro Pro Asp Ser Val Ser Arg Gly Pro
            180                 185                 190
```

-continued

```
Leu Ser Trp Thr His Val His Pro Lys Gly Pro Lys Ser Leu Leu Ser
        195             200             205

Leu Glu Leu Lys Asp Asp Arg Pro Ala Arg Asp Met Trp Val Met Glu
        210             215             220

Thr Gly Leu Leu Leu Pro Arg Val Thr Ala Gln Asp Ala Gly Lys Tyr
225             230             235             240

Tyr Cys Arg Arg Gly Asn Leu Thr Met Ser Phe His Leu Glu Ile Thr
            245             250             255

Ala Arg Pro

<210> SEQ ID NO 60
<211> LENGTH: 259
<212> TYPE: PRT
<213> ORGANISM: Artificial Sequence
<220> FEATURE:
<223> OTHER INFORMATION: CD19 mutant

<400> SEQUENCE: 60

Pro Glu Glu Pro Leu Val Val Lys Val Glu Glu Gly Asp Asn Ala Val
1               5               10              15

Leu Gln Cys Leu Lys Gly Thr Ser Asp Gly Pro Thr Gln Gln Leu Thr
            20              25              30

Trp Ser Arg Glu Ser Pro Leu Lys Pro Phe Leu Lys Leu Ser Leu Gly
            35              40              45

Leu Pro Gly Leu Gly Ile His Ile Arg Pro Leu Ala Ile Trp Leu Phe
        50              55              60

Ile Phe Asn Val Ser Gln Gln Met Gly Gly Phe Tyr Leu Cys Gln Pro
65              70              75              80

Gly Pro Pro Ser Glu Lys Ala Trp Gln Pro Gly Trp Thr Val Asn Val
            85              90              95

Glu Gly Ser Gly Glu Leu Phe Arg Trp Asn Val Ser Asp Leu Gly Gly
            100             105             110

Leu Gly Cys Gly Leu Lys Asn Arg Ser Ser Glu Gly Pro Ser Ser Pro
        115             120             125

Ser Gly Lys Leu Met Ser Pro Lys Leu Tyr Val Trp Ala Lys Asp Arg
        130             135             140

Pro Glu Ile Trp Glu Gly Glu Pro Pro Cys Leu Pro Pro Arg Asp Ser
145             150             155             160

Leu Asn Gln Ser Leu Ser Gln Asp Leu Thr Met Ala Pro Gly Ser Thr
            165             170             175

Leu Trp Leu Ser Cys Gly Val Pro Pro Asp Ser Val Ser Arg Gly Pro
            180             185             190

Leu Ser Trp Thr His Val His Pro Lys Gly Pro Lys Ser Leu Leu Ser
        195             200             205

Leu Glu Leu Lys Asp Asp Arg Pro Ala Arg Asp Met Trp Val Met Glu
        210             215             220

Thr Gly Leu Leu Leu Pro Arg Val Thr Ala Gln Asp Ala Gly Lys Tyr
225             230             235             240

Tyr Cys His Arg Gly Asn Leu Thr Met Ser Phe His Leu Glu Ile Thr
            245             250             255

Ala Arg Pro

<210> SEQ ID NO 61
<211> LENGTH: 259
<212> TYPE: PRT
```

-continued

<213> ORGANISM: Artificial Sequence
<220> FEATURE:
<223> OTHER INFORMATION: CD19 mutant

<400> SEQUENCE: 61

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Val Ser Pro Leu Ala Ile Trp Leu Phe
    50                  55                  60

Ile Ser Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
        210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro
```

<210> SEQ ID NO 62
<211> LENGTH: 259
<212> TYPE: PRT
<213> ORGANISM: Artificial Sequence
<220> FEATURE:
<223> OTHER INFORMATION: CD19 mutant

<400> SEQUENCE: 62

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Arg Met Gly Gly Phe Tyr Leu Cys Gln Pro
```

-continued

```
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
                115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
                195                 200                 205

Leu Glu Leu Lys Asp Asp Arg Pro Ala Arg Asp Met Trp Val Met Asp
        210                 215                 220

Thr Ser Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro

<210> SEQ ID NO 63
<211> LENGTH: 259
<212> TYPE: PRT
<213> ORGANISM: Artificial Sequence
<220> FEATURE:
<223> OTHER INFORMATION: CD19 mutant

<400> SEQUENCE: 63

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
                20                  25                  30

Trp Ser Arg Glu Ser Pro Leu Lys Pro Phe Leu Lys Leu Ser Leu Gly
        35                  40                  45

Leu Pro Gly Leu Gly Ile His Ile Arg Pro Leu Ala Ile Trp Leu Phe
        50                  55                  60

Ile Leu Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
                115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175
```

-continued

```
Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Asn Asp Asp Arg Pro Ala Arg Asp Met Trp Val Met Glu
            210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                    245                 250                 255

Ala Arg Pro

<210> SEQ ID NO 64
<211> LENGTH: 259
<212> TYPE: PRT
<213> ORGANISM: Artificial Sequence
<220> FEATURE:
<223> OTHER INFORMATION: CD19 mutant

<400> SEQUENCE: 64

Pro Glu Glu Pro Leu Val Val Lys Val Glu Glu Gly Asp Asn Ala Val
1                 5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
            35                  40                  45

Leu Pro Gly Leu Gly Ile His Met Ser Pro Leu Ala Ile Arg Leu Phe
            50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
            85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
            130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
            165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
            210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                    245                 250                 255

Ala Arg Pro
```

```
<210> SEQ ID NO 65
<211> LENGTH: 259
<212> TYPE: PRT
<213> ORGANISM: Artificial Sequence
<220> FEATURE:
<223> OTHER INFORMATION: CD19 mutant

<400> SEQUENCE: 65

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Ser Pro Leu Ala Ile Arg Leu Phe
        50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
        210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe Tyr Leu Glu Ile Thr
                245                 250                 255

Ala Arg Pro

<210> SEQ ID NO 66
<211> LENGTH: 259
<212> TYPE: PRT
<213> ORGANISM: Artificial Sequence
<220> FEATURE:
<223> OTHER INFORMATION: CD19 mutant

<400> SEQUENCE: 66

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Ile Arg Pro Leu Ala Ile Trp Leu Phe
```

```
            50                    55                    60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
            115                 120                 125

Ser Gly Lys Phe Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
        210                 215                 220

Thr Gly Leu Leu Leu Pro Arg Val Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro

<210> SEQ ID NO 67
<211> LENGTH: 259
<212> TYPE: PRT
<213> ORGANISM: Artificial Sequence
<220> FEATURE:
<223> OTHER INFORMATION: CD19 mutant

<400> SEQUENCE: 67

Pro Glu Glu Pro Leu Val Val Lys Val Glu Glu Gly Asp Asn Ala Val
1                   5                   10                  15

Leu Gln Cys Leu Lys Gly Thr Ser Asp Gly Pro Thr Gln Gln Leu Thr
                20                  25                  30

Trp Ser Arg Glu Ser Pro Leu Lys Pro Phe Leu Lys Leu Ser Leu Gly
            35                  40                  45

Leu Pro Gly Leu Gly Ile His Met Met Pro Leu Ala Ile Trp Leu Phe
        50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160
```

-continued

```
Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
                195                 200                 205

Leu Glu Leu Lys Asp Asp Arg Pro Ala Arg Asp Met Trp Val Met Glu
        210                 215                 220

Thr Gly Leu Met Leu Pro Arg Ala Thr Val Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro

<210> SEQ ID NO 68
<211> LENGTH: 259
<212> TYPE: PRT
<213> ORGANISM: Artificial Sequence
<220> FEATURE:
<223> OTHER INFORMATION: CD19 mutant

<400> SEQUENCE: 68

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
                20                  25                  30

Trp Ser Arg Glu Ser Pro Leu Lys Pro Phe Leu Lys Leu Ser Leu Gly
                35                  40                  45

Leu Pro Gly Leu Gly Ile His Met Thr Pro Leu Ala Ile Trp Leu Phe
        50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Asp
                100                 105                 110

Leu Gly Cys Gly Leu Lys Asn Arg Ser Ser Glu Gly Pro Ser Ser Pro
                115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
                195                 200                 205

Leu Glu Leu Lys Asp Asp Arg Pro Ala Arg Asp Met Trp Val Met Glu
        210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255
```

-continued

Ala Arg Pro

<210> SEQ ID NO 69
<211> LENGTH: 259
<212> TYPE: PRT
<213> ORGANISM: Artificial Sequence
<220> FEATURE:
<223> OTHER INFORMATION: CD19 mutant

<400> SEQUENCE: 69

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Thr Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
            85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
            165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
    210                 215                 220

Thr Asp Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro
```

<210> SEQ ID NO 70
<211> LENGTH: 259
<212> TYPE: PRT
<213> ORGANISM: Artificial Sequence
<220> FEATURE:
<223> OTHER INFORMATION: CD19 mutant

<400> SEQUENCE: 70

```
Pro Glu Glu Pro Leu Val Val Lys Val Glu Glu Gly Asp Asn Ala Met
1               5                   10                  15

Leu Gln Cys Leu Lys Gly Thr Ser Asp Gly Thr Thr Gln Gln Leu Thr
            20                  25                  30

Trp Ser Arg Glu Ser Pro Leu Lys Pro Phe Leu Lys Leu Ser Leu Gly
```

-continued

```
                35                    40                    45

Leu Pro Gly Leu Gly Ile His Ile Arg Pro Leu Ala Ile Trp Leu Phe
    50                    55                    60

Ile Phe Asn Val Ser Gln Gln Met Gly Gly Phe Tyr Leu Cys Gln Pro
65                    70                    75                    80

Gly Pro Pro Ser Glu Lys Ala Trp Gln Pro Gly Trp Thr Val Asn Val
                85                    90                    95

Glu Gly Ser Gly Glu Leu Phe Arg Trp Asn Val Ser Asp Leu Gly Gly
                100                   105                   110

Leu Gly Cys Gly Leu Lys Asn Arg Ser Ser Glu Gly Pro Ser Ser Pro
                115                   120                   125

Ser Gly Lys Leu Met Ser Pro Lys Leu Tyr Val Trp Ala Lys Asp Arg
    130                   135                   140

Pro Glu Ile Trp Glu Gly Glu Pro Pro Cys Leu Pro Pro Arg Asp Ser
145                   150                   155                   160

Leu Asn Gln Ser Leu Ser Gln Asp Leu Thr Met Ala Pro Gly Ser Thr
                165                   170                   175

Leu Trp Leu Ser Cys Gly Val Pro Pro Asp Ser Val Ser Arg Gly Pro
                180                   185                   190

Leu Ser Trp Thr His Val His Pro Lys Gly Pro Lys Ser Leu Leu Ser
                195                   200                   205

Leu Glu Leu Lys Asp Asp Arg Pro Ala Arg Asp Met Trp Val Met Glu
    210                   215                   220

Thr Gly Leu Leu Leu Pro Arg Ala Thr Ala Gln Asp Ala Gly Lys Tyr
225                   230                   235                   240

Tyr Cys His Arg Gly Asn Leu Thr Met Ser Phe His Leu Glu Ile Thr
                245                   250                   255

Ala Arg Pro

<210> SEQ ID NO 71
<211> LENGTH: 259
<212> TYPE: PRT
<213> ORGANISM: Artificial Sequence
<220> FEATURE:
<223> OTHER INFORMATION: CD19 mutant

<400> SEQUENCE: 71

Pro Glu Glu Pro Leu Val Val Lys Val Glu Glu Gly Asp Asn Ala Val
1                 5                     10                    15

Leu Gln Cys Leu Lys Gly Thr Ser Asp Gly Pro Thr Gln Gln Leu Thr
                20                    25                    30

Trp Ser Arg Glu Ser Pro Leu Lys Pro Phe Leu Lys Leu Ser Leu Gly
                35                    40                    45

Leu Pro Gly Leu Gly Ile His Ile Arg Pro Leu Ala Ile Trp Leu Phe
    50                    55                    60

Ile Phe Asn Val Ser Gln Gln Met Gly Gly Phe Tyr Leu Cys Gln Pro
65                    70                    75                    80

Gly Pro Pro Ser Glu Lys Ala Trp Gln Pro Gly Trp Thr Val Asn Val
                85                    90                    95

Glu Gly Ser Gly Glu Leu Phe Arg Trp Asn Val Ser Asp Val Gly Gly
                100                   105                   110

Leu Gly Cys Gly Leu Lys Asn Arg Ser Ser Glu Gly Pro Ser Ser Pro
                115                   120                   125

Ser Gly Lys Leu Met Ser Pro Lys Leu Tyr Val Trp Ala Lys Asp Arg
    130                   135                   140
```

```
Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Ala His Val His Pro Lys Gly Pro Lys Ser Leu Leu Ser
                195                 200                 205

Leu Glu Leu Lys Asp Asp Arg Pro Ala Arg Asp Met Trp Val Met Glu
                210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro
```

<210> SEQ ID NO 72
<211> LENGTH: 259
<212> TYPE: PRT
<213> ORGANISM: Artificial Sequence
<220> FEATURE:
<223> OTHER INFORMATION: CD19 mutant

<400> SEQUENCE: 72

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
                20                  25                  30

Trp Ser Arg Glu Ser Pro Leu Lys Pro Phe Leu Lys Leu Ser Arg Gly
            35                  40                  45

Leu Pro Gly Leu Gly Ile His Met Arg Pro Leu Ala Ile Trp Leu Phe
        50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Ile Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
                115                 120                 125

Ser Gly Lys Leu Met Ser Pro Lys Leu Tyr Val Trp Ala Lys Asp Arg
                130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
                195                 200                 205

Leu Glu Leu Lys Asp Asp Arg Pro Ala Arg Asp Met Trp Val Met Glu
                210                 215                 220

Thr Gly Leu Leu Leu Pro Arg Ala Thr Ala Gln Asp Ala Gly Lys Tyr
225                 230                 235                 240
```

-continued

```
Tyr Cys His Arg Gly Asn Leu Thr Met Ser Phe His Leu Glu Ile Thr
            245                 250                 255

Ala Arg Pro

<210> SEQ ID NO 73
<211> LENGTH: 259
<212> TYPE: PRT
<213> ORGANISM: Artificial Sequence
<220> FEATURE:
<223> OTHER INFORMATION: CD19 mutant

<400> SEQUENCE: 73

Pro Glu Glu Pro Leu Val Val Lys Val Glu Glu Gly Asp Asn Ala Val
1               5                   10                  15

Leu Gln Cys Leu Lys Gly Thr Ser Asp Asp Pro Thr Gln Gln Leu Thr
            20                  25                  30

Trp Ser Arg Glu Ser Pro Leu Lys Pro Phe Leu Lys Leu Ser Leu Gly
            35                  40                  45

Leu Pro Gly Leu Gly Ile His Ile Arg Pro Leu Ala Ile Trp Leu Phe
            50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
            85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
            130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
            165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
            210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
            245                 250                 255

Ala Arg Pro

<210> SEQ ID NO 74
<211> LENGTH: 259
<212> TYPE: PRT
<213> ORGANISM: Artificial Sequence
<220> FEATURE:
<223> OTHER INFORMATION: CD19 mutant

<400> SEQUENCE: 74

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
```

-continued

```
                20                  25                  30

Trp Ser Arg Glu Ser Pro Leu Lys Pro Phe Leu Lys Leu Ser Leu Gly
            35                  40                  45

Leu Pro Gly Leu Gly Ile His Ile Arg Pro Leu Ala Ile Trp Leu Phe
        50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
            245                 250                 255

Ala Arg Pro

<210> SEQ ID NO 75
<211> LENGTH: 259
<212> TYPE: PRT
<213> ORGANISM: Artificial Sequence
<220> FEATURE:
<223> OTHER INFORMATION: CD19 mutant

<400> SEQUENCE: 75

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
            35                  40                  45

Leu Pro Gly Leu Gly Ile His Met Ser Pro Leu Ala Ile Trp Leu Phe
        50                  55                  60

Val Ser Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125
```

-continued

```
Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
                195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Val Thr
                245                 250                 255

Ala Arg Pro
```

```
<210> SEQ ID NO 76
<211> LENGTH: 259
<212> TYPE: PRT
<213> ORGANISM: Artificial Sequence
<220> FEATURE:
<223> OTHER INFORMATION: CD19 mutant

<400> SEQUENCE: 76
```

```
Pro Glu Glu Pro Leu Val Val Lys Val Glu Glu Gly Asp Asn Ala Val
1                   5                   10                  15

Leu Gln Cys Pro Lys Gly Thr Ser Asp Gly Pro Thr Gln Gln Leu Thr
                20                  25                  30

Trp Ser Arg Glu Ser Pro Leu Lys Pro Phe Leu Lys Leu Ser Leu Gly
            35                  40                  45

Leu Pro Gly Leu Gly Ile His Met Gly Pro Leu Ala Ile Arg Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
                115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
                195                 200                 205

Leu Glu Leu Lys Asp Asp Arg Pro Ala Arg Asp Met Trp Val Met Glu
    210                 215                 220
```

-continued

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro

<210> SEQ ID NO 77
<211> LENGTH: 259
<212> TYPE: PRT
<213> ORGANISM: Artificial Sequence
<220> FEATURE:
<223> OTHER INFORMATION: CD19 mutant

<400> SEQUENCE: 77

Pro Glu Glu Pro Leu Val Val Lys Val Glu Glu Gly Asp Asn Ala Val
1                   5                   10                  15

Leu Gln Cys Leu Lys Gly Thr Ser Asp Gly Pro Thr Gln Gln Leu Thr
                20                  25                  30

Trp Ser Arg Glu Ser Pro Leu Lys Pro Phe Leu Lys Leu Ser Leu Gly
            35                  40                  45

Leu Pro Gly Leu Gly Ile His Ile Arg Pro Leu Ala Ile Arg Leu Phe
        50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
        210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro

<210> SEQ ID NO 78
<211> LENGTH: 259
<212> TYPE: PRT
<213> ORGANISM: Artificial Sequence
<220> FEATURE:
<223> OTHER INFORMATION: CD19 mutant

<400> SEQUENCE: 78

Pro Glu Glu Pro Leu Val Val Lys Val Glu Glu Gly Asp Asn Ala Val

-continued

```
1               5                    10                   15

Leu Gln Cys Pro Lys Gly Thr Ser Asp Gly Pro Thr Gln Gln Leu Thr
            20                   25                   30

Trp Ser Arg Glu Ser Pro Leu Lys Pro Phe Leu Lys Leu Ser Leu Gly
            35                   40                   45

Leu Pro Gly Leu Gly Ile His Ile Arg Pro Leu Ala Ile Trp Leu Phe
        50                   55                   60

Ile Phe Asn Val Ser Gln Gln Met Gly Gly Phe Tyr Leu Cys Gln Pro
65                   70                   75                   80

Gly Pro Pro Ser Glu Lys Ala Trp Gln Pro Gly Trp Thr Val Asn Val
                85                   90                   95

Glu Gly Ser Gly Glu Leu Phe Arg Trp Asn Val Ser Asp Leu Gly Gly
            100                  105                  110

Leu Gly Cys Gly Leu Lys Asn Arg Ser Ser Glu Gly Pro Ser Ser Pro
            115                  120                  125

Ser Gly Lys Leu Met Ser Pro Lys Leu Tyr Val Trp Ala Lys Asp Arg
        130                  135                  140

Pro Glu Ile Trp Glu Gly Glu Ser Pro Cys Leu Pro Pro Arg Asp Ser
145                  150                  155                  160

Leu Asn Gln Ser Leu Ser Gln Asp Leu Thr Met Ala Pro Gly Ser Thr
                165                  170                  175

Leu Trp Leu Ser Cys Gly Val Pro Pro Asp Ser Val Ser Arg Gly Pro
            180                  185                  190

Leu Ser Trp Thr His Val His Pro Lys Gly Pro Lys Ser Leu Leu Ser
            195                  200                  205

Leu Glu Leu Lys Asp Asp Arg Pro Ala Arg Asp Met Trp Val Met Glu
        210                  215                  220

Thr Gly Leu Leu Leu Pro Arg Ala Thr Ala Gln Asp Ala Gly Lys Tyr
225                  230                  235                  240

Tyr Cys His Arg Gly Asn Leu Thr Met Ser Phe His Leu Glu Ile Thr
                245                  250                  255

Ala Arg Pro
```

```
<210> SEQ ID NO 79
<211> LENGTH: 259
<212> TYPE: PRT
<213> ORGANISM: Artificial Sequence
<220> FEATURE:
<223> OTHER INFORMATION: CD19 mutant

<400> SEQUENCE: 79

Pro Glu Glu Pro Leu Val Val Lys Val Glu Glu Gly Asp Asn Ala Val
1               5                    10                   15

Leu Gln Cys Leu Lys Gly Thr Ser Asp Gly Pro Thr Gln Gln Leu Thr
            20                   25                   30

Trp Ser Arg Glu Ser Pro Leu Lys Pro Phe Leu Lys Leu Ser Leu Gly
            35                   40                   45

Leu Pro Gly Leu Gly Ile His Ile Arg Pro Leu Ala Ile Trp Leu Phe
        50                   55                   60

Ile Phe Asn Val Ser Gln Gln Met Gly Gly Phe Tyr Leu Cys Gln Pro
65                   70                   75                   80

Gly Pro Pro Ser Glu Lys Ala Trp Gln Pro Gly Trp Thr Val Asn Val
                85                   90                   95

Glu Gly Ser Gly Glu Leu Phe Arg Trp Asn Val Ser Asp Leu Gly Gly
            100                  105                  110
```

-continued

```
Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
        195                 200                 205

Leu Glu Leu Met Asp Asp Arg Pro Ala Arg Asp Met Trp Val Met Glu
        210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro

<210> SEQ ID NO 80
<211> LENGTH: 259
<212> TYPE: PRT
<213> ORGANISM: Artificial Sequence
<220> FEATURE:
<223> OTHER INFORMATION: CD19 mutant

<400> SEQUENCE: 80

Pro Glu Glu Pro Leu Val Val Lys Val Glu Glu Gly Asp Asn Ala Val
1                   5                   10                  15

Leu Gln Cys Leu Lys Gly Thr Ser Asp Gly Pro Thr Gln Gln Leu Thr
                20                  25                  30

Trp Ser Arg Glu Ser Pro Leu Lys Pro Phe Leu Lys Leu Ser Leu Gly
        35                  40                  45

Leu Pro Gly Leu Gly Ile His Val Arg Pro Leu Ala Ile Trp Leu Phe
        50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
                180                 185                 190

Leu Ser Trp Thr His Val His Pro Lys Gly Pro Lys Ser Leu Leu Ser
        195                 200                 205
```

-continued

```
Leu Glu Leu Lys Asp Asp Arg Pro Ala Arg Asp Met Trp Val Met Glu
    210             215             220

Thr Gly Leu Leu Leu Pro Arg Ala Thr Ala Gln Asp Ala Gly Lys Tyr
225             230             235             240

Tyr Cys His Arg Gly Asn Leu Thr Met Ser Phe His Leu Glu Ile Thr
            245             250             255

Ala Arg Pro

<210> SEQ ID NO 81
<211> LENGTH: 259
<212> TYPE: PRT
<213> ORGANISM: Artificial Sequence
<220> FEATURE:
<223> OTHER INFORMATION: CD19 mutant

<400> SEQUENCE: 81

Pro Glu Glu Pro Leu Val Val Lys Val Glu Glu Gly Asp Asn Ala Val
1               5               10              15

Leu Gln Cys Leu Lys Gly Thr Ser Asp Gly Pro Thr Gln Gln Leu Thr
            20              25              30

Trp Ser Arg Glu Ser Pro Leu Lys Pro Phe Leu Lys Leu Ser Leu Gly
        35              40              45

Leu Pro Gly Leu Gly Ile His Met Ser Pro Leu Ala Ile Trp Leu Phe
    50              55              60

Ile Phe Asn Val Ser Gln Gln Met Gly Gly Phe Tyr Leu Cys Gln Pro
65              70              75              80

Gly Pro Pro Ser Glu Lys Ala Trp Gln Pro Gly Trp Thr Val Asn Val
            85              90              95

Glu Gly Ser Gly Glu Leu Phe Arg Trp Asn Val Ser Asp Leu Gly Gly
            100             105             110

Leu Gly Cys Gly Leu Lys Asn Arg Ser Ser Glu Gly Pro Ser Ser Pro
        115             120             125

Ser Gly Lys Leu Met Ser Pro Lys Leu Tyr Val Trp Ala Lys Asp Arg
    130             135             140

Pro Glu Ile Trp Glu Gly Glu Pro Pro Cys Leu Pro Pro Arg Asp Ser
145             150             155             160

Leu Asn Gln Ser Leu Ser Gln Asp Leu Thr Met Ala Pro Gly Ser Thr
            165             170             175

Leu Trp Leu Ser Cys Gly Val Pro Pro Asp Ser Val Ser Arg Gly Pro
            180             185             190

Leu Ser Trp Thr His Val His Pro Lys Gly Pro Lys Ser Leu Leu Ser
        195             200             205

Leu Glu Leu Lys Asp Asp Arg Pro Ala Arg Asp Met Trp Val Met Glu
    210             215             220

Thr Gly Leu Leu Leu Pro Arg Ala Thr Ala Gln Asp Ala Gly Lys Tyr
225             230             235             240

Tyr Cys His Arg Gly Asn Leu Thr Met Ser Phe His Leu Glu Ile Thr
            245             250             255

Ala Arg Pro

<210> SEQ ID NO 82
<211> LENGTH: 259
<212> TYPE: PRT
<213> ORGANISM: Artificial Sequence
<220> FEATURE:
<223> OTHER INFORMATION: CD19 mutant
```

-continued

<400> SEQUENCE: 82

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Thr Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
            195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro
```

<210> SEQ ID NO 83
<211> LENGTH: 272
<212> TYPE: PRT
<213> ORGANISM: Homo sapiens

<400> SEQUENCE: 83

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
```

```
                100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
        210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

<210> SEQ ID NO 84
<211> LENGTH: 259
<212> TYPE: PRT
<213> ORGANISM: Artificial Sequence
<220> FEATURE:
<223> OTHER INFORMATION: CD19 mutant

<400> SEQUENCE: 84

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Gln Arg Ser Ser Glu Gly Pro Ser Ser Pro
            115                 120                 125

Ser Gly Lys Leu Met Ser Pro Lys Leu Tyr Val Trp Ala Lys Asp Arg
        130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
```

-continued

```
              195              200              205

Leu Glu Leu Lys Asp Asp Arg Pro Ala Arg Asp Met Trp Val Met Glu
    210              215              220

Thr Gly Leu Leu Leu Pro Arg Ala Thr Ala Gln Asp Ala Gly Lys Tyr
225              230              235              240

Tyr Cys His Arg Gly Asn Leu Thr Met Ser Phe His Leu Glu Ile Thr
                245              250              255

Ala Arg Pro

<210> SEQ ID NO 85
<211> LENGTH: 13
<212> TYPE: PRT
<213> ORGANISM: Homo sapiens

<400> SEQUENCE: 85

Val Leu Trp His Trp Leu Leu Arg Thr Gly Gly Trp Lys
1               5               10

<210> SEQ ID NO 86
<211> LENGTH: 19
<212> TYPE: DNA
<213> ORGANISM: Artificial Sequence
<220> FEATURE:
<223> OTHER INFORMATION: primer

<400> SEQUENCE: 86
aagtacagtg ggaacaaag                                              19
```